United States Patent [19]
King et al.

[11] Patent Number: 5,821,328
[45] Date of Patent: Oct. 13, 1998

[54] GENETIC MARKERS FOR BREAST, OVARIAN, AND PROSTATIC CANCER

[75] Inventors: Mary-Claire King, Berkeley; Lori Friedman, Albany; Beth Ostermeyer, Albany; Sarah Rowell, Kensington; Eric Lynch, Albany; Csilla Szabo, Richmond; Ming Lee, Union City, all of Calif.

[73] Assignee: The Regents of the University of California, Oakland, Calif.

[21] Appl. No.: 825,886

[22] Filed: Apr. 2, 1997

Related U.S. Application Data

[62] Division of Ser. No. 425,061, Apr. 19, 1995, Pat. No. 5,622,829, which is a continuation of Ser. No. 326,983, Oct. 20, 1994, abandoned, which is a continuation of Ser. No. 232,535, Apr. 18, 1994, abandoned, which is a continuation of Ser. No. 163,959, Dec. 8, 1993, abandoned.

[51] Int. Cl.$^6$ .................................................... A61K 38/00
[52] U.S. Cl. ............................ 530/300; 530/324; 530/350
[58] Field of Search ...................................... 530/300, 324, 530/350

*Primary Examiner*—Lila Feisee
*Assistant Examiner*—Susan Ungar
*Attorney, Agent, or Firm*—Richard Aron Osman

[57] ABSTRACT

Specific BRCA1 mutations, PCR primers and hybridization probes are used in nucleic acid-based methods for diagnostic of inheritable breast cancer susceptibility. Additionally, binding agents, such as antibodies, specific for peptides encoded by the subject BRCA1 mutants are used to identify expression products of diagnostic mutations/rare alleles in patient derived fluid or tissue samples. Compositions with high binding affinity for transcription or translation products of the disclosed BRCA1 mutations and alleles are used in therapeutic intervention. Such products include anti-sense nucleic acids, peptides encoded by the subject nucleic acids, and binding agents such as antibodies, specific for such peptides.

13 Claims, No Drawings

GENETIC MARKERS FOR BREAST, OVARIAN, AND PROSTATIC CANCER

CROSS REFERENCE TO RELATED APPLICATION

This application is a divisional application of U.S. patent application Ser. No. 08/425,061, filed Apr. 19, 1995, to issue as U.S. Pat. No. 5,622,829 on Apr. 22, 1997, which is a continuing application of U.S. patent application Ser. No. 08/326,983, filed Oct. 20, 1994, now abandoned, which is a continuing application of U.S. patent application Ser. No. 08/232,535, filed Apr. 18, 1994, now abandoned, which is a continuing application of U.S. patent application Ser. No. 08/163,959, filed Dec.8, 1993, now abandoned.

The research carried out in the subject application was supported in part by grants from the National Institutes of Health. The government may have rights in any patent issuing on this application.

INTRODUCTION

FIELD OF THE INVENTION

The field of the invention is genetic markers for inheritable breast cancer susceptibility.

BACKGROUND

The largest proportion of inherited breast cancer described so far has been attributed to a genetic locus, the BRCA1 locus, on chromosome 17q21 (Hall et al. 1990 Science 250:1684–1689; Narod et al. 1991 Lancet 338:82–83; Easton et al. 1993 Am J Hum Genet 52:678–701). Background material on the genetic markers for breast cancer screening is found in the Jan. 29, 1993 issue of Science, vol 259, especially pages 622–625; see also King et al., 1993 J Amer Med Assoc 269:1975–198. Other relevant research papers include King (1992) Nature Genet 2:125–126; Merette et al. (1992) Amer J Human Genet 50:515–519; NIH/CEPH Collaborative Mapping Group (1992) Science 258:67–86.

Risks of breast cancer to women inheriting the locus are extremely high, exceeding 50% before age 50 and reaching 80% by age 65 (Newman et al. 1988 Proc Natl Acad Sci USA 85:3044–3048; Hall et al. 1992 Amer J Human Genet 50:1235–1242; Easton et al. 1993). Epidemiological evidence for inherited susceptibility to ovarian cancer is even stronger (Cramer et al. 1983 J Natl Cancer Inst 71:711–716; Schildkraut & Thompson 1988 Amer J Epidemiol 128:456–466; Schildkraut et al. 1989 Amer J Hum Genet 45:521–529). According to one study, more than 90% of families with multiple relatives with breast and ovarian cancer trace disease susceptibility to chromosome 17q21 (Easton et al. 1993).

The link between increasing risk of breast and ovarian cancer and inherited susceptibility to these diseases lies in the application of genetics to diagnosis and prevention. Creating molecular tools for earlier diagnosis and developing ways to reverse the first steps of tumorigenesis may be the most effective means of breast and ovarian cancer control.

Our laboratory previously mapped the heritable breast cancer susceptibility gene locus (BRCA1 locus) to a 50 cM region of chromosome 17q (Hall et al. 1990). More recently, we developed new polymorphisms at ERBB2 (Hall and King 1991 Nucl Acids Res 19:2515), THRA1 (Bowcock et al. 1993 Amer J Human Genet 52:718–722), EDH17B (Friedman et al. 1993 Hum Molec Genet 2:821), and multiple anonymous loci (Anderson et al. 1993 Genomics 17:616–623), ultimately developing a high density map of 17q12–q21 (Anderson et al. 1993; see also, Simard et al. 1993 Human Molec Genet 2:1193–1199). We also added families to the genetic study; there are now 100 families for whom transformed lymphocyte lines have been established and all informative relatives genotyped. We used our new markers and the many chromosome 17q polymorphisms developed in the past three years to test linkage in our families, refining the region first to 8 cM (Hall et al. 1992), then to 4 cM (Bowcock et al. 1993), then to 1 Mb based on polymorphisms from our high density map (Anderson et al. 1993; see also Flejter et al., 1993 Genomics 17:624–631). We disclose here a number of mutations in BRCA1 which correlate with disease.

Relevant Literature

The predicted amino acid sequence for a BRCA1 cDNA and familial studies of this gene were described by Miki et al. (1994) Science 266, 66–71 and Futeal et al. (1994) Science 266, 120–122. A study of Canadian cancer families is described in Simard et al. (1994) Nature Genetics 8,392–398. A collaborative survey of BRCA1 mutations is described in Shattuch-Eidens et al. (1995) JAMA 273, 535–541.

SUMMARY OF THE INVENTION

The invention discloses methods and compositions useful in the diagnosis and treatment of breast and ovarian cancer associated with mutations and/or rare alleles of BRCA1, a breast cancer susceptibility gene. Specific genetic probes diagnostic of inheritable breast cancer susceptibility and methods of use are provided. Labelled nucleic acid probes comprising sequences complementary to specified BRCA1 alleles are hybridized to clinical nucleic acid samples. Linkage analysis and inheritance patterns of the disclosed markers are used to diagnose genetic susceptibility. In addition, BRCA1 mutations and/or rare alleles are directly identified by hybridization, polymorphism and or sequence analysis. In another embodiment, labeled binding agents, such as antibodies, specific for peptides encoded by the subject nucleic acids are used to identify expression products of diagnostic mutations or alleles in patient derived fluid or tissue samples. For therapeutic intervention, the invention provides compositions which can functionally interfere with the transcription or translation products of the breast and ovarian cancer susceptibility associated mutations and/or rare alleles within BRCA1. Such products include anti-sense nucleic acids, competitive peptides encoded by the subject nucleic acids, and high affinity binding agents such as antibodies, specific for e.g. translation products of the disclosed BRCA1 mutations and alleles.

DESCRIPTION OF SPECIFIC EMBODIMENTS

We disclose here methods and compositions for determining the presence or absence of BRCA1 mutations and rare alleles or translation products thereof which are useful in the diagnosis of breast and ovarian cancer susceptibility. Tumorigenic BRCA1 alleles include BRCA1 allele #5803 (SEQUENCE ID NO: 1), 9601 (SEQUENCE ID NO:2), 9815 (SEQUENCE ID NO:3), 8403 (SEQUENCE ID NO:4), 8203 (SEQUENCE ID NO:5), 388 (SEQUENCE ID NO:6), 6401 (SEQUENCE ID NO:7), 4406 (SEQUENCE ID NO:8), 10201 (SEQUENCE ID NO:9), 7408 (SEQUENCE ID NO:10), 582 (SEQUENCE ID NO:11) or 77 (SEQUENCE ID NO:12). These nucleic acids or fragments capable of specifically hybridizing with the corresponding allele in the presence of other BRCA1 alleles under stringent conditions find broad diagnostic and therapeutic application. Gene products of the disclosed mutant and/or rare BRCA1 alleles also find a broad range of therapeutic and diagnostic applications. For example, mutant and/or rare allelic BRCA1 peptides are used to generate specific binding compounds. Binding reagents are used diagnostically to distinguish non-tumorigenic wild-type and tumorigenic BRCA1 translation products.

The subject nucleic acids (including fragments thereof) may be single or double stranded and are isolated, partially purified, and/or recombinant. An "isolated" nucleic acid is present as other than a naturally occurring chromosome or transcript in its natural state and isolated from (not joined in sequence to) at least one nucleotide with which it is normally associated on a natural chromosome; a partially pure nucleic acid constitutes at least about 10%, preferably at least about 30%, and more preferably at least about 90% by weight of total nucleic acid present in a given fraction; and a recombinant nucleic acid is joined in sequence to at least one nucleotide with which it is not normally associated on a natural chromosome.

Fragments of the disclosed alleles are sufficiently long for use as specific hybridization probes for detecting endogenous alleles, and particularly to distinguish the disclosed critical rare or mutant alleles which correlate with cancer susceptibility from other BRCA1 alleles, including alleles encoding the BRCA1 translation product displayed in Miki et al (1994) supra, under stringent conditions. Preferred fragments are capable of hybridizing to the corresponding mutant allele under stringency conditions characterized by a hybridization buffer comprising 0% formamide in 0.9 M saline/0.09 M sodium citrate (SSC) buffer at a temperature of 37° C. and remaining when subject to washing at 42° C. with the SSC buffer at 37° C. More preferred fragments will hybridize in a hybridization buffer comprising 20% formamide in 0.9 M saline/0.09 M sodium citrate (SSC) buffer at a temperature of 42° C. and remaining bound when subject to washing at 42° C. with 2 × SSC buffer at 42° C. In any event, the fragments are necessarily of length sufficient to be unique to the corresponding allele; i.e. has a nucleotide sequence at least long enough to define a novel oligonucleotide, usually at least about 14, 16, 18, 20, 22, or 24 bp in length, though such fragment may be joined in sequence to other nucleotides which may be nucleotides which naturally flank the fragment.

In many applications, the nucleic acids are labelled with directly or indirectly detectable signals or means for amplifying a detectable signal. Examples include radiolabels, luminescent (e.g. fluorescent) tags, components of amplified tags such antigen-labelled antibody, biotin-avidin combinations etc. The nucleic acids can be subject to purification, synthesis, modification, sequencing, recombination, incorporation into a variety of vectors, expression, transfection, administration or methods of use disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, N.Y., 1992) or that are otherwise known in the art.

The subject nucleic acids are used in a wide variety of nucleic acid-based diagnostic method that are known to those in the art. Exemplary methods include their use as allele-specific oligonucleotide probes (ASOs), in ligase mediated methods for detecting mutations, as primers in PCR-based methods, direct sequencing methods wherein the clinical BRCA1 nucleic acid sequence is compared with the disclosed mutations and rare alleles, etc. The subject nucleic acids are capable of detecting the presence of a critical mutant or rare BRCA1 allele in a sample and distinguishing the mutant or rare allele from other BRCA1 alleles. For example, where the subject nucleic acids are used as PCR primers or hybridization probes the subject primer or probe comprises an oligonucleotide complementary to a strand of the mutant or rare allele of length sufficient to selectively hybridize with the mutant or rare allele. Generally, these primers and probes comprise at least 16 bp to 24 bp complementary to the mutant or rare allele and may be as large as is convenient for the hybridizations conditions.

Where the critical mutation is a deletion of wild-type sequence, useful primers/probes require wild-type sequences flanking (both sides) the deletion with at least 2, usually at least 3, more usually at least 4, most usually at least 5 bases. Where the mutation is an insertion or substitution which exceeds about 20 bp, it is generally not necessary to include wild-type sequence in the probes/primers. For insertions or substitutions of fewer than 5 bp, preferred nucleic acid portions comprise and flank the substitution/insertion with at least 2, preferably at least 3, more preferably at least 4, most preferably at least 5 bases. For substitutions or insertions from about 5 to about 20 bp, it is usually necessary to include both the entire insertion/substitution and at least 2, usually at least 3, more usually at least 4, most usually at least 5 basis of wild-type sequence of at least one flank of the substitution/insertion.

In addition to their use as diagnostic genetic probes and primers, BRCA1nucleic acids are used to effect a variety of gene-based therapies. See, e.g. Zhu et al. (1993) Science 261, 209–211; Gutierrez et al. (1992) Lancet 339, 715–721; Gary Nabel lab (Dec 1993), Proc. Nat'l. Acad Sci USA. For example, therapeutic nucleic acids are used to modulate cellular expression or intracellular concentration or availability of a tumorigenic BRCA1 translation product by introducing into cells complements of the disclosed nucleic acids. These nucleic acids are typically antisense: single-stranded sequences comprising complements of the disclosed relevant BRCA1 mutant. Antisense modulation of the expression of a given mutant may employ antisense nucleic acids operably linked to gene regulatory sequences. Cell are transfected with a vector comprising such a sequence with a promoter sequence oriented such that transcription of the gene yields an antisense transcript capable of binding to the endogenous tumorigenic BRCA1 allele or transcript. Transcription of the antisense nucleic acid may be constitutive or inducible and the vector may provide for stable extrachromosomal maintenance or integration. Alternatively, single-stranded antisense nucleic acids that bind to BRCA1 genomic DNA or mRNA may be administered to the target cell, in or temporarily isolated from a host, at a concentration that results in a substantial reduction in expression of the targeted translation product.

Various techniques may be employed for introducing of the nucleic acids into viable cells. The techniques vary depending upon whether one is using the subject compositions in culture or in vivo in a host. Various techniques which have been found efficient include transfection with a retrovirus, viral coat protein-liposome mediated transfection, see Dzau et al., *Trends in Biotech* 11, 205–210 (1993). In some situations it is desirable to provide the nucleic acid source with an agent which targets the target cells, such as an antibody specific for a surface membrane protein on the target cell, a ligand for a receptor on the target cell, etc. Where liposomes are employed, proteins which bind to a surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. In liposomes, the decoy concentration in the lumen will generally be in the range of about 0.1 $\mu$M to 20 $\mu$M. For other techniques, the application rate is determined empirically, using conventional techniques to determine desired ranges. Usually, application of the subject therapeutics will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Systemic administration of the nucleic acid using lipofection, liposomes with tissue targeting (e.g. antibody) may also be employed.

The invention also provides isolated translation products of the disclosed BRCA1 allele which distinguish the wild type BRCA1 gene product. For example, for alleles which encode truncated tumorigenic translation product, the C-termninus is used to differentiate wild-type BRCA1. Accordingly, the invention provides the translation product of BRCA1 allele #5803 (SEQUENCE ID NO:13), 9601 (SEQUENCE ID NO:14), 9815 (SEQUENCE ID NO:15), 8203 (SEQUENCE ID NO:17), 388 (SEQUENCE ID NO:18), 6401 (SEQUENCE ID NO:19), 4406 (SEQUENCE ID NO:20), 10201 (SEQUENCE ID NO:21), 7408 (SEQUENCE ID NO:22), 582 (SEQUENCE ID NO:23) or 77 (SEQUENCE ID NO:24), or a C-terminus fragment thereof; and that of #8403 (SEQUENCE ID NO:16), or a fragment thereof comprising Gly at position 61.

The subject mutant and/or rare allelic BRCA1 translation products comprise an amino acid sequence which provides a target for distinguishing the product from that of other BRCA1 alleles. Preferred fragments are capable of eliciting the production of a peptide-specific antibody, in vivo or in vitro, capable of distinguishing a protein comprising the immunogenic peptide from a wild-type BRCA1 translation product. The fragments are necessarily unique to the disclosed allele translation product in that it is not found in any previously known protein and has a length at least long enough to define a novel peptide, from about 5 to about 25 residues, preferably from 6 to 10 residues in length, depending on the particular amino acid sequence.

The subject translation products (including fragments) are either isolated, i.e. unaccompanied by at least some of the material with which they are associated in their natural state); partially purified, i.e. constituting at least about 1%, preferably at least about 10%, and more preferably at least about 50% by weight of the total translation product in a given sample; or pure, i.e. at least about 60%, preferably at least 80%, and more preferably at least about 90% by weight of total translation product. Included in the subject translation product weight are any atoms, molecules, groups, etc. covalently coupled to the subject translation products, such as detectable labels, glycosylations, phosphorylations, etc. The subject translation products may be isolated, purified, modified or joined to other compounds in a variety of ways known to those skilled in the art depending on what other components are present in the sample and to what, if anything, the translation product is covalently linked.

Binding agents specific for the disclosed tumorigenic BRCA1 genes and gene products find particular use in cancer diagnosis. The selected method of diagnosis will depend on the nature of the tumorigenic BRCA1 mutants/rare allele and its transcription or translation product(s). For example, soluble secreted translation products of the disclosed alleles may be detected in a variety of physiologic fluids using a binding agent with a detectable label such as a radiolabel, fluorescer etc. Detection of membrane bound or intracellular products generally requires preliminary isolation of cells (e.g. blood cells) or tissue (e.g. breast biopsy tissue). A wide variety of specific binding assays, e.g. ELISA, may be used.

BRCA1 gene product-specific binding agents are produced in a variety of ways using the compositions disclosed herein. For example, structural x-ray crystallographic and/or NMR data of the mutant and/or rare allelic BRCA1 translation products are used to rationally design binding molecules of determined structure or complementarity. Also, the disclosed mutant and/or rare allelic BRCA1 translation products are used as immunogens to generate specific polyclonal or monoclonal antibodies. See, Harlow and Lane (1988) Antibodies, A Laboratory Manual, Cold Spring Harbor Laboratory, for general methods. Specific antibodies are readily modified to a monovalent form, such as Fab, Fab', or Fv.

Other mutant and/or rare allelic BRCA1 gene-product specific agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. See, e.g. Houghten et al. and Lam et al (1991) Nature 354, 84 and 81, respectively and Blake and Litzi-Davis (1992), Bioconjugate Chem 3, 510.

Useful binding agents are identified with assays employing a compound comprising mutant and/or rare allelic BRCA1 peptides or encoding nucleic acids. A wide variety of in vitro, cell-free binding assays, especially assays for specific binding to immobilized compounds comprising the subject nucleic acid or translation product find convenient use. See, e.g. Fodor et al (1991) Science 251, 767 for the light directed parallel synthesis method. Such assays are amenable to scale-up, high throughput usage suitable for volume drug screening.

Useful agents are typically those that bind the targeted mutant and/or rare allelic BRCA1 gene product with high affinity and specificity and distinguish the tumorigenic BRCA1 mutants/rare alleles from the wild-type BRCA1 gene product. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, sterols, isoprenoids, purines, pyrimidines, derivatives, structural analogs or combinations thereof, and the like. Where the agent is or is encoded by a transfected nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means to enhance efficacy, stability, pharmaceutical compatibility, and the like. In addition, known pharmacological agents may be subject to directed or random chemical modifications, such as acylation, alkylation, esterification, amidification, etc., to produce structural analogs.

Therapeutic applications typically involve binding to and functional disruption of a tumorigenic BRCA1 gene product by an administered high affinity binding agent. For therapeutic uses, the compositions and agents disclosed herein may be administered by any convenient way. Small organics are preferably administered orally; other compositions and agents are preferably administered parenterally, conveniently in a pharmaceutically or physiologically acceptable carrier, e.g., phosphate buffered saline, or the like. Typically, the compositions are added to a retained physiological fluid such as blood or synovial fluid. Generally, the amount administered will be empirically determined, typically in the range of about 10 to 1000 $\mu$g/kg of the recipient. For peptide agents, the concentration will generally be in the range of about 50 to 500 $\mu$g/ml in the dose administered. Other additives may be included, such as stabilizers, bactericides, etc. These additives will be present in conventional amounts.

The following examples are offered by way of illustration and not by way of limitation.

EXAMPLES

Example 1

Positional cloning

Contig construction

YACs. Primers flanking polymorphic repeats in the 4 Mb region of linkage were used to amplify pools from the CEPH, Washington University, and CEPH megaYAC libraries available. 39 YACs were selected. Of these, 23 were tested for chimerism by FISH and 12 found to be chimeric. YACs were aligned to each other by attempting to amplify each YAC with primer pairs from known sequence tagged sites (STSes). More STSes were defined by sequencing the ends of YACs, and these new STSes used for further alignment and YAC identification.

Cosmids. A gridded cosmid library of chromosome 17 was prepared. Alu-Alu PCR products of YACs were hybridized to the cosmid grids and positively hybridizing cosmids used for subsequent studies. Contigs were constructed in two ways. Cosmids with the same restriction patterns were aligned; and, the unique sequences flanking polymorphic markers and our sequenced cDNAs were used as STSes.

Physical mapping by pulsed field gel electrophoresis. Physical distances were estimated by pulsed field gel electrophoresis, using DNA from lymphocyte cell lines of BRCA1-linked patients and of controls. DNA samples were digested with NotI, MluI, RsrII, NruI, SacII, and EciXI. Filters were probed with single-copy sequences isolated from cosmids and later with cDNA clones. Multiple unrelated linked patients and controls were screened to detect large insertions or deletions associated with BRCA1. Results of PFGE were used to define the region first used to screen cDNA libraries as ~1 Mb and the current linked region as $\leq$ 500 kb.

Screening cDNA libraries. We began library screening when the linked region defined by meiotic recombination was ~1 Mb. The first question was what library would optimize the length of cDNA clones, representation of both 5' and 3'ends of genes, and the chances that BRCA1 would be expressed. We chose to use a random primed CDNA library cloned into 1gt10 from cultured (not transformed) fibroblasts from a human female. This library was selected because it had inserts averaging 1.8 kb, with 80% of inserts between 1 and 4 kb, was constructed from cultured fibroblasts known to be "leaky" in gene expression, and was known to include 5' ends of genes. We simultaneously screened three other libraries (from ovary, fetal brain, and mouse mammary epithelium). With one exception (described below), all transcripts from these libraries cross-hybridized to transcripts from the fibroblast library.

The fibroblast library was screened with YAC DNA isolated by PFGE. Pure YAC DNA (100 nanograms) was random primed with both $\propto$p32-dATP (6000mCi/mmole) and $^{32}$P-dCTP (3000mCi/mmole), and used immediately after labelling. Filters from the library were prehybridized with human placental DNA for 24–48 hours. Labelled YAC DNA was hybridized to the filters for 48 hours at 65C. Approximately 250 transcripts were selected by screening with 7 YACs and then ross-hybridized. We also used pools of cosmids from the linked region to screen the fibroblast library. We selected 122 transcripts and cross-hybridized them to clones previously detected by the YACs.

Example 2

Cloning BRCA1 and its characterization

A. Screening for mutations in candidate genes. We initially identified 24 genes in the 1 Mb BRCA1 region defined by meiotic recombination, respective locations on the YAC contig, sizes of representative cDNA clones, numbers of replicates in the library, sizes of transcripts, homologies to known genes, and variants detected. Candidate gene were characterized in the following ways:

(1) Cross-hybridizing clones. cDNA clones isolated from the library are hybridized against each other. Cross-hybridizing clones are considered "siblings" of the clone used as a probe and represent the same gene.

(2) Mapping back. At least one clone from each sibship is mapped back to total human genomic DNA, to cosmids, to YACs, and to somatic cell hybrid lines, some of which contain deletions of 17q and one of which has chromosome 17 as its only human chromosome.

(3) Subcloning and sequencing. One of the longest clones from each sibship is subcloned into M13 and sequenced manually by standard methods, constructing new primers at the end of each fragment to continue sequencing until the end of the clone is reached.

(4) Extending sequences with sibs. In order to find clones that contain more of the gene, the last sequencing primer for the clone and primers made from 1gt10 are used to amplify sibs of the first clone. Sibs that amplify the longest fragments are selected, subcloned, and sequenced. This process is continued until we reach the size of the transcript defined by Northern blot and/or until the 3' sequence is a polyA tail and the 5' sequence has features of the beginning of the coding region.

(5) Southerns. To identify insertion or deletion mutations, genomic DNA from 20 unrelated patients from families with breast cancer linked to 17q (i.e. "linked patients")

and controls are digested with BamI/TaqI and independently with HindIII/HinfI. Each cDNA clone is used to screen Southern blots. Variants have been detected in two genes. Both of these variants are RFLPs, occuring in equal frequency in linked patients and in controls.

(6) Northerns. To identify splice mutations and/or length mutations, we prepared total RNA and polyA+ RNA from germline DNA (from lymphoblast lines) of 20 unrelated linked patients, from ovarian and breast tissues, from fibroblasts, from a HeLa cell line, and from breast cancer cell lines. Northern blots are screened with each gene.

(7) Detection of small mutations. To screen for germline point mutations in patients without encountering introns, we prepared cDNA from poly-A+ mRNA from lymphoblast cell lines of 20 unrelated linked patients and from controls. CDNA has also been made from 65 malignant ovarian cancers from patients not selected for family history. Primers are constructed every ~200 basepairs along the sequence and used to amplify these cDNAs. Genomic DNA has also been prepared from cell lines from all family members (linked and unlinked), from malignant and normal cells from paraffin blocks from their breast and ovarian surgeries, and from malignant and normal cells from 29 breast tumors not selected for family history. For sequences without introns, cDNA and gDNA lengths are equal, and the gDNA samples are amplified as well.

Two mutation detection methods are used to screen each sequence. Amplified products are screened for SSCPs using modifications that enable electrophoresis to be done with only one set of running conditions (Keen et al. 1991 Trends Genet 7:5; Soto and Sukumar 1992 PCR Meth Appl 2:96–98). In order to screen longer segments of DNA (100–1500 bp) and to detect variants missed by SSCP, sequences are also screened for point mutations by CCM (Cotton 1993 Mutation Res 285:125–144) using essentially the protocol of Grompe et al. 1989 Proc Natl Acad Sci USA 86:5888–5892. An endonuclease developed for mismatch detection reduces the toxicity of the method (Youil et al. 1993 Amer J Hum Genet 53 (supplement): abstract 1257).

(8) Polymorphism or mutation. Variants are screened in cases and controls to distinguish polymorphisms from a critical mutation. Linkage of breast cancer to each variant is tested in all informative families.

Example 3

Characterize BRCA1 mutations in germline DNA and breast cancer patients tumors.

A. BRCA1 mutations in chromosome 17g-linked families. Our series of families includes 20 large extended kindreds in which breast and ovarian cancer (and in one family prostatic cancer) are linked to 17q21, with individual lod scores > 1.5. Since linked patients in these families carry mutations in BRCA1, we have identified their mutations first.

TABLE 1 summarizes critical BRCA1 mutations and rare alleles:

| Family | Exon | U14680 nt | Mutation | Amino Acid change | Predicted effect |
|---|---|---|---|---|---|
| 5803 SEQ ID NO: 1 | 3 | 200–253 | exon 3 deleted (54 bp) | 27 Stop | protein truncation SEQ ID NO: 13 |
| 9601 SEQ ID NO: 2 | 3 | 230 | deletion AA | 39 Stop | protein truncation SEQ ID NO: 14 |
| 9815 SEQ ID NO: 3 | Intron 5 | splice donor, bp +1 | substitution G to A →22 bp deletion (base pairs 310–331) in RNA | 64 Stop | protein truncation SEQ ID NO: 15 |
| 8403 SEQ ID NO: 4 | 5 | 300 | substitution T to G | Cys 61 Gly | lose zinc-binding motif SEQ ID NO: 16 |
| 8203 SEQ ID NO: 5 | Intron 5 | splice acceptor, bp −11 | substitution T to G →59 bp insertion of intron into RNA (at base pair 331) | 81 Stop | protein truncation SEQ ID NO: 17 |
| 388 SEQ ID NO: 6 | 11 | 1048 | deletion A | 313 Stop | protein truncation SEQ ID NO: 18 |
| 6401 SEQ ID NO: 7 | 11 | 2415 | deletion AG | Ser 766 Stop | protein truncation SEQ ID NO: 19 |
| 4406 SEQ ID NO: 8 | 11 | 2800 | deletion AA | 901 Stop | protein truncation SEQ ID NO: 20 |
| 10201 SEQ ID NO: 9 | 11 | 2863 | deletion TC | Ser 915 Stop | protein truncation SEQ ID NO: 21 |
| 7408 SEQ ID NO: 10 | 11 | 3726 | substitution C to T | Arg 1203 Stop | protein truncation SEQ ID NO: 22 |
| 582 SEQ ID NO: 11 | 11 | 4184 | deletion TCAA | 1364 Stop | protein truncation SEQ ID NO: 23 |
| 77 SEQ ID NO: 12 | 24 | 5677 | Insertion A | Tyr 1853 Stop | protein truncation SEQ ID NO: 24 |

B. Germline BRCA1 mutations among breast cancer patients in the general population. From each breast cancer patient, not selected for family history, a 30 ml sample of whole blood is drawn into acid citrate dextrose. DNA from the blood is extracted and stored at −70° C. in 3 aliquots. Germline mutations in BRCA1 are identified using the approaches described above and by directly sequencing new mutations. Paraffin-embedded tumor specimens from the same patients are screened for alterations of p53, HER2, PRAD1, and ER. Germline BRCA1 mutations are tested in the tumor blocks.

A preliminary estimate of risk associated with different BRCA1 mutations is obtained from relatives of patients with germline alterations. For each patient with a germline BRCA1 mutation, each surviving sister and mother (and for older patients, brothers as well), DNA is extracted from a blood sample and tested for the presence of the proband's BRCA1 mutation. To ascertain men at risk of prostatic cancer, brothers of breast cancer patients diagnosed after age 55 are also interviewed and sampled. Paraffin blocks from deceased relatives who had cancer are also screened. The frequency of breast, ovarian, or prostatic cancer among relatives carrying BRCA1 mutations is a first estimate of risk of these cancers associated with different mutations.

C. Somatic alterations of BRCA1 in breast tumors. Malignant cells are dissected from normal cells from paraffin blocks. By identifying BRCA1 mutations in these series, we estimate the frequency of somatic BRCA1 alterations, determine BRCA1 mutations characteristic of any particular stage of tumor development, and evaluate their association with prognosis.

D. Characterizing mutant and rare alleles of BRCA1. Mutant or rare BRCA1 allele function and pattern of expression during development are characterized using transformed cells expressing the allele and knockout or transgenic mice. For example, phenotypic changes in the animal or cell line, such as growth rate and anchorage independence are determined. In addition, several methods are used to study loss-of-function mutations, including replacing normal genes with their mutant alleles (BRCA1-/BRCA1-) by homologous recombination in embryonic stem (ES) cells and replacing mutant alleles with their normal counterparts in differentiated cultured cells (Capecchi 1989 Science 244:1288–1292; Weissman et al. 1987 Science 236:175–180; Wang et al. 1993 Oncogene 8:279– 288). Breast carcinoma cell lines are screened for mutation at the BRCA1 locus and a mutant BRCA1 line is selected. Normal and mutant cDNAs of BRCA1 are subcloned into an expression vector carrying genes which confer resistance to ampicillin and geneticin (Baker et al. 1990 Nature 249:912–915). Subclones are transfected into mutant BRCA1 breast cancer cells Geneticin-resistant colonies are isolated and examined for any change in tumorigenic phenotype, such as colony formation in soft agar, increased growth rate, and/or tumor formation in athymic nude mice. In vivo functional demonstrations involve introducing the normal BCRA1 gene into a breast carcinoma cell line mutant at BRCA1 and injecting these BRCA1+ cells into nude mice. Changes observed in tumorigenic growth compared to nude mice injected with BRCA1 mutant breast carcinoma cells are readily observed. For example, correcting the mutant gene decreases the ability of the breast carcinoma cells to form tumors in nude mice (Weissman et al. 1987; Wang et al. 1993).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising:
   a) a C-terminus that is the translation product of BRCA1 allele #5803 (SEQ ID NO:13), 9601 (SEQ ID NO:14), 9815 (SEQ ID NO:15), 8203 (SEQ ID NO:17), 388 (SEQ ID NO:18), 6401 (SEQ ID NO:19), 4406 (SEQ ID NO:20), 10201 (SEQ ID NO:21), 7408 (SEQ ID NO:22), 582 (SEQ ID NO:23) or 77 (SEQ ID NO:24); or
   b) a translation product of BRCA1 allele #8403 (SEQ ID NO:16).

2. An isolated polypeptide according to claim 1, comprising a C-terminus that is the translation product of BRCA1 allele #5803 (SEQ ID NO:13).

3. An isolated polypeptide according to claim 1, comprising a C-terminus that is the translation product of BRCA1 allele #9601 (SEQ ID NO:14).

4. An isolated polypeptide according to claim 1, comprising a C-terminus that is the translation product of BRCA1 allele #9815 (SEQ ID NO:15).

5. An isolated polypeptide according to claim 1, comprising a C-terminus that is the translation product of BRCA1 allele #8203 (SEQ ID NO:17).

6. An isolated polypeptide according to claim 1, a C-terminus that is the translation product of comprising BRCA1 allele #388 (SEQ ID NO:18).

7. An isolated polypeptide according to claim 1, comprising a C-terminus that is the translation product of BRCA1 allele #6401 (SEQ ID NO:19).

8. An isolated polypeptide according to claim 1, comprising a C-terminus that is the translation product of BRCA1 allele #4406 (SEQ ID NO:20).

9. An isolated polypeptide according to claim 1, comprising a C-terminus that is the translation product of BRCA1 allele #10201 (SEQ ID NO:21).

10. An isolated polypeptide according to claim 1, comprising a C-terminus that is the translation product of BRCA1 allele #7408 (SEQ ID NO:22) or C-terminus a fragment thereof.

11. An isolated polypeptide according to claim 1, comprising a C-terminus that is the translation product of BRCA1 allele #582 (SEQ ID NO:23).

12. An isolated polypeptide according to claim 1, comprising a C-terminus that is the translation product of BRCA1 allele #77 (SEQ ID NO:24).

13. An isolated polypeptide according to claim 1, comprising a translation product of BRCA1 allele #8403 (SEQ ID NO:16).

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 5656 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
AGCTCGCTGA    GACTTCCTGG    ACCCCGCACC    AGGCTGTGGG    GTTTCTCAGA    TAACTGGGCC        60

CCTGCGCTCA    GGAGGCCTTC    ACCCTCTGCT    CTGGGTAAAG    TTCATTGGAA    CAGAAAGAAA       120

TGGATTTATC    TGCTCTTCGC    GTTGAAGAAG    TACAAAATGT    CATTAATGCT    ATGCAGAAAA       180

TCTTAGAGTG    TCCCATCTGA    TTTTGCATGC    TGAAACTTCT    CAACCAGAAG    AAAGGGCCTT       240

CACAGTGTCC    TTTATGTAAG    AATGATATAA    CCAAAAGGAG    CCTACAAGAA    AGTACGAGAT       300

TTAGTCAACT    TGTTGAAGAG    CTATTGAAAA    TCATTTGTGC    TTTTCAGCTT    GACACAGGTT       360

TGGAGTATGC    AAACAGCTAT    AATTTTGCAA    AAAAGGAAAA    TAACTCTCCT    GAACATCTAA       420

AAGATGAAGT    TTCTATCATC    CAAAGTATGG    GCTACAGAAA    CCGTGCCAAA    AGACTTCTAC       480

AGAGTGAACC    CGAAAATCCT    TCCTTGCAGG    AAACCAGTCT    CAGTGTCCAA    CTCTCTAACC       540

TTGGAACTGT    GAGAACTCTG    AGGACAAAGC    AGCGGATACA    ACCTCAAAAG    ACGTCTGTCT       600

ACATTGAATT    GGGATCTGAT    TCTTCTGAAG    ATACCGTTAA    TAAGGCAACT    TATTGCAGTG       660

TGGGAGATCA    AGAATTGTTA    CAAATCACCC    CTCAAGGAAC    CAGGGATGAA    ATCAGTTTGG       720

ATTCTGCAAA    AAAGGCTGCT    TGTGAATTTT    CTGAGACGGA    TGTAACAAAT    ACTGAACATC       780
```

```
ATCAACCCAG  TAATAATGAT  TTGAACACCA  CTGAGAAGCG  TGCAGCTGAG  AGGCATCCAG    840

AAAAGTATCA  GGGTAGTTCT  GTTTCAAACT  TGCATGTGGA  GCCATGTGGC  ACAAATACTC    900

ATGCCAGCTC  ATTACAGCAT  GAGAACAGCA  GTTTATTACT  CACTAAAGAC  AGAATGAATG    960

TAGAAAAGGC  TGAATTCTGT  AATAAAAGCA  AACAGCCTGG  CTTAGCAAGG  AGCCAACATA   1020

ACAGATGGGC  TGGAAGTAAG  GAAACATGTA  ATGATAGGCG  GACTCCCAGC  ACAGAAAAAA   1080

AGGTAGATCT  GAATGCTGAT  CCCCTGTGTG  AGAGAAAAGA  ATGGAATAAG  CAGAAACTGC   1140

CATGCTCAGA  GAATCCTAGA  GATACTGAAG  ATGTTCCTTG  GATAACACTA  AATAGCAGCA   1200

TTCAGAAAGT  TAATGAGTGG  TTTTCCAGAA  GTGATGAACT  GTTAGGTTCT  GATGACTCAC   1260

ATGATGGGA   GTCTGAATCA  AATGCCAAAG  TAGCTGATGT  ATTGGACGTT  CTAAATGAGG   1320

TAGATGAATA  TTCTGGTTCT  TCAGAGAAAA  TAGACTTACT  GGCCAGTGAT  CCTCATGAGG   1380

CTTTAATATG  TAAAAGTGAA  AGAGTTCACT  CCAAATCAGT  AGAGAGTAAT  ATTGAAGACA   1440

AAATATTTGG  GAAAACCTAT  CGGAAGAAGG  CAAGCCTCCC  CAACTTAAGC  CATGTAACTG   1500

AAAATCTAAT  TATAGGAGCA  TTTGTTACTG  AGCCACAGAT  AATACAAGAG  CGTCCCCTCA   1560

CAAATAAATT  AAAGCGTAAA  AGGAGACCTA  CATCAGGCCT  TCATCCTGAG  GATTTTATCA   1620

AGAAAGCAGA  TTTGGCAGTT  CAAAAGACTC  CTGAAATGAT  AAATCAGGGA  ACTAACCAAA   1680

CGGAGCAGAA  TGGTCAAGTG  ATGAATATTA  CTAATAGTGG  TCATGAGAAT  AAAACAAAAG   1740

GTGATTCTAT  TCAGAATGAG  AAAAATCCTA  ACCCAATAGA  ATCACTCGAA  AAAGAATCTG   1800

CTTTCAAAAC  GAAAGCTGAA  CCTATAAGCA  GCAGTATAAG  CAATATGGAA  CTCGAATTAA   1860

ATATCCACAA  TTCAAAAGCA  CCTAAAAAGA  ATAGGCTGAG  GAGGAAGTCT  TCTACCAGGC   1920

ATATTCATGC  GCTTGAACTA  GTAGTCAGTA  GAAATCTAAG  CCCACCTAAT  TGTACTGAAT   1980

TGCAAATTGA  TAGTTGTTCT  AGCAGTGAAG  AGATAAAGAA  AAAAAAGTAC  AACCAAATGC   2040

CAGTCAGGCA  CAGCAGAAAC  CTACAACTCA  TGGAAGGTAA  AGAACCTGCA  ACTGGAGCCA   2100

AGAAGAGTAA  CAAGCCAAAT  GAACAGACAA  GTAAAAGACA  TGACAGCGAT  ACTTTCCCAG   2160

AGCTGAAGTT  AACAAATGCA  CCTGGTTCTT  TTACTAAGTG  TTCAAATACC  AGTGAACTTA   2220

AAGAATTTGT  CAATCCTAGC  CTTCCAAGAG  AAGAAAAAGA  AGAGAAACTA  GAAACAGTTA   2280

AAGTGTCTAA  TAATGCTGAA  GACCCCAAAG  ATCTCATGTT  AAGTGGAGAA  AGGGTTTTGC   2340

AAACTGAAAG  ATCTGTAGAG  AGTAGCAGTA  TTTCATTGGT  ACCTGGTACT  GATTATGGCA   2400

CTCAGGAAAG  TATCTCGTTA  CTGGAAGTTA  GCACTCTAGG  GAAGGCAAAA  ACAGAACCAA   2460

ATAAATGTGT  GAGTCAGTGT  GCAGCATTTG  AAAACCCCAA  GGGACTAATT  CATGGTTGTT   2520

CCAAAGATAA  TAGAAATGAC  ACAGAAGGCT  TTAAGTATCC  ATTGGGACAT  GAAGTTAACC   2580

ACAGTCGGGA  AACAAGCATA  GAAATGGAAG  AAAGTGAACT  TGATGCTCAG  TATTTGCAGA   2640

ATACATTCAA  GGTTTCAAAG  CGCCAGTCAT  TTGCTCCGTT  TTCAAATCCA  GGAAATGCAG   2700

AAGAGGAATG  TGCAACATTC  TCTGCCCACT  CTGGGTCCTT  AAAGAAACAA  AGTCCAAAAG   2760

TCACTTTTGA  ATGTGAACAA  AAGGAAGAAA  ATCAAGGAAA  GAATGAGTCT  AATATCAAGC   2820

CTGTACAGAC  AGTTAATATC  ACTGCAGGCT  TTCCTGTGGT  TGGTCAGAAA  GATAAGCCAG   2880

TTGATAATGC  CAAATGTAGT  ATCAAAGGAG  GCTCTAGGTT  TTGTCTATCA  TCTCAGTTCA   2940

GAGGCAACGA  AACTGGACTC  ATTACTCCAA  ATAAACATGG  ACTTTTACAA  AACCCATATC   3000

GTATACCACC  ACTTTTTCCC  ATCAAGTCAT  TTGTTAAAAC  TAAATGTAAG  AAAAATCTGC   3060

TAGAGGAAAA  CTTTGAGGAA  CATTCAATGT  CACCTGAAAG  AGAAATGGGA  AATGAGAACA   3120

TTCCAAGTAC  AGTGAGCACA  ATTAGCCGTA  ATAACATTAG  AGAAAATGTT  TTTAAAGAAG   3180
```

```
CCAGCTCAAG  CAATATTAAT  GAAGTAGGTT  CCAGTACTAA  TGAAGTGGGC  TCCAGTATTA  3240
ATGAAATAGG  TTCCAGTGAT  GAAAACATTC  AAGCAGAACT  AGGTAGAAAC  AGAGGGCCAA  3300
AATTGAATGC  TATGCTTAGA  TTAGGGGTTT  TGCAACCTGA  GGTCTATAAA  CAAAGTCTTC  3360
CTGGAAGTAA  TTGTAAGCAT  CCTGAAATAA  AAAAGCAAGA  ATATGAAGAA  GTAGTTCAGA  3420
CTGTTAATAC  AGATTTCTCT  CCATATCTGA  TTTCAGATAA  CTTAGAACAG  CCTATGGGAA  3480
GTAGTCATGC  ATCTCAGGTT  TGTTCTGAGA  CACCTGATGA  CCTGTTAGAT  GATGGTGAAA  3540
TAAAGGAAGA  TACTAGTTTT  GCTGAAAATG  ACATTAAGGA  AAGTTCTGCT  GTTTTAGCA   3600
AAAGCGTCCA  GAAAGGAGAG  CTTAGCAGGA  GTCCTAGCCC  TTTCACCCAT  ACACATTTGG  3660
CTCAGGGTTA  CCGAAGAGGG  GCCAAGAAAT  TAGAGTCCTC  AGAAGAGAAC  TTATCTAGTG  3720
AGGATGAAGA  GCTTCCCTGC  TTCCAACACT  TGTTATTTGG  TAAAGTAAAC  AATATACCTT  3780
CTCAGTCTAC  TAGGCATAGC  ACCGTTGCTA  CCGAGTGTCT  GTCTAAGAAC  ACAGAGGAGA  3840
ATTTATTATC  ATTGAAGAAT  AGCTTAAATG  ACTGCAGTAA  CCAGGTAATA  TTGGCAAAGG  3900
CATCTCAGGA  ACATCACCTT  AGTGAGGAAA  CAAAATGTTC  TGCTAGCTTG  TTTTCTTCAC  3960
AGTGCAGTGA  ATTGGAAGAC  TTGACTGCAA  ATACAAACAC  CCAGGATCCT  TTCTTGATTG  4020
GTTCTTCCAA  ACAAATGAGG  CATCAGTCTG  AAAGCCAGGG  AGTTGGTCTG  AGTGACAAGG  4080
AATTGGTTTC  AGATGATGAA  GAAAGAGGAA  CGGGCTTGGA  AGAAAATAAT  CAAGAAGAGC  4140
AAAGCATGGA  TTCAAACTTA  GGTGAAGCAG  CATCTGGGTG  TGAGAGTGAA  ACAAGCGTCT  4200
CTGAAGACTG  CTCAGGGCTA  TCCTCTCAGA  GTGACATTTT  AACCACTCAG  CAGAGGGATA  4260
CCATGCAACA  TAACCTGATA  AAGCTCCAGC  AGGAAATGGC  TGAACTAGAA  GCTGTGTTAG  4320
AACAGCATGG  GAGCCAGCCT  TCTAACAGCT  ACCCTTCCAT  CATAAGTGAC  TCTTCTGCCC  4380
TTGAGGACCT  GCGAAATCCA  GAACAAAGCA  CATCAGAAAA  AGCAGTATTA  ACTTCACAGA  4440
AAAGTAGTGA  ATACCCTATA  AGCCAGAATC  CAGAAGGCCT  TTCTGCTGAC  AAGTTTGAGG  4500
TGTCTGCAGA  TAGTTCTACC  AGTAAAAATA  AGAACCAGG   AGTGGAAAGG  TCATCCCCTT  4560
CTAAATGCCC  ATCATTAGAT  GATAGGTGGT  ACATGCACAG  TTGCTCTGGG  AGTCTTCAGA  4620
ATAGAAACTA  CCCATCTCAA  GAGGAGCTCA  TTAAGGTTGT  TGATGTGGAG  GAGCAACAGC  4680
TGGAAGAGTC  TGGGCCACAC  GATTTGACGG  AAACATCTTA  CTTGCCAAGG  CAAGATCTAG  4740
AGGGAACCCC  TTACCTGGAA  TCTGGAATCA  GCCTCTTCTC  TGATGACCCT  GAATCTGATC  4800
CTTCTGAAGA  CAGAGCCCCA  GAGTCAGCTC  GTGTTGGCAA  CATACCATCT  TCAACCTCTG  4860
CATTGAAAGT  TCCCCAATTG  AAAGTTGCAG  AATCTGCCCA  GAGTCCAGCT  GCTGCTCATA  4920
CTACTGATAC  TGCTGGGTAT  AATGCAATGG  AAGAAAGTGT  GAGCAGGGAG  AAGCCAGAAT  4980
TGACAGCTTC  AACAGAAAGG  GTCAACAAAA  GAATGTCCAT  GGTGGTGTCT  GGCCTGACCC  5040
CAGAAGAATT  TATGCTCGTG  TACAAGTTTG  CCAGAAAACA  CCACATCACT  TTAACTAATC  5100
TAATTACTGA  AGAGACTACT  CATGTTGTTA  TGAAAACAGA  TGCTGAGTTT  GTGTGTGAAC  5160
GGACACTGAA  ATATTTTCTA  GGAATTGCGG  GAGGAAAATG  GGTAGTTAGC  TATTTCTGGG  5220
TGACCCAGTC  TATTAAAGAA  AGAAAAATGC  TGAATGAGCA  TGATTTTGAA  GTCAGAGGAG  5280
ATGTGGTCAA  TGGAAGAAAC  CACCAAGGTC  CAAAGCGAGC  AAGAGAATCC  CAGGACAGAA  5340
AGATCTTCAG  GGGGCTAGAA  ATCTGTTGCT  ATGGGCCCTT  CACCAACATG  CCCACAGATC  5400
AACTGGAATG  GATGGTACAG  CTGTGTGGTG  CTTCTGTGGT  GAAGGAGCTT  TCATCATTCA  5460
CCCTTGGCAC  AGGTGTCCAC  CCAATTGTGG  TTGTGCAGCC  AGATGCCTGG  ACAGAGGACA  5520
ATGGCTTCCA  TGCAATTGGG  CAGATGTGTG  AGGCACCTGT  GGTGACCCGA  GAGTGGGTGT  5580
```

-continued

| | | | | | |
|---|---|---|---|---|---|
| TGGACAGTGT | AGCACTCTAC | CAGTGCCAGG | AGCTGGACAC | CTACCTGATA | CCCCAGATCC | 5640 |
| CCCACAGCCA | CTACTG | | | | | 5656 |

( 2 ) INFORMATION FOR SEQ ID NO:2:

( i ) SEQUENCE CHARACTERISTICS:
        ( A ) LENGTH: 5709 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | GTGTGACCAC | 240 |
| ATATTTTGCA | AATTTTGCAT | GCTGAAACTT | CTCAACCAGA | AGAAAGGGCC | TTCACAGTGT | 300 |
| CCTTTATGTA | AGAATGATAT | AACCAAAAGG | AGCCTACAAG | AAAGTACGAG | ATTTAGTCAA | 360 |
| CTTGTTGAAG | AGCTATTGAA | AATCATTTGT | GCTTTTCAGC | TTGACACAGG | TTTGGAGTAT | 420 |
| GCAAACAGCT | ATAATTTTGC | AAAAAAGGAA | AATAACTCTC | CTGAACATCT | AAAAGATGAA | 480 |
| GTTTCTATCA | TCCAAAGTAT | GGGCTACAGA | AACCGTGCCA | AAAGACTTCT | ACAGAGTGAA | 540 |
| CCCGAAAATC | CTTCCTTGCA | GGAAACCAGT | CTCAGTGTCC | AACTCTCTAA | CCTTGGAACT | 600 |
| GTGAGAACTC | TGAGGACAAA | GCAGCGGATA | CAACCTCAAA | AGACGTCTGT | CTACATTGAA | 660 |
| TTGGGATCTG | ATTCTTCTGA | AGATACCGTT | AATAAGGCAA | CTTATTGCAG | TGTGGGAGAT | 720 |
| CAAGAATTGT | TACAAATCAC | CCCTCAAGGA | ACCAGGGATG | AAATCAGTTT | GGATTCTGCA | 780 |
| AAAAAGGCTG | CTTGTGAATT | TTCTGAGACG | GATGTAACAA | ATACTGAACA | TCATCAACCC | 840 |
| AGTAATAATG | ATTTGAACAC | CACTGAGAAG | CGTGCAGCTG | AGAGGCATCC | AGAAAAGTAT | 900 |
| CAGGGTAGTT | CTGTTTCAAA | CTTGCATGTG | GAGCCATGTG | GCACAAATAC | TCATGCCAGC | 960 |
| TCATTACAGC | ATGAGAACAG | CAGTTTATTA | CTCACTAAAG | ACAGAATGAA | TGTAGAAAAG | 1020 |
| GCTGAATTCT | GTAATAAAAG | CAAACAGCCT | GGCTTAGCAA | GGAGCCAACA | TAACAGATGG | 1080 |
| GCTGGAAGTA | AGGAAACATG | TAATGATAGG | CGGACTCCCA | GCACAGAAAA | AAAGGTAGAT | 1140 |
| CTGAATGCTG | ATCCCCTGTG | TGAGAGAAAA | GAATGGAATA | AGCAGAAACT | GCCATGCTCA | 1200 |
| GAGAATCCTA | GAGATACTGA | AGATGTTCCT | TGGATAACAC | TAAATAGCAG | CATTCAGAAA | 1260 |
| GTTAATGAGT | GGTTTTCCAG | AAGTGATGAA | CTGTTAGGTT | CTGATGACTC | ACATGATGGG | 1320 |
| GAGTCTGAAT | CAAATGCCAA | AGTAGCTGAT | GTATTGGACG | TTCTAAATGA | GGTAGATGAA | 1380 |
| TATTCTGGTT | CTTCAGAGAA | AATAGACTTA | CTGGCCAGTG | ATCCTCATGA | GGCTTTAATA | 1440 |
| TGTAAAAGTG | AAAGAGTTCA | CTCCAAATCA | GTAGAGAGTA | ATATTGAAGA | CAAATATTT | 1500 |
| GGGAAAACCT | ATCGGAAGAA | GGCAAGCCTC | CCCAACTTAA | GCCATGTAAC | TGAAAATCTA | 1560 |
| ATTATAGGAG | CATTTGTTAC | TGAGCCACAG | ATAATACAAG | AGCGTCCCCT | CACAAATAAA | 1620 |
| TTAAAGCGTA | AAAGGAGACC | TACATCAGGC | CTTCATCCTG | AGGATTTTAT | CAAGAAAGCA | 1680 |
| GATTTGGCAG | TTCAAAAGAC | TCCTGAAATG | ATAAATCAGG | GAACTAACCA | AACGGAGCAG | 1740 |
| AATGGTCAAG | TGATGAATAT | TACTAATAGT | GGTCATGAGA | ATAAAACAAA | AGGTGATTCT | 1800 |
| ATTCAGAATG | AGAAAAATCC | TAACCCAATA | GAATCACTCG | AAAAGAATC | TGCTTTCAAA | 1860 |

| | | | | | | |
|---|---|---|---|---|---|---|
| ACGAAAGCTG | AACCTATAAG | CAGCAGTATA | AGCAATATGG | AACTCGAATT | AAATATCCAC | 1920 |
| AATTCAAAAG | CACCTAAAAA | GAATAGGCTG | AGGAGGAAGT | CTTCTACCAG | GCATATTCAT | 1980 |
| GCGCTTGAAC | TAGTAGTCAG | TAGAAATCTA | AGCCCACCTA | ATTGTACTGA | ATTGCAAATT | 2040 |
| GATAGTTGTT | CTAGCAGTGA | AGAGATAAAG | AAAAAAAGT | ACAACCAAAT | GCCAGTCAGG | 2100 |
| CACAGCAGAA | ACCTACAACT | CATGGAAGGT | AAAGAACCTG | CAACTGGAGC | CAAGAAGAGT | 2160 |
| AACAAGCCAA | ATGAACAGAC | AAGTAAAAGA | CATGACAGCG | ATACTTTCCC | AGAGCTGAAG | 2220 |
| TTAACAAATG | CACCTGGTTC | TTTTACTAAG | TGTTCAAATA | CCAGTGAACT | TAAAGAATTT | 2280 |
| GTCAATCCTA | GCCTTCCAAG | AGAAGAAAAA | GAAGAGAAAC | TAGAAACAGT | TAAAGTGTCT | 2340 |
| AATAATGCTG | AAGACCCCAA | AGATCTCATG | TTAAGTGGAG | AAAGGGTTTT | GCAAACTGAA | 2400 |
| AGATCTGTAG | AGAGTAGCAG | TATTTCATTG | GTACCTGGTA | CTGATTATGG | CACTCAGGAA | 2460 |
| AGTATCTCGT | TACTGGAAGT | TAGCACTCTA | GGGAAGGCAA | AAACAGAACC | AAATAAATGT | 2520 |
| GTGAGTCAGT | GTGCAGCATT | TGAAAACCCC | AAGGGACTAA | TTCATGGTTG | TTCCAAAGAT | 2580 |
| AATAGAAATG | ACACAGAAGG | CTTTAAGTAT | CCATTGGGAC | ATGAAGTTAA | CCACAGTCGG | 2640 |
| GAAACAAGCA | TAGAAATGGA | AGAAAGTGAA | CTTGATGCTC | AGTATTTGCA | GAATACATTC | 2700 |
| AAGGTTTCAA | AGCGCCAGTC | ATTTGCTCCG | TTTTCAAATC | CAGGAAATGC | AGAAGAGGAA | 2760 |
| TGTGCAACAT | TCTCTGCCCA | CTCTGGGTCC | TTAAAGAAAC | AAAGTCCAAA | AGTCACTTTT | 2820 |
| GAATGTGAAC | AAAAGGAAGA | AAATCAAGGA | AAGAATGAGT | CTAATATCAA | GCCTGTACAG | 2880 |
| ACAGTTAATA | TCACTGCAGG | CTTTCCTGTG | GTTGGTCAGA | AAGATAAGCC | AGTTGATAAT | 2940 |
| GCCAAATGTA | GTATCAAAGG | AGGCTCTAGG | TTTTGTCTAT | CATCTCAGTT | CAGAGGCAAC | 3000 |
| GAAACTGGAC | TCATTACTCC | AAATAAACAT | GGACTTTTAC | AAAACCCATA | TCGTATACCA | 3060 |
| CCACTTTTTC | CCATCAAGTC | ATTTGTTAAA | ACTAAATGTA | AGAAAAATCT | GCTAGAGGAA | 3120 |
| AACTTTGAGG | AACATTCAAT | GTCACCTGAA | AGAGAAATGG | GAAATGAGAA | CATTCCAAGT | 3180 |
| ACAGTGAGCA | CAATTAGCCG | TAATAACATT | AGAGAAAATG | TTTTTAAAGA | AGCCAGCTCA | 3240 |
| AGCAATATTA | ATGAAGTAGG | TTCCAGTACT | AATGAAGTGG | GCTCCAGTAT | TAATGAAATA | 3300 |
| GGTTCCAGTG | ATGAAAACAT | TCAAGCAGAA | CTAGGTAGAA | ACAGAGGGCC | AAAATTGAAT | 3360 |
| GCTATGCTTA | GATTAGGGGT | TTTGCAACCT | GAGGTCTATA | AACAAAGTCT | TCCTGGAAGT | 3420 |
| AATTGTAAGC | ATCCTGAAAT | AAAAAAGCAA | GAATATGAAG | AAGTAGTTCA | GACTGTTAAT | 3480 |
| ACAGATTTCT | CTCCATATCT | GATTTCAGAT | AACTTAGAAC | AGCCTATGGG | AAGTAGTCAT | 3540 |
| GCATCTCAGG | TTTGTTCTGA | GACACCTGAT | GACCTGTTAG | ATGATGGTGA | AATAAAGGAA | 3600 |
| GATACTAGTT | TTGCTGAAAA | TGACATTAAG | GAAAGTTCTG | CTGTTTTTAG | CAAAAGCGTC | 3660 |
| CAGAAAGGAG | AGCTTAGCAG | GAGTCCTAGC | CCTTTCACCC | ATACACATTT | GGCTCAGGGT | 3720 |
| TACCGAAGAG | GGGCCAAGAA | ATTAGAGTCC | TCAGAAGAGA | ACTTATCTAG | TGAGGATGAA | 3780 |
| GAGCTTCCCT | GCTTCCAACA | CTTGTTATTT | GGTAAAGTAA | ACAATATACC | TTCTCAGTCT | 3840 |
| ACTAGGCATA | GCACCGTTGC | TACCGAGTGT | CTGTCTAAGA | ACACAGAGGA | GAATTTATTA | 3900 |
| TCATTGAAGA | ATAGCTTAAA | TGACTGCAGT | AACCAGGTAA | TATTGGCAAA | GGCATCTCAG | 3960 |
| GAACATCACC | TTAGTGAGGA | AACAAAATGT | TCTGCTAGCT | TGTTTTCTTC | ACAGTGCAGT | 4020 |
| GAATTGGAAG | ACTTGACTGC | AAATACAAAC | ACCCAGGATC | CTTTCTTGAT | TGGTTCTTCC | 4080 |
| AAACAAATGA | GGCATCAGTC | TGAAAGCCAG | GGAGTTGGTC | TGAGTGACAA | GGAATTGGTT | 4140 |
| TCAGATGATG | AAGAAAGAGG | AACGGGCTTG | GAAGAAAATA | ATCAAGAAGA | GCAAAGCATG | 4200 |
| GATTCAAACT | TAGGTGAAGC | AGCATCTGGG | TGTGAGAGTG | AAACAAGCGT | CTCTGAAGAC | 4260 |

| | | | | | | |
|---|---|---|---|---|---|---|
| TGCTCAGGGC | TATCCTCTCA | GAGTGACATT | TTAACCACTC | AGCAGAGGGA | TACCATGCAA | 4320 |
| CATAACCTGA | TAAAGCTCCA | GCAGGAAATG | GCTGAACTAG | AAGCTGTGTT | AGAACAGCAT | 4380 |
| GGGAGCCAGC | CTTCTAACAG | CTACCTTCC | ATCATAAGTG | ACTCTTCTGC | CCTTGAGGAC | 4440 |
| CTGCGAAATC | CAGAACAAAG | CACATCAGAA | AAAGCAGTAT | TAACTTCACA | GAAAAGTAGT | 4500 |
| GAATACCCTA | TAAGCCAGAA | TCCAGAAGGC | CTTTCTGCTG | ACAAGTTTGA | GGTGTCTGCA | 4560 |
| GATAGTTCTA | CCAGTAAAAA | TAAAGAACCA | GGAGTGGAAA | GGTCATCCCC | TTCTAAATGC | 4620 |
| CCATCATTAG | ATGATAGGTG | GTACATGCAC | AGTTGCTCTG | GGAGTCTTCA | GAATAGAAAC | 4680 |
| TACCCATCTC | AAGAGGAGCT | CATTAAGGTT | GTTGATGTGG | AGGAGCAACA | GCTGGAAGAG | 4740 |
| TCTGGGCCAC | ACGATTTGAC | GGAAACATCT | TACTTGCCAA | GGCAAGATCT | AGAGGGAACC | 4800 |
| CCTTACCTGG | AATCTGGAAT | CAGCCTCTTC | TCTGATGACC | CTGAATCTGA | TCCTTCTGAA | 4860 |
| GACAGAGCCC | CAGAGTCAGC | TCGTGTTGGC | AACATACCAT | CTTCAACCTC | TGCATTGAAA | 4920 |
| GTTCCCCAAT | TGAAAGTTGC | AGAATCTGCC | CAGAGTCCAG | CTGCTGCTCA | TACTACTGAT | 4980 |
| ACTGCTGGGT | ATAATGCAAT | GGAAGAAAGT | GTGAGCAGGG | AGAAGCCAGA | ATTGACAGCT | 5040 |
| TCAACAGAAA | GGGTCAACAA | AAGAATGTCC | ATGGTGGTGT | CTGGCCTGAC | CCCAGAAGAA | 5100 |
| TTTATGCTCG | TGTACAAGTT | TGCCAGAAAA | CACCACATCA | CTTTAACTAA | TCTAATTACT | 5160 |
| GAAGAGACTA | CTCATGTTGT | TATGAAAACA | GATGCTGAGT | TTGTGTGTGA | ACGGACACTG | 5220 |
| AAATATTTTC | TAGGAATTGC | GGGAGGAAAA | TGGGTAGTTA | GCTATTTCTG | GGTGACCCAG | 5280 |
| TCTATTAAAG | AAAGAAAAAT | GCTGAATGAG | CATGATTTTG | AAGTCAGAGG | AGATGTGGTC | 5340 |
| AATGGAAGAA | ACCACCAAGG | TCCAAAGCGA | GCAAGAGAAT | CCCAGGACAG | AAAGATCTTC | 5400 |
| AGGGGCTAG | AAATCTGTTG | CTATGGGCCC | TTCACCAACA | TGCCCACAGA | TCAACTGGAA | 5460 |
| TGGATGGTAC | AGCTGTGTGG | TGCTTCTGTG | GTGAAGGAGC | TTTCATCATT | CACCCTTGGC | 5520 |
| ACAGGTGTCC | ACCCAATTGT | GGTTGTGCAG | CCAGATGCCT | GGACAGAGGA | CAATGGCTTC | 5580 |
| CATGCAATTG | GGCAGATGTG | TGAGGCACCT | GTGGTGACCC | GAGAGTGGGT | GTTGGACAGT | 5640 |
| GTAGCACTCT | ACCAGTGCCA | GGAGCTGGAC | ACCTACCTGA | TACCCCAGAT | CCCCCACAGC | 5700 |
| CACTACTGA | | | | | | 5709 |

( 2 ) INFORMATION FOR SEQ ID NO:3:

( i ) SEQUENCE CHARACTERISTICS:
        ( A ) LENGTH: 5689 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAAGGG | CCTTCACAGT | 300 |
| GTCCTTTATG | AGCCTACAAG | AAAGTACGAG | ATTTAGTCAA | CTTGTTGAAG | AGCTATTGAA | 360 |
| AATCATTTGT | GCTTTTCAGC | TTGACACAGG | TTTGGAGTAT | GCAAACAGCT | ATAATTTTGC | 420 |
| AAAAAAGGAA | AATAACTCTC | CTGAACATCT | AAAAGATGAA | GTTTCTATCA | TCCAAAGTAT | 480 |
| GGGCTACAGA | AACCGTGCCA | AAAGACTTCT | ACAGAGTGAA | CCCGAAAATC | CTTCCTTGCA | 540 |

```
GGAAACCAGT CTCAGTGTCC AACTCTCTAA CCTTGGAACT GTGAGAACTC TGAGGACAAA      600
GCAGCGGATA CAACCTCAAA AGACGTCTGT CTACATTGAA TTGGGATCTG ATTCTTCTGA      660
AGATACCGTT AATAAGGCAA CTTATTGCAG TGTGGGAGAT CAAGAATTGT TACAAATCAC      720
CCCTCAAGGA ACCAGGGATG AAATCAGTTT GGATTCTGCA AAAAAGGCTG CTTGTGAATT      780
TTCTGAGACG GATGTAACAA ATACTGAACA TCATCAACCC AGTAATAATG ATTTGAACAC      840
CACTGAGAAG CGTGCAGCTG AGAGGCATCC AGAAAAGTAT CAGGGTAGTT CTGTTTCAAA      900
CTTGCATGTG GAGCCATGTG GCACAAATAC TCATGCCAGC TCATTACAGC ATGAGAACAG      960
CAGTTTATTA CTCACTAAAG ACAGAATGAA TGTAGAAAAG GCTGAATTCT GTAATAAAAG     1020
CAAACAGCCT GGCTTAGCAA GGAGCCAACA TAACAGATGG GCTGGAAGTA AGGAAACATG     1080
TAATGATAGG CGGACTCCCA GCACAGAAAA AAAGGTAGAT CTGAATGCTG ATCCCCTGTG     1140
TGAGAGAAAA GAATGGAATA AGCAGAAACT GCCATGCTCA GAGAATCCTA GAGATACTGA     1200
AGATGTTCCT TGGATAACAC TAAATAGCAG CATTCAGAAA GTTAATGAGT GGTTTTCCAG     1260
AAGTGATGAA CTGTTAGGTT CTGATGACTC ACATGATGGG GAGTCTGAAT CAAATGCCAA     1320
AGTAGCTGAT GTATTGGACG TTCTAAATGA GGTAGATGAA TATTCTGGTT CTTCAGAGAA     1380
AATAGACTTA CTGGCCAGTG ATCCTCATGA GGCTTTAATA TGTAAAAGTG AAAGAGTTCA     1440
CTCCAAATCA GTAGAGAGTA ATATTGAAGA CAAAATATTT GGGAAAACCT ATCGGAAGAA     1500
GGCAAGCCTC CCCAACTTAA GCCATGTAAC TGAAAATCTA ATTATAGGAG CATTTGTTAC     1560
TGAGCCACAG ATAATACAAG AGCGTCCCCT CACAAATAAA TTAAAGCGTA AAAGGAGACC     1620
TACATCAGGC CTTCATCCTG AGGATTTTAT CAAGAAAGCA GATTTGGCAG TTCAAAAGAC     1680
TCCTGAAATG ATAAATCAGG GAACTAACCA AACGGAGCAG AATGGTCAAG TGATGAATAT     1740
TACTAATAGT GGTCATGAGA ATAAACAAA AGGTGATTCT ATTCAGAATG AGAAAAATCC     1800
TAACCCAATA GAATCACTCG AAAAAGAATC TGCTTTCAAA ACGAAGCTG AACCTATAAG      1860
CAGCAGTATA AGCAATATGG AACTCGAATT AAATATCCAC AATTCAAAAG CACCTAAAAA     1920
GAATAGGCTG AGGAGGAAGT CTTCTACCAG GCATATTCAT GCGCTTGAAC TAGTAGTCAG     1980
TAGAAATCTA AGCCCACCTA ATTGTACTGA ATTGCAAATT GATAGTTGTT CTAGCAGTGA     2040
AGAGATAAAG AAAAAAAGT ACAACCAAAT GCCAGTCAGG CACAGCAGAA ACCTACAACT      2100
CATGGAAGGT AAAGAACCTG CAACTGGAGC CAAGAAGAGT AACAAGCCAA ATGAACAGAC     2160
AAGTAAAAGA CATGACAGCG ATACTTTCCC AGAGCTGAAG TTAACAAATG CACCTGGTTC     2220
TTTTACTAAG TGTTCAAATA CCAGTGAACT TAAAGAATTT GTCAATCCTA GCCTTCCAAG     2280
AGAAGAAAAA GAAGAGAAAC TAGAAACAGT TAAAGTGTCT AATAATGCTG AAGACCCCAA     2340
AGATCTCATG TTAAGTGGAG AAAGGGTTTT GCAAACTGAA AGATCTGTAG AGAGTAGCAG     2400
TATTTCATTG GTACCTGGTA CTGATTATGG CACTCAGGAA AGTATCTCGT TACTGGAAGT     2460
TAGCACTCTA GGGAAGGCAA AAACAGAACC AAATAAATGT GTGAGTCAGT GTGCAGCATT     2520
TGAAAACCCC AAGGGACTAA TTCATGGTTG TTCCAAAGAT AATAGAAATG ACACAGAAGG     2580
CTTTAAGTAT CCATTGGGAC ATGAAGTTAA CCACAGTCGG GAAACAAGCA TAGAAATGGA     2640
AGAAAGTGAA CTTGATGCTC AGTATTTGCA GAATACATTC AAGGTTTCAA AGCGCCAGTC     2700
ATTTGCTCCG TTTTCAAATC CAGGAAATGC AGAAGAGGAA TGTGCAACAT TCTCTGCCCA     2760
CTCTGGGTCC TTAAAGAAAC AAAGTCCAAA AGTCACTTTT GAATGTGAAC AAAAGGAAGA     2820
AAATCAAGGA AAGAATGAGT CTAATATCAA GCCTGTACAG ACAGTTAATA TCACTGCAGG     2880
CTTTCCTGTG GTTGGTCAGA AAGATAAGCC AGTTGATAAT GCCAAATGTA GTATCAAAGG     2940
```

```
AGGCTCTAGG TTTTGTCTAT CATCTCAGTT CAGAGGCAAC GAAACTGGAC TCATTACTCC    3000
AAATAAACAT GGACTTTTAC AAAACCCATA TCGTATACCA CCACTTTTTC CCATCAAGTC    3060
ATTTGTTAAA ACTAAATGTA AGAAAAATCT GCTAGAGGAA AACTTTGAGG AACATTCAAT    3120
GTCACCTGAA AGAGAAATGG GAAATGAGAA CATTCCAAGT ACAGTGAGCA CAATTAGCCG    3180
TAATAACATT AGAGAAAATG TTTTTAAAGA AGCCAGCTCA AGCAATATTA ATGAAGTAGG    3240
TTCCAGTACT AATGAAGTGG GCTCCAGTAT TAATGAAATA GGTTCCAGTG ATGAAAACAT    3300
TCAAGCAGAA CTAGGTAGAA ACAGAGGGCC AAAATTGAAT GCTATGCTTA GATTAGGGGT    3360
TTTGCAACCT GAGGTCTATA AACAAAGTCT TCCTGGAAGT AATTGTAAGC ATCCTGAAAT    3420
AAAAAGCAA GAATATGAAG AAGTAGTTCA GACTGTTAAT ACAGATTTCT CTCCATATCT    3480
GATTTCAGAT AACTTAGAAC AGCCTATGGG AAGTAGTCAT GCATCTCAGG TTTGTTCTGA    3540
GACACCTGAT GACCTGTTAG ATGATGGTGA AATAAAGGAA GATACTAGTT TTGCTGAAAA    3600
TGACATTAAG GAAAGTTCTG CTGTTTTTAG CAAAAGCGTC CAGAAAGGAG AGCTTAGCAG    3660
GAGTCCTAGC CCTTTCACCC ATACACATTT GGCTCAGGGT TACCGAAGAG GGGCCAAGAA    3720
ATTAGAGTCC TCAGAAGAGA ACTTATCTAG TGAGGATGAA GAGCTTCCCT GCTTCCAACA    3780
CTTGTTATTT GGTAAAGTAA ACAATATACC TTCTCAGTCT ACTAGGCATA GCACCGTTGC    3840
TACCGAGTGT CTGTCTAAGA ACACAGAGGA GAATTTATTA TCATTGAAGA ATAGCTTAAA    3900
TGACTGCAGT AACCAGGTAA TATTGGCAAA GGCATCTCAG GAACATCACC TTAGTGAGGA    3960
AACAAAATGT TCTGCTAGCT TGTTTTCTTC ACAGTGCAGT GAATTGGAAG ACTTGACTGC    4020
AAATACAAAC ACCCAGGATC CTTTCTTGAT TGGTTCTTCC AAACAAATGA GGCATCAGTC    4080
TGAAAGCCAG GGAGTTGGTC TGAGTGACAA GGAATTGGTT TCAGATGATG AAGAAAGAGG    4140
AACGGGCTTG GAAGAAAATA ATCAAGAAGA GCAAAGCATG GATTCAAACT TAGGTGAAGC    4200
AGCATCTGGG TGTGAGAGTG AAACAAGCGT CTCTGAAGAC TGCTCAGGGC TATCCTCTCA    4260
GAGTGACATT TTAACCACTC AGCAGAGGGA TACCATGCAA CATAACCTGA TAAAGCTCCA    4320
GCAGGAAATG GCTGAACTAG AAGCTGTGTT AGAACAGCAT GGGAGCCAGC CTTCTAACAG    4380
CTACCCTTCC ATCATAAGTG ACTCTTCTGC CCTTGAGGAC CTGCGAAATC CAGAACAAAG    4440
CACATCAGAA AAAGCAGTAT TAACTTCACA GAAAAGTAGT GAATACCCTA TAAGCCAGAA    4500
TCCAGAAGGC CTTTCTGCTG ACAAGTTTGA GGTGTCTGCA GATAGTTCTA CCAGTAAAAA    4560
TAAAGAACCA GGAGTGGAAA GGTCATCCCC TTCTAAATGC CCATCATTAG ATGATAGGTG    4620
GTACATGCAC AGTTGCTCTG GGAGTCTTCA GAATAGAAAC TACCCATCTC AAGAGGAGCT    4680
CATTAAGGTT GTTGATGTGG AGGAGCAACA GCTGGAAGAG TCTGGGCCAC ACGATTTGAC    4740
GGAAACATCT TACTTGCCAA GGCAAGATCT AGAGGGAACC CCTTACCTGG AATCTGGAAT    4800
CAGCCTCTTC TCTGATGACC CTGAATCTGA TCCTTCTGAA GACAGAGCCC CAGAGTCAGC    4860
TCGTGTTGGC AACATACCAT CTTCAACCTC TGCATTGAAA GTTCCCCAAT TGAAAGTTGC    4920
AGAATCTGCC CAGAGTCCAG CTGCTGCTCA TACTACTGAT ACTGCTGGGT ATAATGCAAT    4980
GGAAGAAAGT GTGAGCAGGG AGAAGCCAGA ATTGACAGCT TCAACAGAAA GGGTCAACAA    5040
AAGAATGTCC ATGGTGGTGT CTGGCCTGAC CCCAGAAGAA TTTATGCTCG TGTACAAGTT    5100
TGCCAGAAAA CACCACATCA CTTTAACTAA TCTAATTACT GAAGAGACTA CTCATGTTGT    5160
TATGAAAACA GATGCTGAGT TTGTGTGTGA ACGGACACTG AAATATTTTC TAGGAATTGC    5220
GGGAGGAAAA TGGGTAGTTA GCTATTTCTG GGTGACCCAG TCTATTAAAG AAAGAAAAAT    5280
GCTGAATGAG CATGATTTTG AAGTCAGAGG AGATGTGGTC AATGGAAGAA ACCACCAAGG    5340
```

```
TCCAAAGCGA  GCAAGAGAAT  CCCAGGACAG  AAAGATCTTC  AGGGGGCTAG  AAATCTGTTG    5400

CTATGGGCCC  TTCACCAACA  TGCCCACAGA  TCAACTGGAA  TGGATGGTAC  AGCTGTGTGG    5460

TGCTTCTGTG  GTGAAGGAGC  TTTCATCATT  CACCCTTGGC  ACAGGTGTCC  ACCCAATTGT    5520

GGTTGTGCAG  CCAGATGCCT  GGACAGAGGA  CAATGGCTTC  CATGCAATTG  GCAGATGTG    5580

TGAGGCACCT  GTGGTGACCC  GAGAGTGGGT  GTTGGACAGT  GTAGCACTCT  ACCAGTGCCA    5640

GGAGCTGGAC  ACCTACCTGA  TACCCCAGAT  CCCCCACAGC  CACTACTGA                 5689
```

( 2 ) INFORMATION FOR SEQ ID NO:4:

( i ) SEQUENCE CHARACTERISTICS:
          ( A ) LENGTH: 5711 base pairs
          ( B ) TYPE: nucleic acid
          ( C ) STRANDEDNESS: double
          ( D ) TOPOLOGY: linear ( i i ) MOLECULE TYPE: cDNA ( x i ) SEQUENCE DESCRIPTION: SEQ ID NO:4:

```
AGCTCGCTGA  GACTTCCTGG  ACCCCGCACC  AGGCTGTGGG  GTTTCTCAGA  TAACTGGGCC     60

CCTGCGCTCA  GGAGGCCTTC  ACCCTCTGCT  CTGGGTAAAG  TTCATTGGAA  CAGAAAGAAA    120

TGGATTTATC  TGCTCTTCGC  GTTGAAGAAG  TACAAAATGT  CATTAATGCT  ATGCAGAAAA    180

TCTTAGAGTG  TCCCATCTGT  CTGGAGTTGA  TCAAGGAACC  TGTCTCCACA  AAGTGTGACC    240

ACATATTTTG  CAAATTTTGC  ATGCTGAAAC  TTCTCAACCA  GAAGAAAGGG  CCTTCACAGG    300

GTCCTTTATG  TAAGAATGAT  ATAACCAAAA  GGAGCCTACA  AGAAAGTACG  AGATTTAGTC    360

AACTTGTTGA  AGAGCTATTG  AAAATCATTT  GTGCTTTTCA  GCTTGACACA  GGTTTGGAGT    420

ATGCAAACAG  CTATAATTTT  GCAAAAAAGG  AAAATAACTC  TCCTGAACAT  CTAAAAGATG    480

AAGTTTCTAT  CATCCAAAGT  ATGGGCTACA  GAAACCGTGC  CAAAAGACTT  CTACAGAGTG    540

AACCCGAAAA  TCCTTCCTTG  CAGGAAACCA  GTCTCAGTGT  CCAACTCTCT  AACCTTGGAA    600

CTGTGAGAAC  TCTGAGGACA  AAGCAGCGGA  TACAACCTCA  AAAGACGTCT  GTCTACATTG    660

AATTGGGATC  TGATTCTTCT  GAAGATACCG  TTAATAAGGC  AACTTATTGC  AGTGTGGGAG    720

ATCAAGAATT  GTTACAAATC  ACCCCTCAAG  GAACCAGGGA  TGAAATCAGT  TTGGATTCTG    780

CAAAAAAGGC  TGCTTGTGAA  TTTTCTGAGA  CGGATGTAAC  AAATACTGAA  CATCATCAAC    840

CCAGTAATAA  TGATTTGAAC  ACCACTGAGA  AGCGTGCAGC  TGAGAGGCAT  CCAGAAAAGT    900

ATCAGGGTAG  TTCTGTTTCA  AACTTGCATG  TGGAGCCATG  TGGCACAAAT  ACTCATGCCA    960

GCTCATTACA  GCATGAGAAC  AGCAGTTTAT  TACTCACTAA  AGACAGAATG  AATGTAGAAA   1020

AGGCTGAATT  CTGTAATAAA  AGCAAACAGC  CTGGCTTAGC  AAGGAGCCAA  CATAACAGAT   1080

GGGCTGGAAG  TAAGGAAACA  TGTAATGATA  GGCGGACTCC  CAGCACAGAA  AAAAGGTAG    1140

ATCTGAATGC  TGATCCCCTG  TGTGAGAGAA  AAGAATGGAA  TAAGCAGAAA  CTGCCATGCT   1200

CAGAGAATCC  TAGAGATACT  GAAGATGTTC  CTTGGATAAC  ACTAAATAGC  AGCATTCAGA   1260

AAGTTAATGA  GTGGTTTTCC  AGAAGTGATG  AACTGTTAGG  TTCTGATGAC  TCACATGATG   1320

GGGAGTCTGA  ATCAAATGCC  AAAGTAGCTG  ATGTATTGGA  CGTTCTAAAT  GAGGTAGATG   1380

AATATTCTGG  TTCTTCAGAG  AAAATAGACT  TACTGGCCAG  TGATCCTCAT  GAGGCTTTAA   1440

TATGTAAAAG  TGAAAGAGTT  CACTCCAAAT  CAGTAGAGAG  TAATATTGAA  GACAAAATAT   1500

TTGGGAAAAC  CTATCGGAAG  AAGGCAAGCC  TCCCCAACTT  AAGCCATGTA  ACTGAAAATC   1560

TAATTATAGG  AGCATTTGTT  ACTGAGCCAC  AGATAATACA  AGAGCGTCCC  CTCACAAATA   1620
```

-continued

| | | | | | |
|---|---|---|---|---|---|
| AATTAAAGCG | TAAAAGGAGA | CCTACATCAG | GCCTTCATCC | TGAGGATTTT | ATCAAGAAAG | 1680
| CAGATTTGGC | AGTTCAAAAG | ACTCCTGAAA | TGATAAATCA | GGGAACTAAC | CAAACGGAGC | 1740
| AGAATGGTCA | AGTGATGAAT | ATTACTAATA | GTGGTCATGA | GAATAAAACA | AAAGGTGATT | 1800
| CTATTCAGAA | TGAGAAAAAT | CCTAACCCAA | TAGAATCACT | CGAAAAGAA | TCTGCTTTCA | 1860
| AAACGAAAGC | TGAACCTATA | AGCAGCAGTA | TAAGCAATAT | GGAACTCGAA | TTAAATATCC | 1920
| ACAATTCAAA | AGCACCTAAA | AAGAATAGGC | TGAGGAGGAA | GTCTTCTACC | AGGCATATTC | 1980
| ATGCGCTTGA | ACTAGTAGTC | AGTAGAAATC | TAAGCCCACC | TAATTGTACT | GAATTGCAAA | 2040
| TTGATAGTTG | TTCTAGCAGT | GAAGAGATAA | AGAAAAAAA | GTACAACCAA | ATGCCAGTCA | 2100
| GGCACAGCAG | AAACCTACAA | CTCATGGAAG | GTAAAGAACC | TGCAACTGGA | GCCAAGAAGA | 2160
| GTAACAAGCC | AAATGAACAG | ACAAGTAAAA | GACATGACAG | CGATACTTTC | CCAGAGCTGA | 2220
| AGTTAACAAA | TGCACCTGGT | TCTTTTACTA | AGTGTTCAAA | TACCAGTGAA | CTTAAAGAAT | 2280
| TTGTCAATCC | TAGCCTTCCA | AGAGAAGAAA | AAGAAGAGAA | ACTAGAAACA | GTTAAAGTGT | 2340
| CTAATAATGC | TGAAGACCCC | AAAGATCTCA | TGTTAAGTGG | AGAAAGGGTT | TTGCAAACTG | 2400
| AAAGATCTGT | AGAGAGTAGC | AGTATTTCAT | GGTACCTGG | TACTGATTAT | GGCACTCAGG | 2460
| AAAGTATCTC | GTTACTGGAA | GTTAGCACTC | TAGGGAAGGC | AAAAACAGAA | CCAAATAAAT | 2520
| GTGTGAGTCA | GTGTGCAGCA | TTTGAAAACC | CCAAGGGACT | AATTCATGGT | TGTTCCAAAG | 2580
| ATAATAGAAA | TGACACAGAA | GGCTTTAAGT | ATCCATTGGG | ACATGAAGTT | AACCACAGTC | 2640
| GGGAAACAAG | CATAGAAATG | GAAGAAAGTG | AACTTGATGC | TCAGTATTTG | CAGAATACAT | 2700
| TCAAGGTTTC | AAAGCGCCAG | TCATTTGCTC | CGTTTTCAAA | TCCAGGAAAT | GCAGAAGAGG | 2760
| AATGTGCAAC | ATTCTCTGCC | CACTCTGGGT | CCTTAAAGAA | ACAAAGTCCA | AAAGTCACTT | 2820
| TTGAATGTGA | ACAAAAGGAA | GAAAATCAAG | GAAGAATGA | GTCTAATATC | AAGCCTGTAC | 2880
| AGACAGTTAA | TATCACTGCA | GGCTTTCCTG | TGGTTGGTCA | GAAAGATAAG | CCAGTTGATA | 2940
| ATGCCAAATG | TAGTATCAAA | GGAGGCTCTA | GGTTTTGTCT | ATCATCTCAG | TTCAGAGGCA | 3000
| ACGAAACTGG | ACTCATTACT | CCAAATAAAC | ATGGACTTTT | ACAAACCCA | TATCGTATAC | 3060
| CACCACTTTT | TCCCATCAAG | TCATTTGTTA | AAACTAAATG | TAAGAAAAAT | CTGCTAGAGG | 3120
| AAAACTTTGA | GGAACATTCA | ATGTCACCTG | AAAGAGAAAT | GGGAAATGAG | AACATTCCAA | 3180
| GTACAGTGAG | CACAATTAGC | CGTAATAACA | TTAGAGAAAA | TGTTTTTAAA | GAAGCCAGCT | 3240
| CAAGCAATAT | TAATGAAGTA | GGTTCCAGTA | CTAATGAAGT | GGGCTCCAGT | ATTAATGAAA | 3300
| TAGGTTCCAG | TGATGAAAAC | ATTCAAGCAG | AACTAGGTAG | AAACAGAGGG | CCAAAATTGA | 3360
| ATGCTATGCT | TAGATTAGGG | GTTTTGCAAC | CTGAGGTCTA | TAAACAAAGT | CTTCCTGGAA | 3420
| GTAATTGTAA | GCATCCTGAA | ATAAAAAGC | AAGAATATGA | AGAAGTAGTT | CAGACTGTTA | 3480
| ATACAGATTT | CTCTCCATAT | CTGATTTCAG | ATAACTTAGA | ACAGCCTATG | GGAAGTAGTC | 3540
| ATGCATCTCA | GGTTTGTTCT | GAGACACCTG | ATGACCTGTT | AGATGATGGT | GAAATAAAGG | 3600
| AAGATACTAG | TTTTGCTGAA | AATGACATTA | AGGAAAGTTC | TGCTGTTTTT | AGCAAAGCG | 3660
| TCCAGAAAGG | AGAGCTTAGC | AGGAGTCCTA | GCCCTTTCAC | CCATACACAT | TTGGCTCAGG | 3720
| GTTACCGAAG | AGGGGCCAAG | AAATTAGAGT | CCTCAGAAGA | GAACTTATCT | AGTGAGGATG | 3780
| AAGAGCTTCC | CTGCTTCCAA | CACTTGTTAT | TTGGTAAAGT | AAACAATATA | CCTTCTCAGT | 3840
| CTACTAGGCA | TAGCACCGTT | GCTACCGAGT | GTCTGTCTAA | GAACACAGAG | GAGAATTTAT | 3900
| TATCATTGAA | GAATAGCTTA | AATGACTGCA | GTAACCAGGT | AATATTGGCA | AAGGCATCTC | 3960
| AGGAACATCA | CCTTAGTGAG | GAAACAAAAT | GTTCTGCTAG | CTTGTTTTCT | TCACAGTGCA | 4020

| | | | | | | |
|---|---|---|---|---|---|---|
| GTGAATTGGA | AGACTTGACT | GCAAATACAA | ACACCCAGGA | TCCTTTCTTG | ATTGGTTCTT | 4080 |
| CCAAACAAAT | GAGGCATCAG | TCTGAAAGCC | AGGGAGTTGG | TCTGAGTGAC | AAGGAATTGG | 4140 |
| TTTCAGATGA | TGAAGAAAGA | GGAACGGGCT | TGGAAGAAAA | TAATCAAGAA | GAGCAAAGCA | 4200 |
| TGGATTCAAA | CTTAGGTGAA | GCAGCATCTG | GGTGTGAGAG | TGAAACAAGC | GTCTCTGAAG | 4260 |
| ACTGCTCAGG | GCTATCCTCT | CAGAGTGACA | TTTTAACCAC | TCAGCAGAGG | GATACCATGC | 4320 |
| AACATAACCT | GATAAAGCTC | CAGCAGGAAA | TGGCTGAACT | AGAAGCTGTG | TTAGAACAGC | 4380 |
| ATGGGAGCCA | GCCTTCTAAC | AGCTACCCTT | CCATCATAAG | TGACTCTTCT | GCCCTTGAGG | 4440 |
| ACCTGCGAAA | TCCAGAACAA | AGCACATCAG | AAAAAGCAGT | ATTAACTTCA | CAGAAAAGTA | 4500 |
| GTGAATACCC | TATAAGCCAG | AATCCAGAAG | GCCTTTCTGC | TGACAAGTTT | GAGGTGTCTG | 4560 |
| CAGATAGTTC | TACCAGTAAA | AATAAAGAAC | CAGGAGTGGA | AAGGTCATCC | CCTTCTAAAT | 4620 |
| GCCCATCATT | AGATGATAGG | TGGTACATGC | ACAGTTGCTC | TGGGAGTCTT | CAGAATAGAA | 4680 |
| ACTACCCATC | TCAAGAGGAG | CTCATTAAGG | TTGTTGATGT | GGAGGAGCAA | CAGCTGGAAG | 4740 |
| AGTCTGGGCC | ACACGATTTG | ACGGAAACAT | CTTACTTGCC | AAGGCAAGAT | CTAGAGGGAA | 4800 |
| CCCCTTACCT | GGAATCTGGA | ATCAGCCTCT | TCTCTGATGA | CCCTGAATCT | GATCCTTCTG | 4860 |
| AAGACAGAGC | CCCAGAGTCA | GCTCGTGTTG | GCAACATACC | ATCTTCAACC | TCTGCATTGA | 4920 |
| AGTTCCCCA | ATTGAAAGTT | GCAGAATCTG | CCCAGAGTCC | AGCTGCTGCT | CATACTACTG | 4980 |
| ATACTGCTGG | GTATAATGCA | ATGGAAGAAA | GTGTGAGCAG | GGAGAAGCCA | GAATTGACAG | 5040 |
| CTTCAACAGA | AAGGGTCAAC | AAAAGAATGT | CCATGGTGGT | GTCTGGCCTG | ACCCCAGAAG | 5100 |
| AATTTATGCT | CGTGTACAAG | TTTGCCAGAA | ACACCACAT | CACTTTAACT | AATCTAATTA | 5160 |
| CTGAAGAGAC | TACTCATGTT | GTTATGAAAA | CAGATGCTGA | GTTTGTGTGT | GAACGGACAC | 5220 |
| TGAAATATTT | TCTAGGAATT | GCGGGAGGAA | AATGGGTAGT | TAGCTATTTC | TGGGTGACCC | 5280 |
| AGTCTATTAA | AGAAAGAAAA | ATGCTGAATG | AGCATGATTT | TGAAGTCAGA | GGAGATGTGG | 5340 |
| TCAATGGAAG | AAACCACCAA | GGTCCAAAGC | GAGCAAGAGA | ATCCCAGGAC | AGAAAGATCT | 5400 |
| TCAGGGGGCT | AGAAATCTGT | TGCTATGGGC | CCTTCACCAA | CATGCCCACA | GATCAACTGG | 5460 |
| AATGGATGGT | ACAGCTGTGT | GGTGCTTCTG | TGGTGAAGGA | GCTTTCATCA | TTCACCCTTG | 5520 |
| GCACAGGTGT | CCACCCAATT | GTGGTTGTGC | AGCCAGATGC | CTGGACAGAG | GACAATGGCT | 5580 |
| TCCATGCAAT | TGGGCAGATG | TGTGAGGCAC | CTGTGGTGAC | CCGAGAGTGG | GTGTTGGACA | 5640 |
| GTGTAGCACT | CTACCAGTGC | CAGGAGCTGG | ACACCTACCT | GATACCCCAG | ATCCCCCACA | 5700 |
| GCCACTACTG | A | | | | | 5711 |

( 2 ) INFORMATION FOR SEQ ID NO:5:

( i ) SEQUENCE CHARACTERISTICS:
        ( A ) LENGTH: 5770 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

| | | | | | | |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAAGGG | CCTTCACAGT | 300 |

| | | | | | | |
|---|---|---|---|---|---|---|
| GTCCTTTATG | TAAGAATGAT | ATAACCAAAA | GTGTCCTTAA | AAGGTTGATA | ATCACTTGCT | 360 |
| GAGTGTGTTT | CTCAAACAAG | TTAATTTCAG | GAGCCTACAA | GAAAGTACGA | GATTTAGTCA | 420 |
| ACTTGTTGAA | GAGCTATTGA | AAATCATTTG | TGCTTTTCAG | CTTGACACAG | GTTTGGAGTA | 480 |
| TGCAAACAGC | TATAATTTTG | CAAAAAAGGA | AAATAACTCT | CCTGAACATC | TAAAAGATGA | 540 |
| AGTTTCTATC | ATCCAAAGTA | TGGGCTACAG | AAACCGTGCC | AAAAGACTTC | TACAGAGTGA | 600 |
| ACCCGAAAAT | CCTTCCTTGC | AGGAAACCAG | TCTCAGTGTC | CAACTCTCTA | ACCTTGGAAC | 660 |
| TGTGAGAACT | CTGAGGACAA | AGCAGCGGAT | ACAACCTCAA | AAGACGTCTG | TCTACATTGA | 720 |
| ATTGGGATCT | GATTCTTCTG | AAGATACCGT | TAATAAGGCA | ACTTATTGCA | GTGTGGGAGA | 780 |
| TCAAGAATTG | TTACAAATCA | CCCCTCAAGG | AACCAGGGAT | GAAATCAGTT | TGGATTCTGC | 840 |
| AAAAAAGGCT | GCTTGTGAAT | TTTCTGAGAC | GGATGTAACA | AATACTGAAC | ATCATCAACC | 900 |
| CAGTAATAAT | GATTTGAACA | CCACTGAGAA | GCGTGCAGCT | GAGAGGCATC | CAGAAAAGTA | 960 |
| TCAGGGTAGT | TCTGTTTCAA | ACTTGCATGT | GGAGCCATGT | GGCACAAATA | CTCATGCCAG | 1020 |
| CTCATTACAG | CATGAGAACA | GCAGTTTATT | ACTCACTAAA | GACAGAATGA | ATGTAGAAAA | 1080 |
| GGCTGAATTC | TGTAATAAAA | GCAAACAGCC | TGGCTTAGCA | AGGAGCCAAC | ATAACAGATG | 1140 |
| GGCTGGAAGT | AAGGAAACAT | GTAATGATAG | GCGGACTCCC | AGCACAGAAA | AAAAGGTAGA | 1200 |
| TCTGAATGCT | GATCCCCTGT | GTGAGAGAAA | AGAATGGAAT | AAGCAGAAAC | TGCCATGCTC | 1260 |
| AGAGAATCCT | AGAGATACTG | AAGATGTTCC | TTGGATAACA | CTAAATAGCA | GCATTCAGAA | 1320 |
| AGTTAATGAG | TGGTTTTCCA | GAAGTGATGA | ACTGTTAGGT | TCTGATGACT | CACATGATGG | 1380 |
| GGAGTCTGAA | TCAAATGCCA | AAGTAGCTGA | TGTATTGGAC | GTTCTAAATG | AGGTAGATGA | 1440 |
| ATATTCTGGT | TCTTCAGAGA | AAATAGACTT | ACTGGCCAGT | GATCCTCATG | AGGCTTTAAT | 1500 |
| ATGTAAAAGT | GAAAGAGTTC | ACTCCAAATC | AGTAGAGAGT | AATATTGAAG | ACAAAATATT | 1560 |
| TGGGAAAACC | TATCGGAAGA | AGGCAAGCCT | CCCCAACTTA | AGCCATGTAA | CTGAAAATCT | 1620 |
| AATTATAGGA | GCATTTGTTA | CTGAGCCACA | GATAATACAA | GAGCGTCCCC | TCACAAATAA | 1680 |
| ATTAAAGCGT | AAAAGGAGAC | CTACATCAGG | CCTTCATCCT | GAGGATTTTA | TCAAGAAAGC | 1740 |
| AGATTTGGCA | GTTCAAAAGA | CTCCTGAAAT | GATAAATCAG | GAACTAACC | AAACGGAGCA | 1800 |
| GAATGGTCAA | GTGATGAATA | TTACTAATAG | TGGTCATGAG | AATAAAACAA | AAGGTGATTC | 1860 |
| TATTCAGAAT | GAGAAAAATC | CTAACCCAAT | AGAATCACTC | GAAAAGAAT | CTGCTTTCAA | 1920 |
| AACGAAAGCT | GAACCTATAA | GCAGCAGTAT | AAGCAATATG | GAACTCGAAT | TAAATATCCA | 1980 |
| CAATTCAAAA | GCACCTAAAA | AGAATAGGCT | GAGGAGGAAG | TCTTCTACCA | GGCATATTCA | 2040 |
| TGCGCTTGAA | CTAGTAGTCA | GTAGAAATCT | AAGCCCACCT | AATTGTACTG | AATTGCAAAT | 2100 |
| TGATAGTTGT | TCTAGCAGTG | AAGAGATAAA | GAAAAAAAG | TACAACCAAA | TGCCAGTCAG | 2160 |
| GCACAGCAGA | AACCTACAAC | TCATGGAAGG | TAAAGAACCT | GCAACTGGAG | CCAAGAAGAG | 2220 |
| TAACAAGCCA | AATGAACAGA | CAAGTAAAAG | ACATGACAGC | GATACTTTCC | CAGAGCTGAA | 2280 |
| GTTAACAAAT | GCACCTGGTT | CTTTTACTAA | GTGTTCAAAT | ACCAGTGAAC | TTAAAGAATT | 2340 |
| TGTCAATCCT | AGCCTTCCAA | GAGAAGAAAA | AGAAGAGAAA | CTAGAAACAG | TTAAAGTGTC | 2400 |
| TAATAATGCT | GAAGACCCCA | AAGATCTCAT | GTTAAGTGGA | GAAAGGGTTT | TGCAAACTGA | 2460 |
| AAGATCTGTA | GAGAGTAGCA | GTATTTCATT | GGTACCTGGT | ACTGATTATG | GCACTCAGGA | 2520 |
| AAGTATCTCG | TTACTGGAAG | TTAGCACTCT | AGGGAAGGCA | AAAACAGAAC | CAAATAAATG | 2580 |
| TGTGAGTCAG | TGTGCAGCAT | TTGAAAACCC | CAAGGGACTA | ATTCATGGTT | GTTCCAAAGA | 2640 |
| TAATAGAAAT | GACACAGAAG | GCTTTAAGTA | TCCATTGGGA | CATGAAGTTA | ACCACAGTCG | 2700 |

```
GGAAACAAGC ATAGAAATGG AAGAAAGTGA ACTTGATGCT CAGTATTTGC AGAATACATT    2760
CAAGGTTTCA AAGCGCCAGT CATTTGCTCC GTTTTCAAAT CCAGGAAATG CAGAAGAGGA    2820
ATGTGCAACA TTCTCTGCCC ACTCTGGGTC CTTAAAGAAA CAAAGTCCAA AAGTCACTTT    2880
TGAATGTGAA CAAAAGGAAG AAAATCAAGG AAAGAATGAG TCTAATATCA AGCCTGTACA    2940
GACAGTTAAT ATCACTGCAG GCTTTCCTGT GGTTGGTCAG AAAGATAAGC CAGTTGATAA    3000
TGCCAAATGT AGTATCAAAG GAGGCTCTAG GTTTTGTCTA TCATCTCAGT TCAGAGGCAA    3060
CGAAACTGGA CTCATTACTC CAAATAAACA TGGACTTTTA CAAAACCCAT ATCGTATACC    3120
ACCACTTTTT CCCATCAAGT CATTTGTTAA AACTAAATGT AAGAAAAATC TGCTAGAGGA    3180
AAACTTTGAG GAACATTCAA TGTCACCTGA AAGAGAAATG GAAATGAGA ACATTCCAAG     3240
TACAGTGAGC ACAATTAGCC GTAATAACAT TAGAGAAAAT GTTTTAAAG AAGCCAGCTC     3300
AAGCAATATT AATGAAGTAG GTTCCAGTAC TAATGAAGTG GGCTCCAGTA TTAATGAAAT    3360
AGGTTCCAGT GATGAAAACA TTCAAGCAGA ACTAGGTAGA AACAGAGGGC AAAATTGAA     3420
TGCTATGCTT AGATTAGGGG TTTTGCAACC TGAGGTCTAT AAACAAAGTC TTCCTGGAAG    3480
TAATTGTAAG CATCCTGAAA TAAAAAAGCA AGAATATGAA GAAGTAGTTC AGACTGTTAA    3540
TACAGATTTC TCTCCATATC TGATTTCAGA TAACTTAGAA CAGCCTATGG GAAGTAGTCA    3600
TGCATCTCAG GTTTGTTCTG AGACACCTGA TGACCTGTTA GATGATGGTG AAATAAAGGA    3660
AGATACTAGT TTTGCTGAAA ATGACATTAA GGAAAGTTCT GCTGTTTTTA GCAAAAGCGT    3720
CCAGAAAGGA GAGCTTAGCA GGAGTCCTAG CCCTTTCACC CATACACATT TGGCTCAGGG    3780
TTACCGAAGA GGGGCCAAGA AATTAGAGTC CTCAGAAGAG AACTTATCTA GTGAGGATGA    3840
AGAGCTTCCC TGCTTCCAAC ACTTGTTATT TGGTAAAGTA AACAATATAC CTTCTCAGTC    3900
TACTAGGCAT AGCACCGTTG CTACCGAGTG TCTGTCTAAG AACACAGAGG AGAATTTATT    3960
ATCATTGAAG AATAGCTTAA ATGACTGCAG TAACCAGGTA ATATTGGCAA AGGCATCTCA    4020
GGAACATCAC CTTAGTGAGG AAACAAAATG TTCTGCTAGC TTGTTTTCTT CACAGTGCAG    4080
TGAATTGGAA GACTTGACTG CAAATACAAA CACCCAGGAT CCTTTCTTGA TTGGTTCTTC    4140
CAAACAAATG AGGCATCAGT CTGAAAGCCA GGGAGTTGGT CTGAGTGACA AGGAATTGGT    4200
TTCAGATGAT GAAGAAAGAG GAACGGGCTT GGAAGAAAAT AATCAAGAAG AGCAAAGCAT    4260
GGATTCAAAC TTAGGTGAAG CAGCATCTGG GTGTGAGAGT GAAACAAGCG TCTCTGAAGA    4320
CTGCTCAGGG CTATCCTCTC AGAGTGACAT TTTAACCACT CAGCAGAGGG ATACCATGCA    4380
ACATAACCTG ATAAAGCTCC AGCAGGAAAT GGCTGAACTA GAAGCTGTGT TAGAACAGCA    4440
TGGGAGCCAG CCTTCTAACA GCTACCCTTC CATCATAAGT GACTCTTCTG CCCTTGAGGA    4500
CCTGCGAAAT CCAGAACAAA GCACATCAGA AAAAGCAGTA TTAACTTCAC AGAAAAGTAG    4560
TGAATACCCT ATAAGCCAGA ATCCAGAAGG CCTTTCTGCT GACAAGTTTG AGGTGTCTGC    4620
AGATAGTTCT ACCAGTAAAA ATAAAGAACC AGGAGTGGAA AGGTCATCCC CTTCTAAATG    4680
CCCATCATTA GATGATAGGT GGTACATGCA CAGTTGCTCT GGGAGTCTTC AGAATAGAAA    4740
CTACCCATCT CAAGAGGAGC TCATTAAGGT TGTTGATGTG GAGGAGCAAC AGCTGGAAGA    4800
GTCTGGGCCA CACGATTTGA CGGAAACATC TTACTTGCCA AGGCAAGATC TAGAGGGAAC    4860
CCCTTACCTG GAATCTGGAA TCAGCCTCTT CTCTGATGAC CCTGAATCTG ATCCTTCTGA    4920
AGACAGAGCC CCAGAGTCAG CTCGTGTTGG CAACATACCA TCTTCAACCT CTGCATTGAA    4980
AGTTCCCCAA TTGAAAGTTG CAGAATCTGC CCAGAGTCCA GCTGCTGCTC ATACTACTGA    5040
TACTGCTGGG TATAATGCAA TGGAAGAAAG TGTGAGCAGG GAGAAGCCAG AATTGACAGC    5100
```

| | | | | | |
|---|---|---|---|---|---|
| TTCAACAGAA | AGGGTCAACA | AAAGAATGTC | CATGGTGGTG | TCTGGCCTGA | CCCCAGAAGA | 5160
| ATTTATGCTC | GTGTACAAGT | TTGCCAGAAA | ACACCACATC | ACTTAACTA | ATCTAATTAC | 5220
| TGAAGAGACT | ACTCATGTTG | TTATGAAAAC | AGATGCTGAG | TTTGTGTGTG | AACGGACACT | 5280
| GAAATATTTT | CTAGGAATTG | CGGGAGGAAA | ATGGGTAGTT | AGCTATTTCT | GGGTGACCCA | 5340
| GTCTATTAAA | GAAAGAAAAA | TGCTGAATGA | GCATGATTTT | GAAGTCAGAG | GAGATGTGGT | 5400
| CAATGGAAGA | AACCACCAAG | GTCCAAAGCG | AGCAAGAGAA | TCCCAGGACA | GAAAGATCTT | 5460
| CAGGGGCTA | GAAATCTGTT | GCTATGGCC | CTTCACCAAC | ATGCCCACAG | ATCAACTGGA | 5520
| ATGGATGGTA | CAGCTGTGTG | GTGCTTCTGT | GGTGAAGGAG | CTTTCATCAT | TCACCCTTGG | 5580
| CACAGGTGTC | CACCCAATTG | TGGTTGTGCA | GCCAGATGCC | TGGACAGAGG | ACAATGGCTT | 5640
| CCATGCAATT | GGGCAGATGT | GTGAGGCACC | TGTGGTGACC | CGAGAGTGGG | TGTTGGACAG | 5700
| TGTAGCACTC | TACCAGTGCC | AGGAGCGGAC | ACCTAACCTG | ATACCCCAGA | TCCCCCACAG | 5760
| CCACTACTGA | | | | | | 5770

(2) INFORMATION FOR SEQ ID NO:6:

(i) SEQUENCE CHARACTERISTICS:
        (A) LENGTH: 5710 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

| | | | | | |
|---|---|---|---|---|---|
| AGCTCGCTGA | GACTTCCTGG | ACCCCGCACC | AGGCTGTGGG | GTTTCTCAGA | TAACTGGGCC | 60
| CCTGCGCTCA | GGAGGCCTTC | ACCCTCTGCT | CTGGGTAAAG | TTCATTGGAA | CAGAAAGAAA | 120
| TGGATTTATC | TGCTCTTCGC | GTTGAAGAAG | TACAAAATGT | CATTAATGCT | ATGCAGAAAA | 180
| TCTTAGAGTG | TCCCATCTGT | CTGGAGTTGA | TCAAGGAACC | TGTCTCCACA | AAGTGTGACC | 240
| ACATATTTTG | CAAATTTTGC | ATGCTGAAAC | TTCTCAACCA | GAAGAAAGGG | CCTTCACAGT | 300
| GTCCTTTATG | TAAGAATGAT | ATAACCAAAA | GGAGCCTACA | AGAAAGTACG | AGATTTAGTC | 360
| AACTTGTTGA | AGAGCTATTG | AAAATCATTT | GTGCTTTTCA | GCTTGACACA | GGTTTGGAGT | 420
| ATGCAAACAG | CTATAATTTT | GCAAAAAAGG | AAAATAACTC | TCCTGAACAT | CTAAAAGATG | 480
| AAGTTTCTAT | CATCCAAAGT | ATGGGCTACA | GAAACCGTGC | CAAAAGACTT | CTACAGAGTG | 540
| AACCCGAAAA | TCCTTCCTTG | CAGGAAACCA | GTCTCAGTGT | CCAACTCTCT | AACCTTGGAA | 600
| CTGTGAGAAC | TCTGAGGACA | AAGCAGCGGA | TACAACCTCA | AAAGACGTCT | GTCTACATTG | 660
| AATTGGGATC | TGATTCTTCT | GAAGATACCG | TTAATAAGGC | AACTTATTGC | AGTGTGGGAG | 720
| ATCAAGAATT | GTTACAAATC | ACCCCTCAAG | GAACCAGGGA | TGAAATCAGT | TTGGATTCTG | 780
| CAAAAAAGGC | TGCTTGTGAA | TTTTCTGAGA | CGGATGTAAC | AAATACTGAA | CATCATCAAC | 840
| CCAGTAATAA | TGATTTGAAC | ACCACTGAGA | AGCGTGCAGC | TGAGAGGCAT | CCAGAAAAGT | 900
| ATCAGGGTAG | TTCTGTTTCA | AACTTGCATG | TGGAGCCATG | TGGCACAAAT | ACTCATGCCA | 960
| GCTCATTACA | GCATGAGAAC | AGCAGTTTAT | TACTCACTAA | AGACAGAATG | AATGTAGAAA | 1020
| AGGCTGAATT | CTGTAATAAA | AGCAAACGCC | TGGCTTAGCA | AGGAGCCAAC | ATAACAGATG | 1080
| GGCTGGAAGT | AAGGAAACAT | GTAATGATAG | GCGGACTCCC | AGCACAGAAA | AAAGGTAGA | 1140
| TCTGAATGCT | GATCCCCTGT | GTGAGAGAAA | AGAATGGAAT | AAGCAGAAAC | TGCCATGCTC | 1200
| AGAGAATCCT | AGAGATACTG | AAGATGTTCC | TTGGATAACA | CTAAATAGCA | GCATTCAGAA | 1260

-continued

| | | | | | |
|---|---|---|---|---|---|
| AGTTAATGAG | TGGTTTTCCA | GAAGTGATGA | ACTGTTAGGT | TCTGATGACT | CACATGATGG | 1320 |
| GGAGTCTGAA | TCAAATGCCA | AAGTAGCTGA | TGTATTGGAC | GTTCTAAATG | AGGTAGATGA | 1380 |
| ATATTCTGGT | TCTTCAGAGA | AAATAGACTT | ACTGGCCAGT | GATCCTCATG | AGGCTTTAAT | 1440 |
| ATGTAAAAGT | GAAAGAGTTC | ACTCCAAATC | AGTAGAGAGT | AATATTGAAG | ACAAATATT | 1500 |
| TGGGAAAACC | TATCGGAAGA | AGGCAAGCCT | CCCCAACTTA | AGCCATGTAA | CTGAAAATCT | 1560 |
| AATTATAGGA | GCATTTGTTA | CTGAGCCACA | GATAATACAA | GAGCGTCCCC | TCACAAATAA | 1620 |
| ATTAAAGCGT | AAAAGGAGAC | CTACATCAGG | CCTTCATCCT | GAGGATTTTA | TCAAGAAAGC | 1680 |
| AGATTTGGCA | GTTCAAAAGA | CTCCTGAAAT | GATAAATCAG | GGAACTAACC | AAACGGAGCA | 1740 |
| GAATGGTCAA | GTGATGAATA | TTACTAATAG | TGGTCATGAG | AATAAAACAA | AAGGTGATTC | 1800 |
| TATTCAGAAT | GAGAAAAATC | CTAACCCAAT | AGAATCACTC | GAAAAGAAT | CTGCTTTCAA | 1860 |
| AACGAAAGCT | GAACCTATAA | GCAGCAGTAT | AAGCAATATG | GAACTCGAAT | TAAATATCCA | 1920 |
| CAATTCAAAA | GCACCTAAAA | AGAATAGGCT | GAGGAGGAAG | TCTTCTACCA | GGCATATTCA | 1980 |
| TGCGCTTGAA | CTAGTAGTCA | GTAGAAATCT | AAGCCCACCT | AATTGTACTG | AATTGCAAAT | 2040 |
| TGATAGTTGT | TCTAGCAGTG | AAGAGATAAA | GAAAAAAAG | TACAACCAAA | TGCCAGTCAG | 2100 |
| GCACAGCAGA | AACCTACAAC | TCATGGAAGG | TAAAGAACCT | GCAACTGGAG | CCAAGAAGAG | 2160 |
| TAACAAGCCA | AATGAACAGA | CAAGTAAAAG | ACATGACAGC | GATACTTTCC | CAGAGCTGAA | 2220 |
| GTTAACAAAT | GCACCTGGTT | CTTTTACTAA | GTGTTCAAAT | ACCAGTGAAC | TTAAAGAATT | 2280 |
| TGTCAATCCT | AGCCTTCCAA | GAGAAGAAA | AGAAGAGAAA | CTAGAAACAG | TTAAAGTGTC | 2340 |
| TAATAATGCT | GAAGACCCCA | AAGATCTCAT | GTTAAGTGGA | GAAAGGGTTT | TGCAAACTGA | 2400 |
| AAGATCTGTA | GAGAGTAGCA | GTATTTCATT | GGTACCTGGT | ACTGATTATG | GCACTCAGGA | 2460 |
| AAGTATCTCG | TTACTGGAAG | TTAGCACTCT | AGGGAAGGCA | AAAACAGAAC | CAAATAAATG | 2520 |
| TGTGAGTCAG | TGTGCAGCAT | TTGAAAACCC | CAAGGGACTA | ATTCATGGTT | GTTCCAAAGA | 2580 |
| TAATAGAAAT | GACACAGAAG | GCTTTAAGTA | TCCATTGGGA | CATGAAGTTA | ACCACAGTCG | 2640 |
| GGAAACAAGC | ATAGAAATGG | AAGAAAGTGA | ACTTGATGCT | CAGTATTTGC | AGAATACATT | 2700 |
| CAAGGTTTCA | AAGCGCCAGT | CATTTGCTCC | GTTTTCAAAT | CCAGGAAATG | CAGAAGAGGA | 2760 |
| ATGTGCAACA | TTCTCTGCCC | ACTCTGGGTC | CTTAAAGAAA | CAAAGTCCAA | AAGTCACTTT | 2820 |
| TGAATGTGAA | CAAAAGGAAG | AAAATCAAGG | AAAGAATGAG | TCTAATATCA | AGCCTGTACA | 2880 |
| GACAGTTAAT | ATCACTGCAG | GCTTTCCTGT | GGTTGGTCAG | AAAGATAAGC | CAGTTGATAA | 2940 |
| TGCCAAATGT | AGTATCAAAG | GAGGCTCTAG | GTTTTGTCTA | TCATCTCAGT | TCAGAGGCAA | 3000 |
| CGAAACTGGA | CTCATTACTC | CAAATAAACA | TGGACTTTTA | CAAAACCCAT | ATCGTATACC | 3060 |
| ACCACTTTTT | CCCATCAAGT | CATTTGTTAA | AACTAAATGT | AAGAAAAATC | TGCTAGAGGA | 3120 |
| AAACTTTGAG | GAACATTCAA | TGTCACCTGA | AAGAGAAATG | GGAAATGAGA | ACATTCCAAG | 3180 |
| TACAGTGAGC | ACAATTAGCC | GTAATAACAT | TAGAGAAAAT | GTTTTTAAAG | AAGCCAGCTC | 3240 |
| AAGCAATATT | AATGAAGTAG | GTTCCAGTAC | TAATGAAGTG | GGCTCCAGTA | TTAATGAAAT | 3300 |
| AGGTTCCAGT | GATGAAAACA | TTCAAGCAGA | ACTAGGTAGA | AACAGAGGGC | CAAAATTGAA | 3360 |
| TGCTATGCTT | AGATTAGGGG | TTTTGCAACC | TGAGGTCTAT | AAACAAAGTC | TTCCTGGAAG | 3420 |
| TAATTGTAAG | CATCCTGAAA | TAAAAAGCA | AGAATATGAA | GAAGTAGTTC | AGACTGTTAA | 3480 |
| TACAGATTTC | TCTCCATATC | TGATTTCAGA | TAACTTAGAA | CAGCCTATGG | GAAGTAGTCA | 3540 |
| TGCATCTCAG | GTTTGTTCTG | AGACACCTGA | TGACCTGTTA | GATGATGGTG | AAATAAAGGA | 3600 |
| AGATACTAGT | TTTGCTGAAA | ATGACATTAA | GGAAAGTTCT | GCTGTTTTTA | GCAAAAGCGT | 3660 |

| | | | | | | |
|---|---|---|---|---|---|---|
| CCAGAAAGGA | GAGCTTAGCA | GGAGTCCTAG | CCCTTTCACC | CATACACATT | TGGCTCAGGG | 3720 |
| TTACCGAAGA | GGGGCCAAGA | AATTAGAGTC | CTCAGAAGAG | AACTTATCTA | GTGAGGATGA | 3780 |
| AGAGCTTCCC | TGCTTCCAAC | ACTTGTTATT | TGGTAAAGTA | AACAATATAC | CTTCTCAGTC | 3840 |
| TACTAGGCAT | AGCACCGTTG | CTACCGAGTG | TCTGTCTAAG | AACACAGAGG | AGAATTTATT | 3900 |
| ATCATTGAAG | AATAGCTTAA | ATGACTGCAG | TAACCAGGTA | ATATTGGCAA | AGGCATCTCA | 3960 |
| GGAACATCAC | CTTAGTGAGG | AAACAAAATG | TTCTGCTAGC | TTGTTTTCTT | CACAGTGCAG | 4020 |
| TGAATTGGAA | GACTTGACTG | CAAATACAAA | CACCCAGGAT | CCTTCTTGA | TTGGTTCTTC | 4080 |
| CAAACAAATG | AGGCATCAGT | CTGAAAGCCA | GGGAGTTGGT | CTGAGTGACA | AGGAATTGGT | 4140 |
| TTCAGATGAT | GAAGAAAGAG | GAACGGGCTT | GGAAGAAAAT | AATCAAGAAG | AGCAAAGCAT | 4200 |
| GGATTCAAAC | TTAGGTGAAG | CAGCATCTGG | GTGTGAGAGT | GAAACAAGCG | TCTCTGAAGA | 4260 |
| CTGCTCAGGG | CTATCCTCTC | AGAGTGACAT | TTTAACCACT | CAGCAGAGGG | ATACCATGCA | 4320 |
| ACATAACCTG | ATAAAGCTCC | AGCAGGAAAT | GGCTGAACTA | GAAGCTGTGT | TAGAACAGCA | 4380 |
| TGGGAGCCAG | CCTTCTAACA | GCTACCCTTC | CATCATAAGT | GACTCTTCTG | CCCTTGAGGA | 4440 |
| CCTGCGAAAT | CCAGAACAAA | GCACATCAGA | AAAAGCAGTA | TTAACTTCAC | AGAAAAGTAG | 4500 |
| TGAATACCCT | ATAAGCCAGA | ATCCAGAAGG | CCTTTCTGCT | GACAAGTTTG | AGGTGTCTGC | 4560 |
| AGATAGTTCT | ACCAGTAAAA | ATAAAGAACC | AGGAGTGGAA | AGGTCATCCC | CTTCTAAATG | 4620 |
| CCCATCATTA | GATGATAGGT | GGTACATGCA | CAGTTGCTCT | GGGAGTCTTC | AGAATAGAAA | 4680 |
| CTACCCATCT | CAAGAGGAGC | TCATTAAGGT | TGTTGATGTG | GAGGAGCAAC | AGCTGGAAGA | 4740 |
| GTCTGGGCCA | CACGATTTGA | CGGAAACATC | TTACTTGCCA | AGGCAAGATC | TAGAGGGAAC | 4800 |
| CCCTTACCTG | GAATCTGGAA | TCAGCCTCTT | CTCTGATGAC | CCTGAATCTG | ATCCTTCTGA | 4860 |
| AGACAGAGCC | CCAGAGTCAG | CTCGTGTTGG | CAACATACCA | TCTTCAACCT | CTGCATTGAA | 4920 |
| AGTTCCCCAA | TTGAAAGTTG | CAGAATCTGC | CCAGAGTCCA | GCTGCTGCTC | ATACTACTGA | 4980 |
| TACTGCTGGG | TATAATGCAA | TGGAAGAAAG | TGTGAGCAGG | GAGAAGCCAG | AATTGACAGC | 5040 |
| TTCAACAGAA | AGGGTCAACA | AAAGAATGTC | CATGGTGGTG | TCTGGCCTGA | CCCCAGAAGA | 5100 |
| ATTTATGCTC | GTGTACAAGT | TTGCCAGAAA | ACACCACATC | ACTTTAACTA | ATCTAATTAC | 5160 |
| TGAAGAGACT | ACTCATGTTG | TTATGAAAAC | AGATGCTGAG | TTTGTGTGTG | AACGGACACT | 5220 |
| GAAATATTTT | CTAGGAATTG | CGGGAGGAAA | ATGGGTAGTT | AGCTATTTCT | GGGTGACCCA | 5280 |
| GTCTATTAAA | GAAAGAAAAA | TGCTGAATGA | GCATGATTTT | GAAGTCAGAG | GAGATGTGGT | 5340 |
| CAATGGAAGA | AACCACCAAG | GTCCAAAGCG | AGCAAGAGAA | TCCCAGGACA | GAAAGATCTT | 5400 |
| CAGGGGCTA | GAAATCTGTT | GCTATGGGCC | CTTCACCAAC | ATGCCCACAG | ATCAACTGGA | 5460 |
| ATGGATGGTA | CAGCTGTGTG | GTGCTTCTGT | GGTGAAGGAG | CTTTCATCAT | TCACCCTTGG | 5520 |
| CACAGGTGTC | CACCCAATTG | TGGTTGTGCA | GCCAGATGCC | TGGACAGAGG | ACAATGGCTT | 5580 |
| CCATGCAATT | GGGCAGATGT | GTGAGGCACC | TGTGGTGACC | CGAGAGTGGG | TGTTGGACAG | 5640 |
| TGTAGCACTC | TACCAGTGCC | AGGAGCTGGA | CACCTACCTG | ATACCCAGA | TCCCCACAG | 5700 |
| CCACTACTGA | | | | | | 5710 |

( 2 ) INFORMATION FOR SEQ ID NO:7:

( i ) SEQUENCE CHARACTERISTICS:
  ( A ) LENGTH: 5709 base pairs
  ( B ) TYPE: nucleic acid
  ( C ) STRANDEDNESS: double
  ( D ) TOPOLOGY: linear ( i i ) MOLECULE TYPE: cDNA (xi) SEQUENCE DESCRIPTION: SEQ ID NO:7:

```
AGCTCGCTGA GACTTCCTGG ACCCCGCACC AGGCTGTGGG GTTTCTCAGA TAACTGGGCC      60
CCTGCGCTCA GGAGGCCTTC ACCCTCTGCT CTGGGTAAAG TTCATTGGAA CAGAAAGAAA     120
TGGATTTATC TGCTCTTCGC GTTGAAGAAG TACAAAATGT CATTAATGCT ATGCAGAAAA     180
TCTTAGAGTG TCCCATCTGT CTGGAGTTGA TCAAGGAACC TGTCTCCACA AAGTGTGACC     240
ACATATTTTG CAAATTTTGC ATGCTGAAAC TTCTCAACCA GAAGAAGGG CCTTCACAGT      300
GTCCTTTATG TAAGAATGAT ATAACCAAAA GGAGCCTACA AGAAAGTACG AGATTTAGTC     360
AACTTGTTGA AGAGCTATTG AAAATCATTT GTGCTTTTCA GCTTGACACA GGTTTGGAGT     420
ATGCAAACAG CTATAATTTT GCAAAAAAGG AAAATAACTC TCCTGAACAT CTAAAAGATG     480
AAGTTTCTAT CATCCAAAGT ATGGGCTACA GAAACCGTGC CAAAAGACTT CTACAGAGTG     540
AACCCGAAAA TCCTTCCTTG CAGGAAACCA GTCTCAGTGT CCAACTCTCT AACCTTGGAA     600
CTGTGAGAAC TCTGAGGACA AAGCAGCGGA TACAACCTCA AAAGACGTCT GTCTACATTG     660
AATTGGGATC TGATTCTTCT GAAGATACCG TTAATAAGGC AACTTATTGC AGTGTGGGAG     720
ATCAAGAATT GTTACAAATC ACCCCTCAAG GAACCAGGGA TGAAATCAGT TTGGATTCTG     780
CAAAAAAGGC TGCTTGTGAA TTTTCTGAGA CGGATGTAAC AAATACTGAA CATCATCAAC     840
CCAGTAATAA TGATTTGAAC ACCACTGAGA AGCGTGCAGC TGAGAGGCAT CCAGAAAAGT     900
ATCAGGGTAG TTCTGTTTCA AACTTGCATG TGGAGCCATG TGGCACAAAT ACTCATGCCA     960
GCTCATTACA GCATGAGAAC AGCAGTTTAT TACTCACTAA AGACAGAATG AATGTAGAAA    1020
AGGCTGAATT CTGTAATAAA AGCAAACAGC CTGGCTTAGC AAGGAGCCAA CATAACAGAT    1080
GGGCTGGAAG TAAGGAAACA TGTAATGATA GGCGGACTCC CAGCACAGAA AAAAAGGTAG    1140
ATCTGAATGC TGATCCCCTG TGTGAGAGAA AAGAATGGAA TAAGCAGAAA CTGCCATGCT    1200
CAGAGAATCC TAGAGATACT GAAGATGTTC CTTGGATAAC ACTAAATAGC AGCATTCAGA    1260
AAGTTAATGA GTGGTTTTCC AGAAGTGATG AACTGTTAGG TTCTGATGAC TCACATGATG    1320
GGGAGTCTGA ATCAAATGCC AAAGTAGCTG ATGTATTGGA CGTTCTAAAT GAGGTAGATG    1380
AATATTCTGG TTCTTCAGAG AAAATAGACT TACTGGCCAG TGATCCTCAT GAGGCTTTAA    1440
TATGTAAAAG TGAAAGAGTT CACTCCAAAT CAGTAGAGAG TAATATTGAA GACAAAATAT    1500
TTGGGAAAAC CTATCGGAAG AAGGCAAGCC TCCCCAACTT AAGCCATGTA ACTGAAAATC    1560
TAATTATAGG AGCATTTGTT ACTGAGCCAC AGATAATACA GAGCGTCCC CTCACAAATA     1620
AATTAAAGCG TAAAAGGAGA CCTACATCAG GCCTTCATCC TGAGGATTTT ATCAAGAAAG    1680
CAGATTTGGC AGTTCAAAAG ACTCCTGAAA TGATAAATCA GGGAACTAAC CAAACGGAGC    1740
AGAATGGTCA AGTGATGAAT ATTACTAATA GTGGTCATGA GAATAAAACA AAGGTGATT     1800
CTATTCAGAA TGAGAAAAAT CCTAACCCAA TAGAATCACT CGAAAAAGAA TCTGCTTTCA    1860
AAACGAAAGC TGAACCTATA AGCAGCAGTA TAAGCAATAT GGAACTCGAA TTAAATATCC    1920
ACAATTCAAA AGCACCTAAA AAGAATAGGC TGAGGAGGAA GTCTTCTACC AGGCATATTC    1980
ATGCGCTTGA ACTAGTAGTC AGTAGAAATC TAAGCCCACC TAATTGTACT GAATTGCAAA    2040
TTGATAGTTG TTCTAGCAGT GAAGAGATAA AGAAAAAAA GTACAACCAA ATGCCAGTCA     2100
GGCACAGCAG AAACCTACAA CTCATGGAAG GTAAAGAACC TGCAACTGGA GCCAAGAAGA    2160
GTAACAAGCC AAATGAACAG ACAAGTAAAA GACATGACAG CGATACTTTC CCAGAGCTGA    2220
AGTTAACAAA TGCACCTGGT TCTTTTACTA AGTGTTCAAA TACCAGTGAA CTTAAAGAAT    2280
TTGTCAATCC TAGCCTTCCA AGAGAAGAAA AAGAAGAGAA ACTAGAAACA GTTAAAGTGT    2340
```

```
CTAATAATGC TGAAGACCCC AAAGATCTCA TGTTAAGTGG AGAAAGGGTT TTGCAAACTG      2400
AAAGATCTGT AGAGTAGCAG TATTTCATTG GTACCTGGTA CTGATTATGG CACTCAGGAA      2460
AGTATCTCGT TACTGGAAGT TAGCACTCTA GGGAAGGCAA AAACAGAACC AAATAAATGT      2520
GTGAGTCAGT GTGCAGCATT TGAAAACCCC AAGGGACTAA TTCATGGTTG TTCCAAAGAT      2580
AATAGAAATG ACACAGAAGG CTTTAAGTAT CCATTGGGAC ATGAAGTTAA CCACAGTCGG      2640
GAAACAAGCA TAGAAATGGA AGAAAGTGAA CTTGATGCTC AGTATTTGCA GAATACATTC      2700
AAGGTTTCAA AGCGCCAGTC ATTTGCTCCG TTTTCAAATC CAGGAAATGC AGAAGAGGAA      2760
TGTGCAACAT TCTCTGCCCA CTCTGGGTCC TTAAAGAAAC AAAGTCCAAA AGTCACTTTT      2820
GAATGTGAAC AAAAGGAAGA AAATCAAGGA AGAATGAGT CTAATATCAA GCCTGTACAG       2880
ACAGTTAATA TCACTGCAGG CTTTCCTGTG GTTGGTCAGA AAGATAAGCC AGTTGATAAT      2940
GCCAAATGTA GTATCAAAGG AGGCTCTAGG TTTTGTCTAT CATCTCAGTT CAGAGGCAAC      3000
GAAACTGGAC TCATTACTCC AAATAAACAT GGACTTTTAC AAAACCCATA TCGTATACCA      3060
CCACTTTTTC CCATCAAGTC ATTTGTTAAA ACTAAATGTA AGAAAAATCT GCTAGAGGAA      3120
AACTTTGAGG AACATTCAAT GTCACCTGAA AGAGAAATGG GAAATGAGAA CATTCCAAGT      3180
ACAGTGAGCA CAATTAGCCG TAATAACATT AGAGAAAATG TTTTTAAAGA AGCCAGCTCA      3240
AGCAATATTA ATGAAGTAGG TTCCAGTACT AATGAAGTGG GCTCCAGTAT TAATGAAATA      3300
GGTTCCAGTG ATGAAAACAT TCAAGCAGAA CTAGGTAGAA ACAGAGGGCC AAAATTGAAT      3360
GCTATGCTTA GATTAGGGGT TTTGCAACCT GAGGTCTATA AACAAAGTCT TCCTGGAAGT      3420
AATTGTAAGC ATCCTGAAAT AAAAAAGCAA GAATATGAAG AAGTAGTTCA GACTGTTAAT      3480
ACAGATTTCT CTCCATATCT GATTTCAGAT AACTTAGAAC AGCCTATGGG AAGTAGTCAT      3540
GCATCTCAGG TTTGTTCTGA GACACCTGAT GACCTGTTAG ATGATGGTGA AATAAAGGAA      3600
GATACTAGTT TTGCTGAAAA TGACATTAAG GAAAGTTCTG CTGTTTTTAG CAAAAGCGTC      3660
CAGAAAGGAG AGCTTAGCAG GAGTCCTAGC CCTTTCACCC ATACACATTT GGCTCAGGGT      3720
TACCGAAGAG GGGCCAAGAA ATTAGAGTCC TCAGAAGAGA ACTTATCTAG TGAGGATGAA      3780
GAGCTTCCCT GCTTCCAACA CTTGTTATTT GGTAAAGTAA ACAATATACC TTCTCAGTCT      3840
ACTAGGCATA GCACCGTTGC TACCGAGTGT CTGTCTAAGA ACACAGAGGA GAATTTATTA      3900
TCATTGAAGA ATAGCTTAAA TGACTGCAGT AACCAGGTAA TATTGGCAAA GGCATCTCAG      3960
GAACATCACC TTAGTGAGGA AACAAAATGT TCTGCTAGCT TGTTTTCTTC ACAGTGCAGT      4020
GAATTGGAAG ACTTGACTGC AAATACAAAC ACCCAGGATC CTTTCTTGAT TGGTTCTTCC      4080
AAACAAATGA GGCATCAGTC TGAAAGCCAG GGAGTTGGTC TGAGTGACAA GGAATTGGTT      4140
TCAGATGATG AAGAAAGAGG AACGGGCTTG GAAGAAAATA ATCAAGAAGA GCAAAGCATG      4200
GATTCAAACT TAGGTGAAGC AGCATCTGGG TGTGAGAGTG AAACAAGCGT CTCTGAAGAC      4260
TGCTCAGGGC TATCCTCTCA GAGTGACATT TTAACCACTC AGCAGAGGGA TACCATGCAA      4320
CATAACCTGA TAAAGCTCCA GCAGGAAATG GCTGAACTAG AAGCTGTGTT AGAACAGCAT      4380
GGGAGCCAGC CTTCTAACAG CTACCCTTCC ATCATAAGTG ACTCTTCTGC CCTTGAGGAC      4440
CTGCGAAATC CAGAACAAAG CACATCAGAA AAAGCAGTAT TAACTTCACA GAAAAGTAGT      4500
GAATACCCTA TAAGCCAGAA TCCAGAAGGC CTTTCTGCTG ACAAGTTTGA GGTGTCTGCA      4560
GATAGTTCTA CCAGTAAAAA TAAAGAACCA GGAGTGGAAA GGTCATCCCC TTCTAAATGC      4620
CCATCATTAG ATGATAGGTG GTACATGCAC AGTTGCTCTG GGAGTCTTCA GAATAGAAAC      4680
TACCCATCTC AAGAGGAGCT CATTAAGGTT GTTGATGTGG AGGAGCAACA GCTGGAAGAG      4740
```

```
TCTGGGCCAC  ACGATTTGAC  GGAAACATCT  TACTTGCCAA  GGCAAGATCT  AGAGGGAACC    4800

CCTTACCTGG  AATCTGGAAT  CAGCCTCTTC  TCTGATGACC  CTGAATCTGA  TCCTTCTGAA    4860

GACAGAGCCC  CAGAGTCAGC  TCGTGTTGGC  AACATACCAT  CTTCAACCTC  TGCATTGAAA    4920

GTTCCCCAAT  TGAAAGTTGC  AGAATCTGCC  CAGAGTCCAG  CTGCTGCTCA  TACTACTGAT    4980

ACTGCTGGGT  ATAATGCAAT  GGAAGAAAGT  GTGAGCAGGG  AGAAGCCAGA  ATTGACAGCT    5040

TCAACAGAAA  GGGTCAACAA  AAGAATGTCC  ATGGTGGTGT  CTGGCCTGAC  CCCAGAAGAA    5100

TTTATGCTCG  TGTACAAGTT  TGCCAGAAAA  CACCACATCA  CTTTAACTAA  TCTAATTACT    5160

GAAGAGACTA  CTCATGTTGT  TATGAAAACA  GATGCTGAGT  TTGTGTGTGA  ACGGACACTG    5220

AAATATTTTC  TAGGAATTGC  GGGAGGAAAA  TGGGTAGTTA  GCTATTTCTG  GGTGACCCAG    5280

TCTATTAAAG  AAAGAAAAAT  GCTGAATGAG  CATGATTTTG  AAGTCAGAGG  AGATGTGGTC    5340

AATGGAAGAA  ACCACCAAGG  TCCAAAGCGA  GCAAGAGAAT  CCCAGGACAG  AAAGATCTTC    5400

AGGGGCTAG   AAATCTGTTG  CTATGGGCCC  TTCACCAACA  TGCCCACAGA  TCAACTGGAA    5460

TGGATGGTAC  AGCTGTGTGG  TGCTTCTGTG  GTGAAGGAGC  TTTCATCATT  CACCCTTGGC    5520

ACAGGTGTCC  ACCCAATTGT  GGTTGTGCAG  CCAGATGCCT  GGACAGAGGA  CAATGGCTTC    5580

CATGCAATTG  GGCAGATGTG  TGAGGCACCT  GTGGTGACCC  GAGAGTGGGT  GTTGGACAGT    5640

GTAGCACTCT  ACCAGTGCCA  GGAGCTGGAC  ACCTACCTGA  TACCCCAGAT  CCCCCACAGC    5700

CACTACTGA                                                                5709
```

( 2 ) INFORMATION FOR SEQ ID NO:8:

( i ) SEQUENCE CHARACTERISTICS:
        ( A ) LENGTH: 5709 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

```
AGCTCGCTGA  GACTTCCTGG  ACCCCGCACC  AGGCTGTGGG  GTTTCTCAGA  TAACTGGGCC     60

CCTGCGCTCA  GGAGGCCTTC  ACCCTCTGCT  CTGGGTAAAG  TTCATTGGAA  CAGAAAGAAA    120

TGGATTTATC  TGCTCTTCGC  GTTGAAGAAG  TACAAAATGT  CATTAATGCT  ATGCAGAAAA    180

TCTTAGAGTG  TCCCATCTGT  CTGGAGTTGA  TCAAGGAACC  TGTCTCCACA  AAGTGTGACC    240

ACATATTTTG  CAAATTTTGC  ATGCTGAAAC  TTCTCAACCA  GAAGAAAGGG  CCTTCACAGT    300

GTCCTTTATG  TAAGAATGAT  ATAACCAAAA  GGAGCCTACA  AGAAAGTACG  AGATTTAGTC    360

AACTTGTTGA  AGAGCTATTG  AAAATCATTT  GTGCTTTTCA  GCTTGACACA  GGTTTGGAGT    420

ATGCAAACAG  CTATAATTTT  GCAAAAAAGG  AAAATAACTC  TCCTGAACAT  CTAAAAGATG    480

AAGTTTCTAT  CATCCAAAGT  ATGGGCTACA  GAAACCGTGC  CAAAAGACTT  CTACAGAGTG    540

AACCCGAAAA  TCCTTCCTTG  CAGGAAACCA  GTCTCAGTGT  CCAACTCTCT  AACCTTGGAA    600

CTGTGAGAAC  TCTGAGGACA  AAGCAGCGGA  TACAACCTCA  AAAGACGTCT  GTCTACATTG    660

AATTGGGATC  TGATTCTTCT  GAAGATACCG  TTAATAAGGC  AACTTATTGC  AGTGTGGGAG    720

ATCAAGAATT  GTTACAAATC  ACCCCTCAAG  GAACCAGGGA  TGAAATCAGT  TTGGATTCTG    780

CAAAAAAGGC  TGCTTGTGAA  TTTTCTGAGA  CGGATGTAAC  AAATACTGAA  CATCATCAAC    840

CCAGTAATAA  TGATTTGAAC  ACCACTGAGA  AGCGTGCAGC  TGAGAGGCAT  CCAGAAAAGT    900

ATCAGGGTAG  TTCTGTTTCA  AACTTGCATG  TGGAGCCATG  TGGCACAAAT  ACTCATGCCA    960
```

```
GCTCATTACA GCATGAGAAC AGCAGTTTAT TACTCACTAA AGACAGAATG AATGTAGAAA    1020
AGGCTGAATT CTGTAATAAA AGCAAACAGC CTGGCTTAGC AAGGAGCCAA CATAACAGAT    1080
GGGCTGGAAG TAAGGAAACA TGTAATGATA GGCGGACTCC CAGCACAGAA AAAAAGGTAG    1140
ATCTGAATGC TGATCCCCTG TGTGAGAGAA AAGAATGGAA TAAGCAGAAA CTGCCATGCT    1200
CAGAGAATCC TAGAGATACT GAAGATGTTC CTTGGATAAC ACTAAATAGC AGCATTCAGA    1260
AAGTTAATGA GTGGTTTTCC AGAAGTGATG AACTGTTAGG TTCTGATGAC TCACATGATG    1320
GGGAGTCTGA ATCAAATGCC AAAGTAGCTG ATGTATTGGA CGTTCTAAAT GAGGTAGATG    1380
AATATTCTGG TTCTTCAGAG AAAATAGACT TACTGGCCAG TGATCCTCAT GAGGCTTTAA    1440
TATGTAAAAG TGAAAGAGTT CACTCCAAAT CAGTAGAGAG TAATATTGAA GACAAAATAT    1500
TTGGGAAAAC CTATCGGAAG AAGGCAAGCC TCCCCAACTT AAGCCATGTA ACTGAAAATC    1560
TAATTATAGG AGCATTTGTT ACTGAGCCAC AGATAATACA AGAGCGTCCC CTCACAAATA    1620
AATTAAAGCG TAAAAGGAGA CCTACATCAG GCCTTCATCC TGAGGATTTT ATCAAGAAAG    1680
CAGATTTGGC AGTTCAAAAG ACTCCTGAAA TGATAAATCA GGGAACTAAC CAAACGGAGC    1740
AGAATGGTCA AGTGATGAAT ATTACTAATA GTGGTCATGA GAATAAAACA AAAGGTGATT    1800
CTATTCAGAA TGAGAAAAAT CCTAACCCAA TAGAATCACT CGAAAAAGAA TCTGCTTTCA    1860
AAACGAAAGC TGAACCTATA AGCAGCAGTA TAAGCAATAT GGAACTCGAA TTAAATATCC    1920
ACAATTCAAA AGCACCTAAA AGAATAGGC TGAGGAGGAA GTCTTCTACC AGGCATATTC    1980
ATGCGCTTGA ACTAGTAGTC AGTAGAAATC TAAGCCCACC TAATTGTACT GAATTGCAAA    2040
TTGATAGTTG TTCTAGCAGT GAAGAGATAA AGAAAAAAAA GTACAACCAA ATGCCAGTCA    2100
GGCACAGCAG AAACCTACAA CTCATGGAAG GTAAAGAACC TGCAACTGGA GCCAAGAAGA    2160
GTAACAAGCC AAATGAACAG ACAAGTAAAA GACATGACAG CGATACTTTC CCAGAGCTGA    2220
AGTTAACAAA TGCACCTGGT TCTTTTACTA AGTGTTCAAA TACCAGTGAA CTTAAAGAAT    2280
TTGTCAATCC TAGCCTTCCA AGAGAAGAAA AGAAGAGAA ACTAGAAACA GTTAAAGTGT    2340
CTAATAATGC TGAAGACCCC AAAGATCTCA TGTTAAGTGG AGAAAGGGTT TTGCAAACTG    2400
AAAGATCTGT AGAGAGTAGC AGTATTTCAT TGGTACCTGG TACTGATTAT GGCACTCAGG    2460
AAAGTATCTC GTTACTGGAA GTTAGCACTC TAGGGAAGGC AAAAACAGAA CCAAATAAAT    2520
GTGTGAGTCA GTGTGCAGCA TTTGAAAACC CCAAGGGACT AATTCATGGT TGTTCCAAAG    2580
ATAATAGAAA TGACACAGAA GGCTTTAAGT ATCCATTGGG ACATGAAGTT AACCACAGTC    2640
GGGAAACAAG CATAGAAATG GAAGAAAGTG AACTTGATGC TCAGTATTTG CAGAATACAT    2700
TCAAGGTTTC AAAGCGCCAG TCATTTGCTC CGTTTTCAAA TCCAGGAAAT GCAGAAGAGG    2760
AATGTGCAAC ATTCTCTGCC CACTCTGGGT CCTTAAAGAC AAAGTCCAAA AGTCACTTTT    2820
GAATGTGAAC AAAAGGAAGA AAATCAAGGA AGAATGAGT CTAATATCAA GCCTGTACAG    2880
ACAGTTAATA TCACTGCAGG CTTTCCTGTG GTTGGTCAGA AAGATAAGCC AGTTGATAAT    2940
GCCAAATGTA GTATCAAAGG AGGCTCTAGG TTTTGTCTAT CATCTCAGTT CAGAGGCAAC    3000
GAAACTGGAC TCATTACTCC AAATAAACAT GGACTTTTAC AAAACCCATA TCGTATACCA    3060
CCACTTTTTC CCATCAAGTC ATTTGTTAAA ACTAAATGTA AGAAAAATCT GCTAGAGGAA    3120
AACTTTGAGG AACATTCAAT GTCACCTGAA AGAGAAATGG GAAATGAGAA CATTCCAAGT    3180
ACAGTGAGCA CAATTAGCCG TAATAACATT AGAGAAAATG TTTTTAAAGA AGCCAGCTCA    3240
AGCAATATTA ATGAAGTAGG TTCCAGTACT AATGAAGTGG GCTCCAGTAT TAATGAAATA    3300
GGTTCCAGTG ATGAAAACAT TCAAGCAGAA CTAGGTAGAA ACAGAGGGCC AAAATTGAAT    3360
```

| | | | | | | |
|---|---|---|---|---|---|---|
| GCTATGCTTA | GATTAGGGGT | TTTGCAACCT | GAGGTCTATA | AACAAAGTCT | TCCTGGAAGT | 3420 |
| AATTGTAAGC | ATCCTGAAAT | AAAAAAGCAA | GAATATGAAG | AAGTAGTTCA | GACTGTTAAT | 3480 |
| ACAGATTTCT | CTCCATATCT | GATTTCAGAT | AACTTAGAAC | AGCCATGGG | AAGTAGTCAT | 3540 |
| GCATCTCAGG | TTTGTTCTGA | GACACCTGAT | GACCTGTTAG | ATGATGGTGA | AATAAAGGAA | 3600 |
| GATACTAGTT | TTGCTGAAAA | TGACATTAAG | GAAAGTTCTG | CTGTTTTTAG | CAAAAGCGTC | 3660 |
| CAGAAAGGAG | AGCTTAGCAG | GAGTCCTAGC | CCTTTCACCC | ATACACATTT | GGCTCAGGGT | 3720 |
| TACCGAAGAG | GGGCCAAGAA | ATTAGAGTCC | TCAGAAGAGA | ACTTATCTAG | TGAGGATGAA | 3780 |
| GAGCTTCCCT | GCTTCCAACA | CTTGTTATTT | GGTAAAGTAA | ACAATATACC | TTCTCAGTCT | 3840 |
| ACTAGGCATA | GCACCGTTGC | TACCGAGTGT | CTGTCTAAGA | ACACAGAGGA | GAATTTATTA | 3900 |
| TCATTGAAGA | ATAGCTTAAA | TGACTGCAGT | AACCAGGTAA | TATTGGCAAA | GGCATCTCAG | 3960 |
| GAACATCACC | TTAGTGAGGA | AACAAAATGT | TCTGCTAGCT | TGTTTTCTTC | ACAGTGCAGT | 4020 |
| GAATTGGAAG | ACTTGACTGC | AAATACAAAC | ACCCAGGATC | CTTTCTTGAT | TGGTTCTTCC | 4080 |
| AAACAAATGA | GGCATCAGTC | TGAAAGCCAG | GGAGTTGGTC | TGAGTGACAA | GGAATTGGTT | 4140 |
| TCAGATGATG | AAGAAGAGG | AACGGGCTTG | GAAGAAAATA | ATCAAGAAGA | GCAAAGCATG | 4200 |
| GATTCAAACT | TAGGTGAAGC | AGCATCTGGG | TGTGAGAGTG | AAACAAGCGT | CTCTGAAGAC | 4260 |
| TGCTCAGGGC | TATCCTCTCA | GAGTGACATT | TTAACCACTC | AGCAGAGGGA | TACCATGCAA | 4320 |
| CATAACCTGA | TAAAGCTCCA | GCAGGAAATG | GCTGAACTAG | AAGCTGTGTT | AGAACAGCAT | 4380 |
| GGGAGCCAGC | CTTCTAACAG | CTACCCTTCC | ATCATAAGTG | ACTCTTCTGC | CCTTGAGGAC | 4440 |
| CTGCGAAATC | CAGAACAAAG | CACATCAGAA | AAAGCAGTAT | TAACTTCACA | GAAAAGTAGT | 4500 |
| GAATACCCTA | TAAGCCAGAA | TCCAGAAGGC | CTTTCTGCTG | ACAAGTTTGA | GGTGTCTGCA | 4560 |
| GATAGTTCTA | CCAGTAAAAA | TAAAGAACCA | GGAGTGGAAA | GGTCATCCCC | TTCTAAATGC | 4620 |
| CCATCATTAG | ATGATAGGTG | GTACATGCAC | AGTTGCTCTG | GGAGTCTTCA | GAATAGAAAC | 4680 |
| TACCCATCTC | AAGAGGAGCT | CATTAAGGTT | GTTGATGTGG | AGGAGCAACA | GCTGGAAGAG | 4740 |
| TCTGGGCCAC | ACGATTTGAC | GGAAACATCT | TACTTGCCAA | GGCAAGATCT | AGAGGGAACC | 4800 |
| CCTTACCTGG | AATCTGGAAT | CAGCCTCTTC | TCTGATGACC | CTGAATCTGA | TCCTTCTGAA | 4860 |
| GACAGAGCCC | CAGAGTCAGC | TCGTGTTGGC | AACATACCAT | CTTCAACCTC | TGCATTGAAA | 4920 |
| GTTCCCCAAT | TGAAAGTTGC | AGAATCTGCC | CAGAGTCCAG | CTGCTGCTCA | TACTACTGAT | 4980 |
| ACTGCTGGGT | ATAATGCAAT | GGAAGAAAGT | GTGAGCAGGG | AGAAGCCAGA | ATTGACAGCT | 5040 |
| TCAACAGAAA | GGGTCAACAA | AAGAATGTCC | ATGGTGGTGT | CTGGCCTGAC | CCCAGAAGAA | 5100 |
| TTTATGCTCG | TGTACAAGTT | TGCCAGAAAA | CACCACATCA | CTTTAACTAA | TCTAATTACT | 5160 |
| GAAGAGACTA | CTCATGTTGT | TATGAAAACA | GATGCTGAGT | TTGTGTGTGA | ACGGACACTG | 5220 |
| AAATATTTTC | TAGGAATTGC | GGGAGGAAAA | TGGGTAGTTA | GCTATTTCTG | GGTGACCCAG | 5280 |
| TCTATTAAAG | AAAGAAAAAT | GCTGAATGAG | CATGATTTTG | AAGTCAGAGG | AGATGTGGTC | 5340 |
| AATGGAAGAA | ACCACCAAGG | TCCAAAGCGA | GCAAGAGAAT | CCCAGGACAG | AAAGATCTTC | 5400 |
| AGGGGGCTAG | AAATCTGTTG | CTATGGGCCC | TTCACCAACA | TGCCCACAGA | TCAACTGGAA | 5460 |
| TGGATGGTAC | AGCTGTGTGG | TGCTTCTGTG | GTGAAGGAGC | TTTCATCATT | CACCCTTGGC | 5520 |
| ACAGGTGTCC | ACCCAATTGT | GGTTGTGCAG | CCAGATGCCT | GGACAGAGGA | CAATGGCTTC | 5580 |
| CATGCAATTG | GGCAGATGTG | TGAGGCACCT | GTGGTGACCC | GAGAGTGGGT | GTTGGACAGT | 5640 |
| GTAGCACTCT | ACCAGTGCCA | GGAGCTGGAC | ACCTACCTGA | TACCCCAGAT | CCCCCACAGC | 5700 |
| CACTACTGA | | | | | | 5709 |

( 2 ) INFORMATION FOR SEQ ID NO:9:

( i ) SEQUENCE CHARACTERISTICS:
        ( A ) LENGTH: 5709 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

```
AGCTCGCTGA  GACTTCCTGG  ACCCCGCACC  AGGCTGTGGG  GTTTCTCAGA  TAACTGGGCC     60
CCTGCGCTCA  GGAGGCCTTC  ACCCTCTGCT  CTGGGTAAAG  TTCATTGGAA  CAGAAAGAAA    120
TGGATTTATC  TGCTCTTCGC  GTTGAAGAAG  TACAAAATGT  CATTAATGCT  ATGCAGAAAA    180
TCTTAGAGTG  TCCCATCTGT  CTGGAGTTGA  TCAAGGAACC  TGTCTCCACA  AAGTGTGACC    240
ACATATTTTG  CAAATTTTGC  ATGCTGAAAC  TTCTCAACCA  GAAGAAAGGG  CCTTCACAGT    300
GTCCTTTATG  TAAGAATGAT  ATAACCAAAA  GGAGCCTACA  AGAAAGTACG  AGATTTAGTC    360
AACTTGTTGA  AGAGCTATTG  AAAATCATTT  GTGCTTTTCA  GCTTGACACA  GGTTTGGAGT    420
ATGCAAACAG  CTATAATTTT  GCAAAAAAGG  AAAATAACTC  TCCTGAACAT  CTAAAAGATG    480
AAGTTTCTAT  CATCCAAAGT  ATGGGCTACA  GAAACCGTGC  CAAAAGACTT  CTACAGAGTG    540
AACCCGAAAA  TCCTTCCTTG  CAGGAAACCA  GTCTCAGTGT  CCAACTCTCT  AACCTTGGAA    600
CTGTGAGAAC  TCTGAGGACA  AAGCAGCGGA  TACAACCTCA  AAAGACGTCT  GTCTACATTG    660
AATTGGGATC  TGATTCTTCT  GAAGATACCG  TTAATAAGGC  AACTTATTGC  AGTGTGGGAG    720
ATCAAGAATT  GTTACAAATC  ACCCCTCAAG  GAACCAGGGA  TGAAATCAGT  TTGGATTCTG    780
CAAAAAAGGC  TGCTTGTGAA  TTTTCTGAGA  CGGATGTAAC  AAATACTGAA  CATCATCAAC    840
CCAGTAATAA  TGATTTGAAC  ACCACTGAGA  AGCGTGCAGC  TGAGAGGCAT  CCAGAAAAGT    900
ATCAGGGTAG  TTCTGTTTCA  AACTTGCATG  TGGAGCCATG  TGGCACAAAT  ACTCATGCCA    960
GCTCATTACA  GCATGAGAAC  AGCAGTTTAT  TACTCACTAA  AGACAGAATG   AATGTAGAAA   1020
AGGCTGAATT  CTGTAATAAA  AGCAAACAGC  CTGGCTTAGC  AAGGAGCCAA  CATAACAGAT   1080
GGGCTGGAAG  TAAGGAAACA  TGTAATGATA  GGCGGACTCC  CAGCACAGAA  AAAAAGGTAG   1140
ATCTGAATGC  TGATCCCCTG  TGTGAGAGAA  AAGAATGGAA  TAAGCAGAAA  CTGCCATGCT   1200
CAGAGAATCC  TAGAGATACT  GAAGATGTTC  CTTGGATAAC  ACTAAATAGC  AGCATTCAGA   1260
AAGTTAATGA  GTGGTTTTCC  AGAAGTGATG  AACTGTTAGG  TTCTGATGAC  TCACATGATG   1320
GGGAGTCTGA  ATCAAATGCC  AAAGTAGCTG  ATGTATTGGA  CGTTCTAAAT  GAGGTAGATG   1380
AATATTCTGG  TTCTTCAGAG  AAAATAGACT  TACTGGCCAG  TGATCCTCAT  GAGGCTTTAA   1440
TATGTAAAAG  TGAAAGAGTT  CACTCCAAAT  CAGTAGAGAG  TAATATTGAA  GACAAAATAT   1500
TTGGGAAAAC  CTATCGGAAG  AAGGCAAGCC  TCCCCAACTT  AAGCCATGTA  ACTGAAAATC   1560
TAATTATAGG  AGCATTTGTT  ACTGAGCCAC  AGATAATACA  AGAGCGTCCC  CTCACAAATA   1620
AATTAAAGCG  TAAAAGGAGA  CCTACATCAG  GCCTTCATCC  TGAGGATTTT  ATCAAGAAAG   1680
CAGATTTGGC  AGTTCAAAAG  ACTCCTGAAA  TGATAAATCA  GGGAACTAAC  CAAACGGAGC   1740
AGAATGGTCA  AGTGATGAAT  ATTACTAATA  GTGGTCATGA  GAATAAAACA  AAAGGTGATT   1800
CTATTCAGAA  TGAGAAAAAT  CCTAACCCAA  TAGAATCACT  CGAAAAAGAA  TCTGCTTTCA   1860
AAACGAAAGC  TGAACCTATA  AGCAGCAGTA  TAAGCAATAT  GGAACTCGAA  TTAAATATCC   1920
ACAATTCAAA  AGCACCTAAA  AAGAATAGGC  TGAGGAGGAA  GTCTTCTACC  AGGCATATTC   1980
ATGCGCTTGA  ACTAGTAGTC  AGTAGAAATC  TAAGCCCACC  TAATTGTACT  GAATTGCAAA   2040
```

```
TTGATAGTTG  TTCTAGCAGT  GAAGAGATAA  AGAAAAAAAA  GTACAACCAA  ATGCCAGTCA   2100
GGCACAGCAG  AAACCTACAA  CTCATGGAAG  GTAAAGAACC  TGCAACTGGA  GCCAAGAAGA   2160
GTAACAAGCC  AAATGAACAG  ACAAGTAAAA  GACATGACAG  CGATACTTTC  CCAGAGCTGA   2220
AGTTAACAAA  TGCACCTGGT  TCTTTTACTA  AGTGTTCAAA  TACCAGTGAA  CTTAAAGAAT   2280
TTGTCAATCC  TAGCCTTCCA  AGAGAAGAAA  AAGAAGAGAA  ACTAGAAACA  GTTAAAGTGT   2340
CTAATAATGC  TGAAGACCCC  AAAGATCTCA  TGTTAAGTGG  AGAAAGGGTT  TTGCAAACTG   2400
AAAGATCTGT  AGAGAGTAGC  AGTATTTCAT  TGGTACCTGG  TACTGATTAT  GGCACTCAGG   2460
AAAGTATCTC  GTTACTGGAA  GTTAGCACTC  TAGGGAAGGC  AAAAACAGAA  CCAAATAAAT   2520
GTGTGAGTCA  GTGTGCAGCA  TTTGAAAACC  CCAAGGGACT  AATTCATGGT  TGTTCCAAAG   2580
ATAATAGAAA  TGACACAGAA  GGCTTTAAGT  ATCCATTGGG  ACATGAAGTT  AACCACAGTC   2640
GGGAAACAAG  CATAGAAATG  GAAGAAAGTG  AACTTGATGC  TCAGTATTTG  CAGAATACAT   2700
TCAAGGTTTC  AAAGCGCCAG  TCATTTGCTC  CGTTTTCAAA  TCCAGGAAAT  GCAGAAGAGG   2760
AATGTGCAAC  ATTCTCTGCC  CACTCTGGGT  CCTTAAAGAA  ACAAAGTCCA  AAAGTCACTT   2820
TTGAATGTGA  ACAAAAGGAA  GAAAATCAAG  GAAAGAATGA  GTAATATCAA  GCCTGTACAG   2880
ACAGTTAATA  TCACTGCAGG  CTTTCCTGTG  GTTGGTCAGA  AAGATAAGCC  AGTTGATAAT   2940
GCCAAATGTA  GTATCAAAGG  AGGCTCTAGG  TTTTGTCTAT  CATCTCAGTT  CAGAGGCAAC   3000
GAAACTGGAC  TCATTACTCC  AAATAAACAT  GGACTTTTAC  AAAACCCATA  TCGTATACCA   3060
CCACTTTTTC  CCATCAAGTC  ATTTGTTAAA  ACTAAATGTA  AGAAAAATCT  GCTAGAGGAA   3120
AACTTTGAGG  AACATTCAAT  GTCACCTGAA  AGAGAAATGG  GAAATGAGAA  CATTCCAAGT   3180
ACAGTGAGCA  CAATTAGCCG  TAATAACATT  AGAGAAAATG  TTTTTAAAGA  AGCCAGCTCA   3240
AGCAATATTA  ATGAAGTAGG  TTCCAGTACT  AATGAAGTGG  GCTCCAGTAT  TAATGAAATA   3300
GGTTCCAGTG  ATGAAAACAT  TCAAGCAGAA  CTAGGTAGAA  ACAGAGGGCC  AAAATTGAAT   3360
GCTATGCTTA  GATTAGGGGT  TTTGCAACCT  GAGGTCTATA  AACAAAGTCT  TCCTGGAAGT   3420
AATTGTAAGC  ATCCTGAAAT  AAAAAAGCAA  GAATATGAAG  AAGTAGTTCA  GACTGTTAAT   3480
ACAGATTTCT  CTCCATATCT  GATTTCAGAT  AACTTAGAAC  AGCCTATGGG  AAGTAGTCAT   3540
GCATCTCAGG  TTTGTTCTGA  GACACCTGAT  GACCTGTTAG  ATGATGGTGA  AATAAAGGAA   3600
GATACTAGTT  TTGCTGAAAA  TGACATTAAG  GAAAGTTCTG  CTGTTTTTAG  CAAAAGCGTC   3660
CAGAAAGGAG  AGCTTAGCAG  GAGTCCTAGC  CCTTTCACCC  ATACACATTT  GGCTCAGGGT   3720
TACCGAAGAG  GGGCCAAGAA  ATTAGAGTCC  TCAGAAGAGA  ACTTATCTAG  TGAGGATGAA   3780
GAGCTTCCCT  GCTTCCAACA  CTTGTTATTT  GGTAAAGTAA  ACAATATACC  TTCTCAGTCT   3840
ACTAGGCATA  GCACCGTTGC  TACCGAGTGT  CTGTCTAAGA  ACACAGAGGA  GAATTTATTA   3900
TCATTGAAGA  ATAGCTTAAA  TGACTGCAGT  AACCAGGTAA  TATTGGCAAA  GGCATCTCAG   3960
GAACATCACC  TTAGTGAGGA  AACAAAATGT  TCTGCTAGCT  TGTTTTCTTC  ACAGTGCAGT   4020
GAATTGGAAG  ACTTGACTGC  AAATACAAAC  ACCCAGGATC  CTTTCTTGAT  TGGTTCTTCC   4080
AAACAAATGA  GGCATCAGTC  TGAAAGCCAG  GGAGTTGGTC  TGAGTGACAA  GGAATTGGTT   4140
TCAGATGATG  AAGAAGAGG  AACGGGCTTG  GAAGAAAATA  ATCAAGAAGA  GCAAAGCATG   4200
GATTCAAACT  TAGGTGAAGC  AGCATCTGGG  TGTGAGAGTG  AAACAAGCGT  CTCTGAAGAC   4260
TGCTCAGGGC  TATCCTCTCA  GAGTGACATT  TTAACCACTC  AGCAGAGGGA  TACCATGCAA   4320
CATAACCTGA  TAAAGCTCCA  GCAGGAAATG  GCTGAACTAG  AAGCTGTGTT  AGAACAGCAT   4380
GGGAGCCAGC  CTTCTAACAG  CTACCCTTCC  ATCATAAGTG  ACTCTTCTGC  CCTTGAGGAC   4440
```

| | | | | | | |
|---|---|---|---|---|---|---|
| CTGCGAAATC | CAGAACAAAG | CACATCAGAA | AAAGCAGTAT | TAACTTCACA | GAAAAGTAGT | 4500 |
| GAATACCCTA | TAAGCCAGAA | TCCAGAAGGC | CTTTCTGCTG | ACAAGTTTGA | GGTGTCTGCA | 4560 |
| GATAGTTCTA | CCAGTAAAAA | TAAAGAACCA | GGAGTGGAAA | GGTCATCCCC | TTCTAAATGC | 4620 |
| CCATCATTAG | ATGATAGGTG | GTACATGCAC | AGTTGCTCTG | GGAGTCTTCA | GAATAGAAAC | 4680 |
| TACCCATCTC | AAGAGGAGCT | CATTAAGGTT | GTTGATGTGG | AGGAGCAACA | GCTGGAAGAG | 4740 |
| TCTGGGCCAC | ACGATTTGAC | GGAAACATCT | TACTTGCCAA | GGCAAGATCT | AGAGGGAACC | 4800 |
| CCTTACCTGG | AATCTGGAAT | CAGCCTCTTC | TCTGATGACC | CTGAATCTGA | TCCTTCTGAA | 4860 |
| GACAGAGCCC | CAGAGTCAGC | TCGTGTTGGC | AACATACCAT | CTTCAACCTC | TGCATTGAAA | 4920 |
| GTTCCCCAAT | TGAAAGTTGC | AGAATCTGCC | CAGAGTCCAG | CTGCTGCTCA | TACTACTGAT | 4980 |
| ACTGCTGGGT | ATAATGCAAT | GGAAGAAAGT | GTGAGCAGGG | AGAAGCCAGA | ATTGACAGCT | 5040 |
| TCAACAGAAA | GGGTCAACAA | AGAATGTCC | ATGGTGGTGT | CTGGCCTGAC | CCAGAAGAA | 5100 |
| TTTATGCTCG | TGTACAAGTT | TGCCAGAAAA | CACCACATCA | CTTTAACTAA | TCTAATTACT | 5160 |
| GAAGAGACTA | CTCATGTTGT | TATGAAAACA | GATGCTGAGT | TTGTGTGTGA | ACGGACACTG | 5220 |
| AAATATTTTC | TAGGAATTGC | GGGAGGAAAA | TGGGTAGTTA | GCTATTTCTG | GGTGACCCAG | 5280 |
| TCTATTAAAG | AAAGAAAAAT | GCTGAATGAG | CATGATTTTG | AAGTCAGAGG | AGATGTGGTC | 5340 |
| AATGGAAGAA | ACCACCAAGG | TCCAAAGCGA | GCAAGAGAAT | CCCAGGACAG | AAAGATCTTC | 5400 |
| AGGGGGCTAG | AAATCTGTTG | CTATGGGCCC | TTCACCAACA | TGCCCACAGA | TCAACTGGAA | 5460 |
| TGGATGGTAC | AGCTGTGTGG | TGCTTCTGTG | GTGAAGGAGC | TTTCATCATT | CACCCTTGGC | 5520 |
| ACAGGTGTCC | ACCCAATTGT | GGTTGTGCAG | CCAGATGCCT | GGACAGAGGA | CAATGGCTTC | 5580 |
| CATGCAATTG | GGCAGATGTG | TGAGGCACCT | GTGGTGACCC | GAGAGTGGGT | GTTGGACAGT | 5640 |
| GTAGCACTCT | ACCAGTGCCA | GGAGCTGGAC | ACCTACCTGA | TACCCCAGAT | CCCCCACAGC | 5700 |
| CACTACTGA | | | | | | 5709 |

( 2 ) INFORMATION FOR SEQ ID NO:10:

( i ) SEQUENCE CHARACTERISTICS:
( A ) LENGTH: 5711 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:10:

| | | | | | | |
|---|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAAGACGTCT | GTCTACATTG | 660 |

| | | | | | | |
|---|---|---|---|---|---|---|
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAAGGTAG | 1140 |
| ATCTGAATGC | TGATCCCCTG | TGTGAGAGAA | AAGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |
| ACAATTCAAA | AGCACCTAAA | AAGAATAGGC | TGAGGAGGAA | GTCTTCTACC | AGGCATATTC | 1980 |
| ATGCGCTTGA | ACTAGTAGTC | AGTAGAAATC | TAAGCCCACC | TAATTGTACT | GAATTGCAAA | 2040 |
| TTGATAGTTG | TTCTAGCAGT | GAAGAGATAA | AGAAAAAAA | GTACAACCAA | ATGCCAGTCA | 2100 |
| GGCACAGCAG | AAACCTACAA | CTCATGGAAG | GTAAAGAACC | TGCAACTGGA | GCCAAGAAGA | 2160 |
| GTAACAAGCC | AAATGAACAG | ACAAGTAAAA | GACATGACAG | CGATACTTTC | CCAGAGCTGA | 2220 |
| AGTTAACAAA | TGCACCTGGT | TCTTTTACTA | AGTGTTCAAA | TACCAGTGAA | CTTAAAGAAT | 2280 |
| TTGTCAATCC | TAGCCTTCCA | AGAGAAGAAA | AAGAAGAGAA | ACTAGAAACA | GTTAAAGTGT | 2340 |
| CTAATAATGC | TGAAGACCCC | AAAGATCTCA | TGTTAAGTGG | AGAAAGGGTT | TTGCAAACTG | 2400 |
| AAAGATCTGT | AGAGAGTAGC | AGTATTTCAT | TGGTACCTGG | TACTGATTAT | GGCACTCAGG | 2460 |
| AAAGTATCTC | GTTACTGGAA | GTTAGCACTC | TAGGGAAGGC | AAAAACAGAA | CCAAATAAAT | 2520 |
| GTGTGAGTCA | GTGTGCAGCA | TTTGAAAACC | CCAAGGGACT | AATTCATGGT | TGTTCCAAAG | 2580 |
| ATAATAGAAA | TGACACAGAA | GGCTTTAAGT | ATCCATTGGG | ACATGAAGTT | AACCACAGTC | 2640 |
| GGGAAACAAG | CATAGAAATG | GAAGAAAGTG | AACTTGATGC | TCAGTATTTG | CAGAATACAT | 2700 |
| TCAAGGTTTC | AAAGCGCCAG | TCATTTGCTC | CGTTTTCAAA | TCCAGGAAAT | GCAGAAGAGG | 2760 |
| AATGTGCAAC | ATTCTCTGCC | CACTCTGGGT | CCTTAAAGAA | ACAAAGTCCA | AAAGTCACTT | 2820 |
| TTGAATGTGA | ACAAAAGGAA | GAAAATCAAG | GAAAGAATGA | GTCTAATATC | AAGCCTGTAC | 2880 |
| AGACAGTTAA | TATCACTGCA | GGCTTTCCTG | TGGTTGGTCA | GAAAGATAAG | CCAGTTGATA | 2940 |
| ATGCCAAATG | TAGTATCAAA | GGAGGCTCTA | GGTTTTGTCT | ATCATCTCAG | TTCAGAGGCA | 3000 |
| ACGAAACTGG | ACTCATTACT | CCAAATAAAC | ATGGACTTTT | ACAAAACCCA | TATCGTATAC | 3060 |

```
CACCACTTTT TCCCATCAAG TCATTTGTTA AAACTAAATG TAAGAAAAAT CTGCTAGAGG    3120
AAAACTTTGA GGAACATTCA ATGTCACCTG AAAGAGAAAT GGGAAATGAG AACATTCCAA    3180
GTACAGTGAG CACAATTAGC CGTAATAACA TTAGAGAAAA TGTTTTTAAA GAAGCCAGCT    3240
CAAGCAATAT TAATGAAGTA GGTTCCAGTA CTAATGAAGT GGGCTCCAGT ATTAATGAAA    3300
TAGGTTCCAG TGATGAAAAC ATTCAAGCAG AACTAGGTAG AAACAGAGGG CCAAAATTGA    3360
ATGCTATGCT TAGATTAGGG GTTTTGCAAC CTGAGGTCTA TAAACAAAGT CTTCCTGGAA    3420
GTAATTGTAA GCATCCTGAA ATAAAAAGC AAGAATATGA AGAAGTAGTT CAGACTGTTA    3480
ATACAGATTT CTCTCCATAT CTGATTTCAG ATAACTTAGA ACAGCCTATG GGAAGTAGTC    3540
ATGCATCTCA GGTTTGTTCT GAGACACCTG ATGACCTGTT AGATGATGGT GAAATAAAGG    3600
AAGATACTAG TTTTGCTGAA AATGACATTA AGGAAAGTTC TGCTGTTTTT AGCAAAAGCG    3660
TCCAGAAAGG AGAGCTTAGC AGGAGTCCTA GCCCTTTCAC CCATACACAT TTGGCTCAGG    3720
GTTACTGAAG AGGGGCCAAG AAATTAGAGT CCTCAGAAGA GAACTTATCT AGTGAGGATG    3780
AAGAGCTTCC CTGCTTCCAA CACTTGTTAT TTGGTAAAGT AAACAATATA CCTTCTCAGT    3840
CTACTAGGCA TAGCACCGTT GCTACCGAGT GTCTGTCTAA GAACACAGAG GAGAATTTAT    3900
TATCATTGAA GAATAGCTTA AATGACTGCA GTAACCAGGT AATATTGGCA AAGGCATCTC    3960
AGGAACATCA CCTTAGTGAG GAAACAAAAT GTTCTGCTAG CTTGTTTTCT TCACAGTGCA    4020
GTGAATTGGA AGACTTGACT GCAAATACAA ACACCCAGGA TCCTTTCTTG ATTGGTTCTT    4080
CCAAACAAAT GAGGCATCAG TCTGAAAGCC AGGGAGTTGG TCTGAGTGAC AAGGAATTGG    4140
TTTCAGATGA TGAAGAAAGA GGAACGGGCT TGGAAGAAAA TAATCAAGAA GAGCAAAGCA    4200
TGGATTCAAA CTTAGGTGAA GCAGCATCTG GGTGTGAGAG TGAAACAAGC GTCTCTGAAG    4260
ACTGCTCAGG GCTATCCTCT CAGAGTGACA TTTTAACCAC TCAGCAGAGG GATACCATGC    4320
AACATAACCT GATAAAGCTC CAGCAGGAAA TGGCTGAACT AGAAGCTGTG TTAGAACAGC    4380
ATGGGAGCCA GCCTTCTAAC AGCTACCCTT CCATCATAAG TGACTCTTCT GCCCTTGAGG    4440
ACCTGCGAAA TCCAGAACAA AGCACATCAG AAAAAGCAGT ATTAACTTCA CAGAAAAGTA    4500
GTGAATACCC TATAAGCCAG AATCCAGAAG GCCTTTCTGC TGACAAGTTT GAGGTGTCTG    4560
CAGATAGTTC TACCAGTAAA AATAAAGAAC CAGGAGTGGA AAGGTCATCC CCTTCTAAAT    4620
GCCCATCATT AGATGATAGG TGGTACATGC ACAGTTGCTC TGGGAGTCTT CAGAATAGAA    4680
ACTACCCATC TCAAGAGGAG CTCATTAAGG TTGTTGATGT GGAGGAGCAA CAGCTGGAAG    4740
AGTCTGGGCC ACACGATTTG ACGGAAACAT CTTACTTGCC AAGGCAAGAT CTAGAGGGAA    4800
CCCCTTACCT GGAATCTGGA ATCAGCCTCT TCTCTGATGA CCCTGAATCT GATCCTTCTG    4860
AAGACAGAGC CCCAGAGTCA GCTCGTGTTG GCAACATACC ATCTTCAACC TCTGCATTGA    4920
AAGTTCCCCA ATTGAAAGTT GCAGAATCTG CCCAGAGTCC AGCTGCTGCT CATACTACTG    4980
ATACTGCTGG GTATAATGCA ATGGAAGAAA GTGTGAGCAG GGAGAAGCCA GAATTGACAG    5040
CTTCAACAGA AAGGGTCAAC AAAAGAATGT CCATGGTGGT GTCTGGCCTG ACCCCAGAAG    5100
AATTTATGCT CGTGTACAAG TTTGCCAGAA AACACCACAT CACTTTAACT AATCTAATTA    5160
CTGAAGAGAC TACTCATGTT GTTATGAAAA CAGATGCTGA GTTTGTGTGT GAACGGACAC    5220
TGAAATATTT TCTAGGAATT GCGGGAGGAA AATGGGTAGT TAGCTATTTC TGGGTGACCC    5280
AGTCTATTAA AGAAAGAAAA ATGCTGAATG AGCATGATTT TGAAGTCAGA GGAGATGTGG    5340
TCAATGGAAG AAACCACCAA GGTCCAAAGC GAGCAAGAGA ATCCAGGGAC AGAAAGATCT    5400
TCAGGGGGCT AGAAATCTGT TGCTATGGGC CCTTCACCAA CATGCCCACA GATCAACTGG    5460
```

| | | | | | |
|---|---|---|---|---|---|
| AATGGATGGT | ACAGCTGTGT | GGTGCTTCTG | TGGTGAAGGA | GCTTTCATCA | TTCACCCTTG | 5520 |
| GCACAGGTGT | CCACCCAATT | GTGGTTGTGC | AGCCAGATGC | CTGGACAGAG | GACAATGGCT | 5580 |
| TCCATGCAAT | TGGGCAGATG | TGTGAGGCAC | CTGTGGTGAC | CCGAGAGTGG | GTGTTGGACA | 5640 |
| GTGTAGCACT | CTACCAGTGC | CAGGAGCTGG | ACACCTACCT | GATACCCCAG | ATCCCCCACA | 5700 |
| GCCACTACTG | A | | | | | 5711 |

( 2 ) INFORMATION FOR SEQ ID NO:11:

( i ) SEQUENCE CHARACTERISTICS:
        ( A ) LENGTH: 5707 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:11:

| | | | | | |
|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAAGACGTCT | GTCTACATTG | 660 |
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAAGGTAG | 1140 |
| ATCTGAATGC | TGATCCCCTG | TGTGAGAGAA | AAGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |

```
AGAATGGTCA  AGTGATGAAT  ATTACTAATA  GTGGTCATGA  GAATAAAACA  AAAGGTGATT  1800
CTATTCAGAA  TGAGAAAAAT  CCTAACCCAA  TAGAATCACT  CGAAAAAGAA  TCTGCTTTCA  1860
AAACGAAAGC  TGAACCTATA  AGCAGCAGTA  TAAGCAATAT  GGAACTCGAA  TTAAATATCC  1920
ACAATTCAAA  AGCACCTAAA  AAGAATAGGC  TGAGGAGGAA  GTCTTCTACC  AGGCATATTC  1980
ATGCGCTTGA  ACTAGTAGTC  AGTAGAAATC  TAAGCCCACC  TAATTGTACT  GAATTGCAAA  2040
TTGATAGTTG  TTCTAGCAGT  GAAGAGATAA  AGAAAAAAAA  GTACAACCAA  ATGCCAGTCA  2100
GGCACAGCAG  AAACCTACAA  CTCATGGAAG  GTAAAGAACC  TGCAACTGGA  GCCAAGAAGA  2160
GTAACAAGCC  AAATGAACAG  ACAAGTAAAA  GACATGACAG  CGATACTTTC  CCAGAGCTGA  2220
AGTTAACAAA  TGCACCTGGT  TCTTTTACTA  AGTGTTCAAA  TACCAGTGAA  CTTAAAGAAT  2280
TTGTCAATCC  TAGCCTTCCA  AGAGAAGAAA  AAGAAGAGAA  ACTAGAAACA  GTTAAAGTGT  2340
CTAATAATGC  TGAAGACCCC  AAAGATCTCA  TGTTAAGTGG  AGAAAGGGTT  TTGCAAACTG  2400
AAAGATCTGT  AGAGAGTAGC  AGTATTTCAT  TGGTACCTGG  TACTGATTAT  GGCACTCAGG  2460
AAAGTATCTC  GTTACTGGAA  GTTAGCACTC  TAGGGAAGGC  AAAAACAGAA  CCAAATAAAT  2520
GTGTGAGTCA  GTGTGCAGCA  TTTGAAAACC  CCAAGGGACT  AATTCATGGT  TGTTCCAAAG  2580
ATAATAGAAA  TGACACAGAA  GGCTTTAAGT  ATCCATTGGG  ACATGAAGTT  AACCACAGTC  2640
GGGAAACAAG  CATAGAAATG  GAAGAAAGTG  AACTTGATGC  TCAGTATTTG  CAGAATACAT  2700
TCAAGGTTTC  AAAGCGCCAG  TCATTTGCTC  CGTTTTCAAA  TCCAGGAAAT  GCAGAAGAGG  2760
AATGTGCAAC  ATTCTCTGCC  CACTCTGGGT  CCTTAAAGAA  ACAAAGTCCA  AAAGTCACTT  2820
TTGAATGTGA  ACAAAAGGAA  GAAAATCAAG  GAAAGAATGA  GTCTAATATC  AAGCCTGTAC  2880
AGACAGTTAA  TATCACTGCA  GGCTTTCCTG  TGGTTGGTCA  GAAAGATAAG  CCAGTTGATA  2940
ATGCCAAATG  TAGTATCAAA  GGAGGCTCTA  GGTTTTGTCT  ATCATCTCAG  TTCAGAGGCA  3000
ACGAAACTGG  ACTCATTACT  CCAAATAAAC  ATGGACTTTT  ACAAAACCCA  TATCGTATAC  3060
CACCACTTTT  TCCCATCAAG  TCATTTGTTA  AAACTAAATG  TAAGAAAAAT  CTGCTAGAGG  3120
AAAACTTTGA  GGAACATTCA  ATGTCACCTG  AAAGAGAAAT  GGGAAATGAG  AACATTCCAA  3180
GTACAGTGAG  CACAATTAGC  CGTAATAACA  TTAGAGAAAA  TGTTTTTAAA  GAAGCCAGCT  3240
CAAGCAATAT  TAATGAAGTA  GGTTCCAGTA  CTAATGAAGT  GGGCTCCAGT  ATTAATGAAA  3300
TAGGTTCCAG  TGATGAAAAC  ATTCAAGCAG  AACTAGGTAG  AAACAGAGGG  CCAAAATTGA  3360
ATGCTATGCT  TAGATTAGGG  GTTTTGCAAC  CTGAGGTCTA  TAAACAAAGT  CTTCCTGGAA  3420
GTAATTGTAA  GCATCCTGAA  ATAAAAAAGC  AAGAATATGA  AGAAGTAGTT  CAGACTGTTA  3480
ATACAGATTT  CTCTCCATAT  CTGATTTCAG  ATAACTTAGA  ACAGCCTATG  GGAAGTAGTC  3540
ATGCATCTCA  GGTTTGTTCT  GAGACACCTG  ATGACCTGTT  AGATGATGGT  GAAATAAAGG  3600
AAGATACTAG  TTTTGCTGAA  AATGACATTA  AGGAAAGTTC  TGCTGTTTTT  AGCAAAAGCG  3660
TCCAGAAAGG  AGAGCTTAGC  AGGAGTCCTA  GCCCTTTCAC  CCATACACAT  TTGGCTCAGG  3720
GTTACCGAAG  AGGGGCCAAG  AAATTAGAGT  CCTCAGAAGA  GAACTTATCT  AGTGAGGATG  3780
AAGAGCTTCC  CTGCTTCCAA  CACTTGTTAT  TTGGTAAAGT  AAACAATATA  CCTTCTCAGT  3840
CTACTAGGCA  TAGCACCGTT  GCTACCGAGT  GTCTGTCTAA  GAACACAGAG  GAGAATTTAT  3900
TATCATTGAA  GAATAGCTTA  AATGACTGCA  GTAACCAGGT  AATATTGGCA  AAGGCATCTC  3960
AGGAACATCA  CCTTAGTGAG  GAAACAAAAT  GTTCTGCTAG  CTTGTTTTCT  TCACAGTGCA  4020
GTGAATTGGA  AGACTTGACT  GCAAATACAA  ACACCCAGGA  TCCTTTCTTG  ATTGGTTCTT  4080
CCAAACAAAT  GAGGCATCAG  TCTGAAAGCC  AGGGAGTTGG  TCTGAGTGAC  AAGGAATTGG  4140
```

-continued

| | | | | | |
|---|---|---|---|---|---|
| TTTCAGATGA | TGAAGAAAGA | GGAACGGGCT | TGGAAGAAAA | TAAGAAGAGC | AAAGCATGGA | 4200
| TTCAAACTTA | GGTGAAGCAG | CATCTGGGTG | TGAGAGTGAA | ACAAGCGTCT | CTGAAGACTG | 4260
| CTCAGGGCTA | TCCTCTCAGA | GTGACATTTT | AACCACTCAG | CAGAGGGATA | CCATGCAACA | 4320
| TAACCTGATA | AAGCTCCAGC | AGGAAATGGC | TGAACTAGAA | GCTGTGTTAG | AACAGCATGG | 4380
| GAGCCAGCCT | TCTAACAGCT | ACCCTTCCAT | CATAAGTGAC | TCTTCTGCCC | TTGAGGACCT | 4440
| GCGAAATCCA | GAACAAAGCA | CATCAGAAAA | AGCAGTATTA | ACTTCACAGA | AAAGTAGTGA | 4500
| ATACCCTATA | AGCCAGAATC | CAGAAGGCCT | TTCTGCTGAC | AAGTTTGAGG | TGTCTGCAGA | 4560
| TAGTTCTACC | AGTAAAAATA | AAGAACCAGG | AGTGGAAAGG | TCATCCCCTT | CTAAATGCCC | 4620
| ATCATTAGAT | GATAGGTGGT | ACATGCACAG | TTGCTCTGGG | AGTCTTCAGA | ATAGAAACTA | 4680
| CCCATCTCAA | GAGGAGCTCA | TTAAGGTTGT | TGATGTGGAG | GAGCAACAGC | TGGAAGAGTC | 4740
| TGGGCCACAC | GATTTGACGG | AAACATCTTA | CTTGCCAAGG | CAAGATCTAG | AGGGAACCCC | 4800
| TTACCTGGAA | TCTGGAATCA | GCCTCTTCTC | TGATGACCCT | GAATCTGATC | CTTCTGAAGA | 4860
| CAGAGCCCCA | GAGTCAGCTC | GTGTTGGCAA | CATACCATCT | TCAACCTCTG | CATTGAAAGT | 4920
| TCCCCAATTG | AAAGTTGCAG | AATCTGCCCA | GAGTCCAGCT | GCTGCTCATA | CTACTGATAC | 4980
| TGCTGGGTAT | AATGCAATGG | AAGAAAGTGT | GAGCAGGGAG | AAGCCAGAAT | TGACAGCTTC | 5040
| AACAGAAAGG | GTCAACAAAA | GAATGTCCAT | GGTGGTGTCT | GGCCTGACCC | CAGAAGAATT | 5100
| TATGCTCGTG | TACAAGTTTG | CCAGAAAACA | CCACATCACT | TTAACTAATC | TAATTACTGA | 5160
| AGAGACTACT | CATGTTGTTA | TGAAAACAGA | TGCTGAGTTT | GTGTGTGAAC | GGACACTGAA | 5220
| ATATTTTCTA | GGAATTGCGG | GAGGAAAATG | GGTAGTTAGC | TATTTCTGGG | TGACCCAGTC | 5280
| TATTAAAGAA | AGAAAAATGC | TGAATGAGCA | TGATTTTGAA | GTCAGAGGAG | ATGTGGTCAA | 5340
| TGGAAGAAAC | CACCAAGGTC | CAAAGCGAGC | AAGAGAATCC | CAGGACAGAA | AGATCTTCAG | 5400
| GGGGCTAGAA | ATCTGTTGCT | ATGGGCCCTT | CACCAACATG | CCCACAGATC | AACTGGAATG | 5460
| GATGGTACAG | CTGTGTGGTG | CTTCTGTGGT | GAAGGAGCTT | TCATCATTCA | CCCTTGGCAC | 5520
| AGGTGTCCAC | CCAATTGTGG | TTGTGCAGCC | AGATGCCTGG | ACAGAGGACA | ATGGCTTCCA | 5580
| TGCAATTGGG | CAGATGTGTG | AGGCACCTGT | GGTGACCCGA | GAGTGGGTGT | TGGACAGTGT | 5640
| AGCACTCTAC | CAGTGCCAGG | AGCTGGACAC | CTACCTGATA | CCCCAGATCC | CCACAGCCA | 5700
| CTACTGA | | | | | | 5707

( 2 ) INFORMATION FOR SEQ ID NO:12:

( i ) SEQUENCE CHARACTERISTICS:
   ( A ) LENGTH: 5712 base pairs
   ( B ) TYPE: nucleic acid
   ( C ) STRANDEDNESS: double
   ( D ) TOPOLOGY: linear ( i i ) MOLECULE TYPE: cDNA ( x i ) SEQUENCE DESCRIPTION: SEQ ID NO:12:

| | | | | | |
|---|---|---|---|---|---|
| AGCTCGCTGA | GACTTCCTGG | ACCCCGCACC | AGGCTGTGGG | GTTTCTCAGA | TAACTGGGCC | 60
| CCTGCGCTCA | GGAGGCCTTC | ACCCTCTGCT | CTGGGTAAAG | TTCATTGGAA | CAGAAAGAAA | 120
| TGGATTTATC | TGCTCTTCGC | GTTGAAGAAG | TACAAAATGT | CATTAATGCT | ATGCAGAAAA | 180
| TCTTAGAGTG | TCCCATCTGT | CTGGAGTTGA | TCAAGGAACC | TGTCTCCACA | AAGTGTGACC | 240
| ACATATTTTG | CAAATTTTGC | ATGCTGAAAC | TTCTCAACCA | GAAGAAGGG | CCTTCACAGT | 300
| GTCCTTTATG | TAAGAATGAT | ATAACCAAAA | GGAGCCTACA | AGAAAGTACG | AGATTTAGTC | 360

| | | | | | | |
|---|---|---|---|---|---|---|
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAAGACGTCT | GTCTACATTG | 660 |
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAAGGTAG | 1140 |
| ATCTGAATGC | TGATCCCCTG | TGTGAGAGAA | AAGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |
| ACAATTCAAA | AGCACCTAAA | AAGAATAGGC | TGAGGAGGAA | GTCTTCTACC | AGGCATATTC | 1980 |
| ATGCGCTTGA | ACTAGTAGTC | AGTAGAAATC | TAAGCCCACC | TAATTGTACT | GAATTGCAAA | 2040 |
| TTGATAGTTG | TTCTAGCAGT | GAAGAGATAA | AGAAAAAAAA | GTACAACCAA | ATGCCAGTCA | 2100 |
| GGCACAGCAG | AAACCTACAA | CTCATGGAAG | GTAAAGAACC | TGCAACTGGA | GCCAAGAAGA | 2160 |
| GTAACAAGCC | AAATGAACAG | ACAAGTAAAA | GACATGACAG | CGATACTTTC | CCAGAGCTGA | 2220 |
| AGTTAACAAA | TGCACCTGGT | TCTTTTACTA | AGTGTTCAAA | TACCAGTGAA | CTTAAAGAAT | 2280 |
| TTGTCAATCC | TAGCCTTCCA | AGAGAAGAAA | AAGAAGAGAA | ACTAGAAACA | GTTAAAGTGT | 2340 |
| CTAATAATGC | TGAAGACCCC | AAAGATCTCA | TGTTAAGTGG | AGAAAGGGTT | TTGCAAACTG | 2400 |
| AAAGATCTGT | AGAGAGTAGC | AGTATTTCAT | TGGTACCTGG | TACTGATTAT | GGCACTCAGG | 2460 |
| AAAGTATCTC | GTTACTGGAA | GTTAGCACTC | TAGGGAAGGC | AAAAACAGAA | CCAAATAAAT | 2520 |
| GTGTGAGTCA | GTGTGCAGCA | TTTGAAAACC | CCAAGGGACT | AATTCATGGT | TGTTCCAAAG | 2580 |
| ATAATAGAAA | TGACACAGAA | GGCTTTAAGT | ATCCATTGGG | ACATGAAGTT | AACCACAGTC | 2640 |
| GGGAAACAAG | CATAGAAATG | GAAGAAAGTG | AACTTGATGC | TCAGTATTTG | CAGAATACAT | 2700 |
| TCAAGGTTTC | AAAGCGCCAG | TCATTTGCTC | CGTTTTCAAA | TCCAGGAAAT | GCAGAAGAGG | 2760 |

```
AATGTGCAAC  ATTCTCTGCC  CACTCTGGGT  CCTTAAAGAA  ACAAAGTCCA  AAAGTCACTT   2820
TTGAATGTGA  ACAAAAGGAA  GAAAATCAAG  GAAAGAATGA  GTCTAATATC  AAGCCTGTAC   2880
AGACAGTTAA  TATCACTGCA  GGCTTTCCTG  TGGTTGGTCA  GAAAGATAAG  CCAGTTGATA   2940
ATGCCAAATG  TAGTATCAAA  GGAGGCTCTA  GGTTTTGTCT  ATCATCTCAG  TTCAGAGGCA   3000
ACGAAACTGG  ACTCATTACT  CCAAATAAAC  ATGGACTTTT  ACAAAACCCA  TATCGTATAC   3060
CACCACTTTT  TCCCATCAAG  TCATTTGTTA  AAACTAAATG  TAAGAAAAAT  CTGCTAGAGG   3120
AAAACTTTGA  GGAACATTCA  ATGTCACCTG  AAAGAGAAAT  GGGAAATGAG  AACATTCCAA   3180
GTACAGTGAG  CACAATTAGC  CGTAATAACA  TTAGAGAAAA  TGTTTTTAAA  GAAGCCAGCT   3240
CAAGCAATAT  TAATGAAGTA  GGTTCCAGTA  CTAATGAAGT  GGGCTCCAGT  ATTAATGAAA   3300
TAGGTTCCAG  TGATGAAAAC  ATTCAAGCAG  AACTAGGTAG  AAACAGAGGG  CCAAAATTGA   3360
ATGCTATGCT  TAGATTAGGG  GTTTTGCAAC  CTGAGGTCTA  TAAACAAAGT  CTTCCTGGAA   3420
GTAATTGTAA  GCATCCTGAA  ATAAAAAGC   AAGAATATGA  AGAAGTAGTT  CAGACTGTTA   3480
ATACAGATTT  CTCTCCATAT  CTGATTTCAG  ATAACTTAGA  ACAGCCTATG  GAAGTAGTC    3540
ATGCATCTCA  GGTTTGTTCT  GAGACACCTG  ATGACCTGTT  AGATGATGGT  GAAATAAAGG   3600
AAGATACTAG  TTTTGCTGAA  AATGACATTA  AGGAAAGTTC  TGCTGTTTTT  AGCAAAAGCG   3660
TCCAGAAAGG  AGAGCTTAGC  AGGAGTCCTA  GCCCTTTCAC  CCATACACAT  TTGGCTCAGG   3720
GTTACCGAAG  AGGGGCCAAG  AAATTAGAGT  CCTCAGAAGA  GAACTTATCT  AGTGAGGATG   3780
AAGAGCTTCC  CTGCTTCCAA  CACTTGTTAT  TTGGTAAAGT  AAACAATATA  CCTTCTCAGT   3840
CTACTAGGCA  TAGCACCGTT  GCTACCGAGT  GTCTGTCTAA  GAACACAGAG  GAGAATTTAT   3900
TATCATTGAA  GAATAGCTTA  AATGACTGCA  GTAACCAGGT  AATATTGGCA  AAGGCATCTC   3960
AGGAACATCA  CCTTAGTGAG  GAAACAAAAT  GTTCTGCTAG  CTTGTTTTCT  TCACAGTGCA   4020
GTGAATTGGA  AGACTTGACT  GCAAATACAA  ACACCCAGGA  TCCTTTCTTG  ATTGGTTCTT   4080
CCAAACAAAT  GAGGCATCAG  TCTGAAAGCC  AGGGAGTTGG  TCTGAGTGAC  AAGGAATTGG   4140
TTTCAGATGA  TGAAGAAAGA  GGAACGGGCT  TGGAAGAAAA  TAATCAAGAA  GAGCAAAGCA   4200
TGGATTCAAA  CTTAGGTGAA  GCAGCATCTG  GGTGTGAGAG  TGAAACAAGC  GTCTCTGAAG   4260
ACTGCTCAGG  GCTATCCTCT  CAGAGTGACA  TTTTAACCAC  TCAGCAGAGG  GATACCATGC   4320
AACATAACCT  GATAAAGCTC  CAGCAGGAAA  TGGCTGAACT  AGAAGCTGTG  TTAGAACAGC   4380
ATGGGAGCCA  GCCTTCTAAC  AGCTACCCTT  CCATCATAAG  TGACTCTTCT  GCCCTTGAGG   4440
ACCTGCGAAA  TCCAGAACAA  AGCACATCAG  AAAAAGCAGT  ATTAACTTCA  CAGAAAAGTA   4500
GTGAATACCC  TATAAGCCAG  AATCCAGAAG  GCCTTTCTGC  TGACAAGTTT  GAGGTGTCTG   4560
CAGATAGTTC  TACCAGTAAA  AATAAAGAAC  CAGGAGTGGA  AAGGTCATCC  CCTTCTAAAT   4620
GCCCATCATT  AGATGATAGG  TGGTACATGC  ACAGTTGCTC  TGGGAGTCTT  CAGAATAGAA   4680
ACTACCCATC  TCAAGAGGAG  CTCATTAAGG  TTGTTGATGT  GGAGGAGCAA  CAGCTGGAAG   4740
AGTCTGGGCC  ACACGATTTG  ACGGAAACAT  CTTACTTGCC  AAGGCAAGAT  CTAGAGGGAA   4800
CCCCTTACCT  GGAATCTGGA  ATCAGCCTCT  TCTCTGATGA  CCCTGAATCT  GATCCTTCTG   4860
AAGACAGAGC  CCCAGAGTCA  GCTCGTGTTG  GCAACATACC  ATCTTCAACC  TCTGCATTGA   4920
AAGTTCCCCA  ATTGAAAGTT  GCAGAATCTG  CCCAGAGTCC  AGCTGCTGCT  CATACTACTG   4980
ATACTGCTGG  GTATAATGCA  ATGGAAGAAA  GTGTGAGCAG  GGAGAAGCCA  GAATTGACAG   5040
CTTCAACAGA  AAGGGTCAAC  AAAAGAATGT  CCATGGTGGT  GTCTGGCCTG  ACCCCAGAAG   5100
AATTTATGCT  CGTGTACAAG  TTTGCCAGAA  AACACCACAT  CACTTTAACT  AATCTAATTA   5160
```

-continued

```
CTGAAGAGAC  TACTCATGTT  GTTATGAAAA  CAGATGCTGA  GTTTGTGTGT  GAACGGACAC    5220

TGAAATATTT  TCTAGGAATT  GCGGGAGGAA  AATGGGTAGT  TAGCTATTTC  TGGGTGACCC    5280

AGTCTATTAA  AGAAAGAAAA  ATGCTGAATG  AGCATGATTT  TGAAGTCAGA  GGAGATGTGG    5340

TCAATGGAAG  AAACCACCAA  GGTCCAAAGC  GAGCAAGAGA  ATCCCAGGAC  AGAAAGATCT    5400

TCAGGGGGCT  AGAAATCTGT  TGCTATGGGC  CCTTCACCAA  CATGCCCACA  GATCAACTGG    5460

AATGGATGGT  ACAGCTGTGT  GGTGCTTCTG  TGGTGAAGGA  GCTTTCATCA  TTCACCCTTG    5520

GCACAGGTGT  CCACCCAATT  GTGGTTGTGC  AGCCAGATGC  CTGGACAGAG  GACAATGGCT    5580

TCCATGCAAT  TGGGCAGATG  TGTGAGGCAC  CTGTGGTGAC  CCGAGAGTGG  GTGTTGGACA    5640

GTGTAGCACT  CTACCAGTGC  CAGGAGCTGG  ACACCTAACC  TGATACCCCA  GATCCCCCAC    5700

AGCCACTACT  GA                                                            5712
```

( 2 ) INFORMATION FOR SEQ ID NO:13:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Met  Asp  Leu  Ser  Ala  Leu  Arg  Val  Glu  Glu  Val  Gln  Asn  Val  Ile  Asn
 1              5                        10                       15

Ala  Met  Gln  Lys  Ile  Leu  Glu  Cys  Pro  Ile
             20                       25
```

( 2 ) INFORMATION FOR SEQ ID NO:14:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Met  Asp  Leu  Ser  Ala  Leu  Arg  Val  Glu  Glu  Val  Gln  Asn  Val  Ile  Asn
 1              5                        10                       15

Ala  Met  Gln  Lys  Ile  Leu  Glu  Cys  Pro  Ile  Cys  Leu  Glu  Leu  Ile  Lys
             20                       25                       30

Glu  Pro  Val  Ser  Thr  Val
             35
```

( 2 ) INFORMATION FOR SEQ ID NO:15:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Met  Asp  Leu  Ser  Ala  Leu  Arg  Val  Glu  Glu  Val  Gln  Asn  Val  Ile  Asn
 1              5                        10                       15

Ala  Met  Gln  Lys  Ile  Leu  Glu  Cys  Pro  Ile  Cys  Leu  Glu  Leu  Ile  Lys
             20                       25                       30
```

```
Glu  Pro  Val  Ser  Thr  Lys  Cys  Asp  His  Ile  Phe  Cys  Lys  Phe  Cys  Met
          35                  40                      45

Leu  Lys  Leu  Leu  Asn  Gln  Lys  Lys  Gly  Pro  Ser  Gln  Cys  Pro  Leu
          50                  55                      60
```

( 2 ) INFORMATION FOR SEQ ID NO:16:

( i ) SEQUENCE CHARACTERISTICS:
        ( A ) LENGTH: 1863 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

```
Met  Asp  Leu  Ser  Ala  Leu  Arg  Val  Glu  Val  Gln  Asn  Val  Ile  Asn
1              5                   10                      15

Ala  Met  Gln  Lys  Ile  Leu  Glu  Cys  Pro  Ile  Cys  Leu  Glu  Leu  Ile  Lys
          20                  25                      30

Glu  Pro  Val  Ser  Thr  Lys  Cys  Asp  His  Ile  Phe  Cys  Lys  Phe  Cys  Met
          35                  40                      45

Leu  Lys  Leu  Leu  Asn  Gln  Lys  Lys  Gly  Pro  Ser  Gln  Gly  Pro  Leu  Cys
          50                  55                      60

Lys  Asn  Asp  Ile  Thr  Lys  Arg  Ser  Leu  Gln  Glu  Ser  Thr  Arg  Phe  Ser
65                  70                      75                          80

Gln  Leu  Val  Glu  Glu  Leu  Leu  Lys  Ile  Ile  Cys  Ala  Phe  Gln  Leu  Asp
               85                  90                      95

Thr  Gly  Leu  Glu  Tyr  Ala  Asn  Ser  Tyr  Asn  Phe  Ala  Lys  Lys  Glu  Asn
               100                 105                     110

Asn  Ser  Pro  Glu  His  Leu  Lys  Asp  Glu  Val  Ser  Ile  Ile  Gln  Ser  Met
               115                 120                     125

Gly  Tyr  Arg  Asn  Arg  Ala  Lys  Arg  Leu  Leu  Gln  Ser  Glu  Pro  Glu  Asn
               130                 135                     140

Pro  Ser  Leu  Gln  Glu  Thr  Ser  Leu  Ser  Val  Gln  Leu  Ser  Asn  Leu  Gly
145                 150                     155                         160

Thr  Val  Arg  Thr  Leu  Arg  Thr  Lys  Gln  Arg  Ile  Gln  Pro  Gln  Lys  Thr
               165                 170                     175

Ser  Val  Tyr  Ile  Glu  Leu  Gly  Ser  Asp  Ser  Ser  Glu  Asp  Thr  Val  Asn
               180                 185                     190

Lys  Ala  Thr  Tyr  Cys  Ser  Val  Gly  Asp  Gln  Glu  Leu  Leu  Gln  Ile  Thr
               195                 200                     205

Pro  Gln  Gly  Thr  Arg  Asp  Glu  Ile  Ser  Leu  Asp  Ser  Ala  Lys  Lys  Ala
210                 215                     220

Ala  Cys  Glu  Phe  Ser  Glu  Thr  Asp  Val  Thr  Asn  Thr  Glu  His  His  Gln
225                 230                     235                         240

Pro  Ser  Asn  Asn  Asp  Leu  Asn  Thr  Thr  Glu  Lys  Arg  Ala  Ala  Glu  Arg
               245                 250                     255

His  Pro  Glu  Lys  Tyr  Gln  Gly  Ser  Ser  Val  Ser  Asn  Leu  His  Val  Glu
               260                 265                     270

Pro  Cys  Gly  Thr  Asn  Thr  His  Ala  Ser  Ser  Leu  Gln  His  Glu  Asn  Ser
               275                 280                     285

Ser  Leu  Leu  Leu  Thr  Lys  Asp  Arg  Met  Asn  Val  Glu  Lys  Ala  Glu  Phe
               290                 295                     300

Cys  Asn  Lys  Ser  Lys  Gln  Pro  Gly  Leu  Ala  Arg  Ser  Gln  His  Asn  Arg
305                 310                     315                         320

Trp  Ala  Gly  Ser  Lys  Glu  Thr  Cys  Asn  Asp  Arg  Arg  Thr  Pro  Ser  Thr
```

```
                              325                      330                      335
    Glu  Lys  Lys  Val  Asp  Leu  Asn  Ala  Asp  Pro  Leu  Cys  Glu  Arg  Lys  Glu
                   340                      345                      350

Trp  Asn  Lys  Gln  Lys  Leu  Pro  Cys  Ser  Glu  Asn  Pro  Arg  Asp  Thr  Glu
                   355                      360                      365

Asp  Val  Pro  Trp  Ile  Thr  Leu  Asn  Ser  Ser  Ile  Gln  Lys  Val  Asn  Glu
                   370                      375                      380

Trp  Phe  Ser  Arg  Ser  Asp  Glu  Leu  Leu  Gly  Ser  Asp  Asp  Ser  His  Asp
    385                      390                      395                      400

Gly  Glu  Ser  Glu  Ser  Asn  Ala  Lys  Val  Ala  Asp  Val  Leu  Asp  Val  Leu
                   405                      410                      415

Asn  Glu  Val  Asp  Glu  Tyr  Ser  Gly  Ser  Ser  Glu  Lys  Ile  Asp  Leu  Leu
                   420                      425                      430

Ala  Ser  Asp  Pro  His  Glu  Ala  Leu  Ile  Cys  Lys  Ser  Glu  Arg  Val  His
                   435                      440                      445

Ser  Lys  Ser  Val  Glu  Ser  Asn  Ile  Glu  Asp  Lys  Ile  Phe  Gly  Lys  Thr
         450                      455                      460

Tyr  Arg  Lys  Lys  Ala  Ser  Leu  Pro  Asn  Leu  Ser  His  Val  Thr  Glu  Asn
    465                      470                      475                      480

Leu  Ile  Ile  Gly  Ala  Phe  Val  Thr  Glu  Pro  Gln  Ile  Ile  Gln  Glu  Arg
                        485                      490                      495

Pro  Leu  Thr  Asn  Lys  Leu  Lys  Arg  Lys  Arg  Arg  Pro  Thr  Ser  Gly  Leu
                   500                      505                      510

His  Pro  Glu  Asp  Phe  Ile  Lys  Lys  Ala  Asp  Leu  Ala  Val  Gln  Lys  Thr
                   515                      520                      525

Pro  Glu  Met  Ile  Asn  Gln  Gly  Thr  Asn  Gln  Thr  Glu  Gln  Asn  Gly  Gln
         530                      535                      540

Val  Met  Asn  Ile  Thr  Asn  Ser  Gly  His  Glu  Asn  Lys  Thr  Lys  Gly  Asp
    545                      550                      555                      560

Ser  Ile  Gln  Asn  Glu  Lys  Asn  Pro  Asn  Pro  Ile  Glu  Ser  Leu  Glu  Lys
                        565                      570                      575

Glu  Ser  Ala  Phe  Lys  Thr  Lys  Ala  Glu  Pro  Ile  Ser  Ser  Ser  Ile  Ser
                   580                      585                      590

Asn  Met  Glu  Leu  Glu  Leu  Asn  Ile  His  Asn  Ser  Lys  Ala  Pro  Lys  Lys
         595                      600                      605

Asn  Arg  Leu  Arg  Arg  Lys  Ser  Ser  Thr  Arg  His  Ile  His  Ala  Leu  Glu
    610                      615                      620

Leu  Val  Val  Ser  Arg  Asn  Leu  Ser  Pro  Pro  Asn  Cys  Thr  Glu  Leu  Gln
    625                      630                      635                      640

Ile  Asp  Ser  Cys  Ser  Ser  Ser  Glu  Glu  Ile  Lys  Lys  Lys  Lys  Tyr  Asn
                        645                      650                      655

Gln  Met  Pro  Val  Arg  His  Ser  Arg  Asn  Leu  Gln  Leu  Met  Glu  Gly  Lys
                   660                      665                      670

Glu  Pro  Ala  Thr  Gly  Ala  Lys  Lys  Ser  Asn  Lys  Pro  Asn  Glu  Gln  Thr
                   675                      680                      685

Ser  Lys  Arg  His  Asp  Ser  Asp  Thr  Phe  Pro  Glu  Leu  Lys  Leu  Thr  Asn
         690                      695                      700

Ala  Pro  Gly  Ser  Phe  Thr  Lys  Cys  Ser  Asn  Thr  Ser  Glu  Leu  Lys  Glu
    705                      710                      715                      720

Phe  Val  Asn  Pro  Ser  Leu  Pro  Arg  Glu  Glu  Lys  Glu  Glu  Lys  Leu  Glu
                        725                      730                      735

Thr  Val  Lys  Val  Ser  Asn  Asn  Ala  Glu  Asp  Pro  Lys  Asp  Leu  Met  Leu
                   740                      745                      750
```

-continued

```
Ser  Gly  Glu  Arg  Val  Leu  Gln  Thr  Glu  Arg  Ser  Val  Glu  Ser  Ser  Ser
          755                      760                      765

Ile  Ser  Leu  Val  Pro  Gly  Thr  Asp  Tyr  Gly  Thr  Gln  Glu  Ser  Ile  Ser
770                           775                      780

Leu  Leu  Glu  Val  Ser  Thr  Leu  Gly  Lys  Ala  Lys  Thr  Glu  Pro  Asn  Lys
785                      790                      795                           800

Cys  Val  Ser  Gln  Cys  Ala  Ala  Phe  Glu  Asn  Pro  Lys  Gly  Leu  Ile  His
                    805                      810                           815

Gly  Cys  Ser  Lys  Asp  Asn  Arg  Asn  Asp  Thr  Glu  Gly  Phe  Lys  Tyr  Pro
               820                      825                           830

Leu  Gly  His  Glu  Val  Asn  His  Ser  Arg  Glu  Thr  Ser  Ile  Glu  Met  Glu
               835                      840                      845

Glu  Ser  Glu  Leu  Asp  Ala  Gln  Tyr  Leu  Gln  Asn  Thr  Phe  Lys  Val  Ser
850                                855                      860

Lys  Arg  Gln  Ser  Phe  Ala  Pro  Phe  Ser  Asn  Pro  Gly  Asn  Ala  Glu  Glu
865                           870                      875                      880

Glu  Cys  Ala  Thr  Phe  Ser  Ala  His  Ser  Gly  Ser  Leu  Lys  Lys  Gln  Ser
                         885                      890                      895

Pro  Lys  Val  Thr  Phe  Glu  Cys  Glu  Gln  Lys  Glu  Glu  Asn  Gln  Gly  Lys
                    900                      905                      910

Asn  Glu  Ser  Asn  Ile  Lys  Pro  Val  Gln  Thr  Val  Asn  Ile  Thr  Ala  Gly
               915                      920                      925

Phe  Pro  Val  Val  Gly  Gln  Lys  Asp  Lys  Pro  Val  Asp  Asn  Ala  Lys  Cys
          930                      935                      940

Ser  Ile  Lys  Gly  Gly  Ser  Arg  Phe  Cys  Leu  Ser  Ser  Gln  Phe  Arg  Gly
945                           950                      955                      960

Asn  Glu  Thr  Gly  Leu  Ile  Thr  Pro  Asn  Lys  His  Gly  Leu  Leu  Gln  Asn
                    965                      970                           975

Pro  Tyr  Arg  Ile  Pro  Pro  Leu  Phe  Pro  Ile  Lys  Ser  Phe  Val  Lys  Thr
               980                      985                      990

Lys  Cys  Lys  Lys  Asn  Leu  Leu  Glu  Glu  Asn  Phe  Glu  Glu  His  Ser  Met
          995                      1000                     1005

Ser  Pro  Glu  Arg  Glu  Met  Gly  Asn  Glu  Asn  Ile  Pro  Ser  Thr  Val  Ser
     1010                     1015                     1020

Thr  Ile  Ser  Arg  Asn  Asn  Ile  Arg  Glu  Asn  Val  Phe  Lys  Glu  Ala  Ser
1025                     1030                     1035                         1040

Ser  Ser  Asn  Ile  Asn  Glu  Val  Gly  Ser  Ser  Thr  Asn  Glu  Val  Gly  Ser
               1045                     1050                          1055

Ser  Ile  Asn  Glu  Ile  Gly  Ser  Ser  Asp  Glu  Asn  Ile  Gln  Ala  Glu  Leu
               1060                     1065                          1070

Gly  Arg  Asn  Arg  Gly  Pro  Lys  Leu  Asn  Ala  Met  Leu  Arg  Leu  Gly  Val
          1075                     1080                     1085

Leu  Gln  Pro  Glu  Val  Tyr  Lys  Gln  Ser  Leu  Pro  Gly  Ser  Asn  Cys  Lys
     1090                     1095                     1100

His  Pro  Glu  Ile  Lys  Lys  Gln  Glu  Tyr  Glu  Glu  Val  Val  Gln  Thr  Val
1105                     1110                     1115                         1120

Asn  Thr  Asp  Phe  Ser  Pro  Tyr  Leu  Ile  Ser  Asp  Asn  Leu  Glu  Gln  Pro
               1125                     1130                          1135

Met  Gly  Ser  Ser  His  Ala  Ser  Gln  Val  Cys  Ser  Glu  Thr  Pro  Asp  Asp
               1140                     1145                          1150

Leu  Leu  Asp  Asp  Gly  Glu  Ile  Lys  Glu  Asp  Thr  Ser  Phe  Ala  Glu  Asn
               1155                     1160                          1165

Asp  Ile  Lys  Glu  Ser  Ser  Ala  Val  Phe  Ser  Lys  Ser  Val  Gln  Lys  Gly
     1170                     1175                     1180
```

Glu Leu Ser Arg Ser Pro Ser Pro Phe Thr His Thr His Leu Ala Gln
1185                1190                1195                1200

Gly Tyr Arg Arg Gly Ala Lys Lys Leu Glu Ser Ser Glu Glu Asn Leu
            1205                1210                1215

Ser Ser Glu Asp Glu Glu Leu Pro Cys Phe Gln His Leu Leu Phe Gly
            1220                1225                1230

Lys Val Asn Asn Ile Pro Ser Gln Ser Thr Arg His Ser Thr Val Ala
            1235                1240                1245

Thr Glu Cys Leu Ser Lys Asn Thr Glu Glu Asn Leu Leu Ser Leu Lys
            1250                1255                1260

Asn Ser Leu Asn Asp Cys Ser Asn Gln Val Ile Leu Ala Lys Ala Ser
1265                1270                1275                1280

Gln Glu His His Leu Ser Glu Glu Thr Lys Cys Ser Ala Ser Leu Phe
                1285                1290                1295

Ser Ser Gln Cys Ser Glu Leu Glu Asp Leu Thr Ala Asn Thr Asn Thr
            1300                1305                1310

Gln Asp Pro Phe Leu Ile Gly Ser Ser Lys Gln Met Arg His Gln Ser
            1315                1320                1325

Glu Ser Gln Gly Val Gly Leu Ser Asp Lys Glu Leu Val Ser Asp Asp
1330                1335                1340

Glu Glu Arg Gly Thr Gly Leu Glu Glu Asn Asn Gln Glu Glu Gln Ser
1345                1350                1355                1360

Met Asp Ser Asn Leu Gly Glu Ala Ala Ser Gly Cys Glu Ser Glu Thr
            1365                1370                1375

Ser Val Ser Glu Asp Cys Ser Gly Leu Ser Ser Gln Ser Asp Ile Leu
            1380                1385                1390

Thr Thr Gln Gln Arg Asp Thr Met Gln His Asn Leu Ile Lys Leu Gln
            1395                1400                1405

Gln Glu Met Ala Glu Leu Glu Ala Val Leu Glu Gln His Gly Ser Gln
            1410                1415                1420

Pro Ser Asn Ser Tyr Pro Ser Ile Ile Ser Asp Ser Ser Ala Leu Glu
1425                1430                1435                1440

Asp Leu Arg Asn Pro Glu Gln Ser Thr Ser Glu Lys Ala Val Leu Thr
            1445                1450                1455

Ser Gln Lys Ser Ser Glu Tyr Pro Ile Ser Gln Asn Pro Glu Gly Leu
            1460                1465                1470

Ser Ala Asp Lys Phe Glu Val Ser Ala Asp Ser Ser Thr Ser Lys Asn
            1475                1480                1485

Lys Glu Pro Gly Val Glu Arg Ser Ser Pro Ser Lys Cys Pro Ser Leu
            1490                1495                1500

Asp Asp Arg Trp Tyr Met His Ser Cys Ser Gly Ser Leu Gln Asn Arg
1505                1510                1515                1520

Asn Tyr Pro Ser Gln Glu Glu Leu Ile Lys Val Val Asp Val Glu Glu
            1525                1530                1535

Gln Gln Leu Glu Glu Ser Gly Pro His Asp Leu Thr Glu Thr Ser Tyr
            1540                1545                1550

Leu Pro Arg Gln Asp Leu Glu Gly Thr Pro Tyr Leu Glu Ser Gly Ile
            1555                1560                1565

Ser Leu Phe Ser Asp Asp Pro Glu Ser Asp Pro Ser Glu Asp Arg Ala
            1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Ser Pro Ala Ala 1605                         1610                              1615

Ala    His   Thr    Thr    Asp    Thr    Ala    Gly    Tyr    Asn    Ala    Met    Glu    Ser    Val
                             1620                        1625                       1630

Ser    Arg   Glu    Lys    Pro    Glu    Leu    Thr    Ala    Ser    Thr    Glu    Arg    Val    Asn    Lys
                      1635                        1640                              1645

Arg    Met   Ser    Met    Val    Val    Ser    Gly    Leu    Thr    Pro    Glu    Glu    Phe    Met    Leu
               1650                               1655                       1660

Val    Tyr   Lys    Phe    Ala    Arg    Lys    His    His    Ile    Thr    Leu    Thr    Asn    Leu    Ile
        1665                               1670                        1675                                     1680

Thr    Glu   Glu    Thr    Thr    His    Val    Val    Met    Lys    Thr    Asp    Ala    Glu    Phe    Val
                                    1685                        1690                              1695

Cys    Glu   Arg    Thr    Leu    Lys    Tyr    Phe    Leu    Gly    Ile    Ala    Gly    Gly    Lys    Trp
                            1700                               1705                         1710

Val    Val   Ser    Tyr    Phe    Trp    Val    Thr    Gln    Ser    Ile    Lys    Glu    Arg    Lys    Met
                             1715                               1720                       1725

Leu    Asn   Glu    His    Asp    Phe    Glu    Val    Arg    Gly    Asp    Val    Val    Asn    Gly    Arg
                     1730                               1735                         1740

Asn    His   Gln    Gly    Pro    Lys    Arg    Ala    Arg    Glu    Ser    Gln    Asp    Arg    Lys    Ile
        1745                               1750                        1755                                    1760

Phe    Arg   Gly    Leu    Glu    Ile    Cys    Cys    Tyr    Gly    Pro    Phe    Thr    Asn    Met    Pro
                                    1765                        1770                              1775

Thr    Asp   Gln    Leu    Glu    Trp    Met    Val    Gln    Leu    Cys    Gly    Ala    Ser    Val    Val
                            1780                               1785                        1790

Lys    Glu   Leu    Ser    Ser    Phe    Thr    Leu    Gly    Thr    Gly    Val    His    Pro    Ile    Val
                      1795                               1800                        1805

Val    Val   Gln    Pro    Asp    Ala    Trp    Thr    Glu    Asp    Asn    Gly    Phe    His    Ala    Ile
               1810                               1815                        1820

Gly    Gln   Met    Cys    Glu    Ala    Pro    Val    Val    Thr    Arg    Glu    Trp    Val    Leu    Asp
        1825                        1830                              1835                                      1840

Ser    Val   Ala    Leu    Tyr    Gln    Cys    Gln    Glu    Leu    Asp    Thr    Tyr    Leu    Ile    Pro
                                    1845                        1850                              1855

Gln    Ile   Pro    His    Ser    His    Tyr
                             1860

( 2 ) INFORMATION FOR SEQ ID NO:17:

( i ) SEQUENCE CHARACTERISTICS:
              ( A ) LENGTH: 80 amino acids
              ( B ) TYPE: amino acid
              ( C ) STRANDEDNESS: single
              ( D ) TOPOLOGY: linear ( i i ) MOLECULE TYPE: protein ( x i ) SEQUENCE DESCRIPTION: SEQ ID NO:17:

Met    Asp   Leu    Ser    Ala    Leu    Arg    Val    Glu    Glu    Val    Gln    Asn    Val    Ile    Asn
        1                          5                              10                                 15

Ala    Met   Gln    Lys    Ile    Leu    Glu    Cys    Pro    Ile    Cys    Leu    Glu    Leu    Ile    Lys
                             20                               25                           30

Glu    Pro   Val    Ser    Thr    Lys    Cys    Asp    His    Ile    Phe    Cys    Lys    Phe    Cys    Met
                             35                               40                                  45

Leu    Lys   Leu    Leu    Asn    Gln    Lys    Lys    Gly    Pro    Ser    Gln    Cys    Pro    Leu    Cys
                      50                               55                           60

Lys    Asn   Asp    Ile    Thr    Lys    Ser    Val    Leu    Lys    Arg    Leu    Ile    Ile    Thr    Cys
        65                                  70                              75                                  80

( 2 ) INFORMATION FOR SEQ ID NO:18:

(i) SEQUENCE CHARACTERISTICS:
  (A) LENGTH: 312 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:18:

| Met | Asp | Leu | Ser | Ala | Leu | Arg | Val | Glu | Glu | Val | Gln | Asn | Val | Ile | Asn |
|---|---|---|---|---|---|---|---|---|---|---|---|---|---|---|---|
| 1 | | | | 5 | | | | | 10 | | | | | 15 | |
| Ala | Met | Gln | Lys | Ile | Leu | Glu | Cys | Pro | Ile | Cys | Leu | Glu | Leu | Ile | Lys |
| | | | 20 | | | | 25 | | | | | | 30 | | |
| Glu | Pro | Val | Ser | Thr | Lys | Cys | Asp | His | Ile | Phe | Cys | Lys | Phe | Cys | Met |
| | | | 35 | | | | 40 | | | | | 45 | | | |
| Leu | Lys | Leu | Leu | Asn | Gln | Lys | Lys | Gly | Pro | Ser | Gln | Cys | Pro | Leu | Cys |
| | | | 50 | | | | 55 | | | | | 60 | | | |
| Lys | Asn | Asp | Ile | Thr | Lys | Arg | Ser | Leu | Gln | Glu | Ser | Thr | Arg | Phe | Ser |
| 65 | | | | | 70 | | | | | 75 | | | | | 80 |
| Gln | Leu | Val | Glu | Glu | Leu | Leu | Lys | Ile | Ile | Cys | Ala | Phe | Gln | Leu | Asp |
| | | | | 85 | | | | | 90 | | | | | 95 | |
| Thr | Gly | Leu | Glu | Tyr | Ala | Asn | Ser | Tyr | Asn | Phe | Ala | Lys | Lys | Glu | Asn |
| | | | | 100 | | | | | 105 | | | | | 110 | |
| Asn | Ser | Pro | Glu | His | Leu | Lys | Asp | Glu | Val | Ser | Ile | Ile | Gln | Ser | Met |
| | | | 115 | | | | 120 | | | | | 125 | | | |
| Gly | Tyr | Arg | Asn | Arg | Ala | Lys | Arg | Leu | Leu | Gln | Ser | Glu | Pro | Glu | Asn |
| | | | 130 | | | | 135 | | | | | 140 | | | |
| Pro | Ser | Leu | Gln | Glu | Thr | Ser | Leu | Ser | Val | Gln | Leu | Ser | Asn | Leu | Gly |
| 145 | | | | | 150 | | | | | 155 | | | | | 160 |
| Thr | Val | Arg | Thr | Leu | Arg | Thr | Lys | Gln | Arg | Ile | Gln | Pro | Gln | Lys | Thr |
| | | | | 165 | | | | | 170 | | | | | 175 | |
| Ser | Val | Tyr | Ile | Glu | Leu | Gly | Ser | Asp | Ser | Ser | Glu | Asp | Thr | Val | Asn |
| | | | | 180 | | | | | 185 | | | | | 190 | |
| Lys | Ala | Thr | Tyr | Cys | Ser | Val | Gly | Asp | Gln | Glu | Leu | Leu | Gln | Ile | Thr |
| | | | 195 | | | | 200 | | | | | 205 | | | |
| Pro | Gln | Gly | Thr | Arg | Asp | Glu | Ile | Ser | Leu | Asp | Ser | Ala | Lys | Lys | Ala |
| | | | 210 | | | | 215 | | | | | 220 | | | |
| Ala | Cys | Glu | Phe | Ser | Glu | Thr | Asp | Val | Thr | Asn | Thr | Glu | His | His | Gln |
| 225 | | | | | 230 | | | | | 235 | | | | | 240 |
| Pro | Ser | Asn | Asn | Asp | Leu | Asn | Thr | Thr | Glu | Lys | Arg | Ala | Ala | Glu | Arg |
| | | | | 245 | | | | | 250 | | | | | 255 | |
| His | Pro | Glu | Lys | Tyr | Gln | Gly | Ser | Ser | Val | Ser | Asn | Leu | His | Val | Glu |
| | | | | 260 | | | | | 265 | | | | | 270 | |
| Pro | Cys | Gly | Thr | Asn | Thr | His | Ala | Ser | Ser | Leu | Gln | His | Glu | Asn | Ser |
| | | | 275 | | | | 280 | | | | | 285 | | | |
| Ser | Leu | Leu | Leu | Thr | Lys | Asp | Arg | Met | Asn | Val | Glu | Lys | Ala | Glu | Phe |
| | 290 | | | | | 295 | | | | | 300 | | | | |
| Cys | Asn | Lys | Ser | Lys | Arg | Leu | Ala | | | | | | | | |
| 305 | | | | | 310 | | | | | | | | | | |

(2) INFORMATION FOR SEQ ID NO:19:

(i) SEQUENCE CHARACTERISTICS:
  (A) LENGTH: 765 amino acids
  (B) TYPE: amino acid
  (C) STRANDEDNESS: single
  (D) TOPOLOGY: linear ( i i ) MOLECULE TYPE: protein ( x i ) SEQUENCE DESCRIPTION: SEQ ID NO:19:

```
Met Asp Leu Ser Ala Leu Arg Val Glu Glu Val Gln Asn Val Ile Asn
 1               5                  10                  15

Ala Met Gln Lys Ile Leu Glu Cys Pro Ile Cys Leu Glu Leu Ile Lys
             20                  25                  30

Glu Pro Val Ser Thr Lys Cys Asp His Ile Phe Cys Lys Phe Cys Met
             35                  40                  45

Leu Lys Leu Leu Asn Gln Lys Gly Pro Ser Gln Cys Pro Leu Cys
     50                  55                  60

Lys Asn Asp Ile Thr Lys Arg Ser Leu Gln Glu Ser Thr Arg Phe Ser
 65              70                  75                  80

Gln Leu Val Glu Glu Leu Leu Lys Ile Ile Cys Ala Phe Gln Leu Asp
                 85                  90                  95

Thr Gly Leu Glu Tyr Ala Asn Ser Tyr Asn Phe Ala Lys Lys Glu Asn
             100                 105                 110

Asn Ser Pro Glu His Leu Lys Asp Glu Val Ser Ile Ile Gln Ser Met
         115                 120                 125

Gly Tyr Arg Asn Arg Ala Lys Arg Leu Leu Gln Ser Glu Pro Glu Asn
     130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                 165                 170                 175

Ser Val Tyr Ile Glu Leu Gly Ser Asp Ser Ser Glu Asp Thr Val Asn
             180                 185                 190

Lys Ala Thr Tyr Cys Ser Val Gly Asp Gln Glu Leu Leu Gln Ile Thr
         195                 200                 205

Pro Gln Gly Thr Arg Asp Glu Ile Ser Leu Asp Ser Ala Lys Lys Ala
     210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                 245                 250                 255

His Pro Glu Lys Tyr Gln Gly Ser Ser Val Ser Asn Leu His Val Glu
             260                 265                 270

Pro Cys Gly Thr Asn Thr His Ala Ser Ser Leu Gln His Glu Asn Ser
         275                 280                 285

Ser Leu Leu Leu Thr Lys Asp Arg Met Asn Val Glu Lys Ala Glu Phe
     290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                 325                 330                 335

Glu Lys Lys Val Asp Leu Asn Ala Asp Pro Leu Cys Glu Arg Lys Glu
             340                 345                 350

Trp Asn Lys Gln Lys Leu Pro Cys Ser Glu Asn Pro Arg Asp Thr Glu
         355                 360                 365

Asp Val Pro Trp Ile Thr Leu Asn Ser Ser Ile Gln Lys Val Asn Glu
     370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
```

|     |     |     | 405 |     |     |     |     | 410 |     |     |     | 415 |     |
| --- | --- | --- | --- | --- | --- | --- | --- | --- | --- | --- | --- | --- | --- |
| Asn | Glu | Val | Asp<br>420 | Glu | Tyr | Ser | Gly | Ser<br>425 | Glu | Lys | Ile | Asp<br>430 | Leu | Leu |
| Ala | Ser | Asp<br>435 | Pro | His | Glu | Ala | Leu<br>440 | Ile | Cys | Lys | Ser | Glu<br>445 | Arg | Val | His |
| Ser | Lys<br>450 | Ser | Val | Glu | Ser | Asn<br>455 | Ile | Glu | Asp | Lys | Ile<br>460 | Phe | Gly | Lys | Thr |
| Tyr<br>465 | Arg | Lys | Lys | Ala | Ser<br>470 | Leu | Pro | Asn | Leu | Ser<br>475 | His | Val | Thr | Glu | Asn<br>480 |
| Leu | Ile | Ile | Gly | Ala<br>485 | Phe | Val | Thr | Glu | Pro<br>490 | Gln | Ile | Ile | Gln | Glu<br>495 | Arg |
| Pro | Leu | Thr | Asn<br>500 | Lys | Leu | Lys | Arg | Lys<br>505 | Arg | Arg | Pro | Thr | Ser<br>510 | Gly | Leu |
| His | Pro | Glu<br>515 | Asp | Phe | Ile | Lys | Lys<br>520 | Ala | Asp | Leu | Ala | Val<br>525 | Gln | Lys | Thr |
| Pro | Glu<br>530 | Met | Ile | Asn | Gln | Gly<br>535 | Thr | Asn | Gln | Thr | Glu<br>540 | Gln | Asn | Gly | Gln |
| Val<br>545 | Met | Asn | Ile | Thr | Asn<br>550 | Ser | Gly | His | Glu | Asn<br>555 | Lys | Thr | Lys | Gly | Asp<br>560 |
| Ser | Ile | Gln | Asn | Glu<br>565 | Lys | Asn | Pro | Asn | Pro<br>570 | Ile | Glu | Ser | Leu | Glu<br>575 | Lys |
| Glu | Ser | Ala | Phe<br>580 | Lys | Thr | Lys | Ala | Glu<br>585 | Pro | Ile | Ser | Ser | Ser<br>590 | Ile | Ser |
| Asn | Met | Glu<br>595 | Leu | Glu | Leu | Asn | Ile<br>600 | His | Asn | Ser | Lys | Ala<br>605 | Pro | Lys | Lys |
| Asn | Arg<br>610 | Leu | Arg | Arg | Lys | Ser<br>615 | Ser | Thr | Arg | His | Ile<br>620 | His | Ala | Leu | Glu |
| Leu<br>625 | Val | Val | Ser | Arg | Asn<br>630 | Leu | Ser | Pro | Pro | Asn<br>635 | Cys | Thr | Glu | Leu | Gln<br>640 |
| Ile | Asp | Ser | Cys | Ser<br>645 | Ser | Ser | Glu | Glu | Ile<br>650 | Lys | Lys | Lys | Lys | Tyr<br>655 | Asn |
| Gln | Met | Pro | Val<br>660 | Arg | His | Ser | Arg | Asn<br>665 | Leu | Gln | Leu | Met | Glu<br>670 | Gly | Lys |
| Glu | Pro | Ala<br>675 | Thr | Gly | Ala | Lys | Lys<br>680 | Ser | Asn | Lys | Pro | Asn<br>685 | Glu | Gln | Thr |
| Ser | Lys<br>690 | Arg | His | Asp | Ser | Asp<br>695 | Thr | Phe | Pro | Glu | Leu<br>700 | Lys | Leu | Thr | Asn |
| Ala<br>705 | Pro | Gly | Ser | Phe | Thr<br>710 | Lys | Cys | Ser | Asn | Thr<br>715 | Ser | Glu | Leu | Lys | Glu<br>720 |
| Phe | Val | Asn | Pro | Ser<br>725 | Leu | Pro | Arg | Glu | Glu<br>730 | Lys | Glu | Glu | Lys | Leu<br>735 | Glu |
| Thr | Val | Lys | Val<br>740 | Ser | Asn | Asn | Ala | Glu<br>745 | Asp | Pro | Lys | Asp | Leu<br>750 | Met | Leu |
| Ser | Gly | Glu<br>755 | Arg | Val | Leu | Gln | Thr<br>760 | Glu | Arg | Ser | Val | Glu<br>765 |

( 2 ) INFORMATION FOR SEQ ID NO:20:

( i ) SEQUENCE CHARACTERISTICS:
        ( A ) LENGTH: 900 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

```
Met  Asp  Leu  Ser  Ala  Leu  Arg  Val  Glu  Glu  Val  Gln  Asn  Val  Ile  Asn
1                   5                        10                       15

Ala  Met  Gln  Lys  Ile  Leu  Glu  Cys  Pro  Ile  Cys  Leu  Glu  Leu  Ile  Lys
                20                       25                      30

Glu  Pro  Val  Ser  Thr  Lys  Cys  Asp  His  Ile  Phe  Cys  Lys  Phe  Cys  Met
               35                       40                      45

Leu  Lys  Leu  Leu  Asn  Gln  Lys  Gly  Pro  Ser  Gln  Cys  Pro  Leu  Cys
          50                       55                      60

Lys  Asn  Asp  Ile  Thr  Lys  Arg  Ser  Leu  Gln  Glu  Ser  Thr  Arg  Phe  Ser
65                       70                       75                           80

Gln  Leu  Val  Glu  Glu  Leu  Leu  Lys  Ile  Ile  Cys  Ala  Phe  Gln  Leu  Asp
               85                       90                              95

Thr  Gly  Leu  Glu  Tyr  Ala  Asn  Ser  Tyr  Asn  Phe  Ala  Lys  Lys  Glu  Asn
               100                      105                           110

Asn  Ser  Pro  Glu  His  Leu  Lys  Asp  Glu  Val  Ser  Ile  Ile  Gln  Ser  Met
          115                      120                          125

Gly  Tyr  Arg  Asn  Arg  Ala  Lys  Arg  Leu  Leu  Gln  Ser  Glu  Pro  Glu  Asn
          130                      135                          140

Pro  Ser  Leu  Gln  Glu  Thr  Ser  Leu  Ser  Val  Gln  Leu  Ser  Asn  Leu  Gly
145                      150                      155                           160

Thr  Val  Arg  Thr  Leu  Arg  Thr  Lys  Gln  Arg  Ile  Gln  Pro  Gln  Lys  Thr
                    165                      170                          175

Ser  Val  Tyr  Ile  Glu  Leu  Gly  Ser  Asp  Ser  Ser  Glu  Asp  Thr  Val  Asn
               180                      185                          190

Lys  Ala  Thr  Tyr  Cys  Ser  Val  Gly  Asp  Gln  Glu  Leu  Leu  Gln  Ile  Thr
               195                      200                          205

Pro  Gln  Gly  Thr  Arg  Asp  Glu  Ile  Ser  Leu  Asp  Ser  Ala  Lys  Lys  Ala
     210                      215                           220

Ala  Cys  Glu  Phe  Ser  Glu  Thr  Asp  Val  Thr  Asn  Thr  Glu  His  His  Gln
225                      230                      235                           240

Pro  Ser  Asn  Asn  Asp  Leu  Asn  Thr  Thr  Glu  Lys  Arg  Ala  Ala  Glu  Arg
                    245                      250                          255

His  Pro  Glu  Lys  Tyr  Gln  Gly  Ser  Ser  Val  Ser  Asn  Leu  His  Val  Glu
               260                      265                          270

Pro  Cys  Gly  Thr  Asn  Thr  His  Ala  Ser  Ser  Leu  Gln  His  Glu  Asn  Ser
          275                      280                          285

Ser  Leu  Leu  Leu  Thr  Lys  Asp  Arg  Met  Asn  Val  Glu  Lys  Ala  Glu  Phe
     290                      295                      300

Cys  Asn  Lys  Ser  Lys  Gln  Pro  Gly  Leu  Ala  Arg  Ser  Gln  His  Asn  Arg
305                      310                      315                           320

Trp  Ala  Gly  Ser  Lys  Glu  Thr  Cys  Asn  Asp  Arg  Arg  Thr  Pro  Ser  Thr
                    325                      330                          335

Glu  Lys  Lys  Val  Asp  Leu  Asn  Ala  Asp  Pro  Leu  Cys  Glu  Arg  Lys  Glu
               340                      345                          350

Trp  Asn  Lys  Gln  Lys  Leu  Pro  Cys  Ser  Glu  Asn  Pro  Arg  Asp  Thr  Glu
          355                      360                          365

Asp  Val  Pro  Trp  Ile  Thr  Leu  Asn  Ser  Ser  Ile  Gln  Lys  Val  Asn  Glu
     370                      375                      380

Trp  Phe  Ser  Arg  Ser  Asp  Glu  Leu  Leu  Gly  Ser  Asp  Ser  His  Asp
385                      390                      395                           400

Gly  Glu  Ser  Glu  Ser  Asn  Ala  Lys  Val  Ala  Asp  Val  Leu  Asp  Val  Leu
                    405                      410                          415

Asn  Glu  Val  Asp  Glu  Tyr  Ser  Gly  Ser  Ser  Glu  Lys  Ile  Asp  Leu  Leu
```

-continued

|     |     |     | 420 |     |     |     | 425 |     |     |     | 430 |     |     |
|---|---|---|---|---|---|---|---|---|---|---|---|---|---|
| Ala | Ser | Asp | Pro | His | Glu | Ala | Leu | Ile | Cys | Lys | Ser | Arg | Val | His |
|     |     | 435 |     |     |     |     | 440 |     |     |     | 445 |     |     |
| Ser | Lys | Ser | Val | Glu | Ser | Asn | Ile | Glu | Asp | Lys | Ile | Phe | Gly | Lys | Thr |
|     | 450 |     |     |     |     | 455 |     |     |     | 460 |     |     |     |
| Tyr | Arg | Lys | Lys | Ala | Ser | Leu | Pro | Asn | Leu | Ser | His | Val | Thr | Glu | Asn |
| 465 |     |     |     |     | 470 |     |     |     | 475 |     |     |     | 480 |
| Leu | Ile | Ile | Gly | Ala | Phe | Val | Thr | Glu | Pro | Gln | Ile | Ile | Gln | Glu | Arg |
|     |     |     |     | 485 |     |     |     | 490 |     |     |     | 495 |
| Pro | Leu | Thr | Asn | Lys | Leu | Lys | Arg | Lys | Arg | Pro | Thr | Ser | Gly | Leu |
|     |     |     | 500 |     |     |     | 505 |     |     |     | 510 |
| His | Pro | Glu | Asp | Phe | Ile | Lys | Lys | Ala | Asp | Leu | Ala | Val | Gln | Lys | Thr |
|     |     | 515 |     |     |     | 520 |     |     |     | 525 |
| Pro | Glu | Met | Ile | Asn | Gln | Gly | Thr | Asn | Gln | Thr | Glu | Gln | Asn | Gly | Gln |
|     | 530 |     |     |     | 535 |     |     |     | 540 |
| Val | Met | Asn | Ile | Thr | Asn | Ser | Gly | His | Glu | Asn | Lys | Thr | Lys | Gly | Asp |
| 545 |     |     |     | 550 |     |     |     | 555 |     |     |     | 560 |
| Ser | Ile | Gln | Asn | Glu | Lys | Asn | Pro | Asn | Pro | Ile | Glu | Ser | Leu | Glu | Lys |
|     |     |     | 565 |     |     |     | 570 |     |     |     | 575 |
| Glu | Ser | Ala | Phe | Lys | Thr | Lys | Ala | Glu | Pro | Ile | Ser | Ser | Ser | Ile | Ser |
|     |     | 580 |     |     |     | 585 |     |     |     | 590 |
| Asn | Met | Glu | Leu | Glu | Leu | Asn | Ile | His | Asn | Ser | Lys | Ala | Pro | Lys | Lys |
|     | 595 |     |     |     | 600 |     |     |     | 605 |
| Asn | Arg | Leu | Arg | Arg | Lys | Ser | Ser | Thr | Arg | His | Ile | His | Ala | Leu | Glu |
|     | 610 |     |     |     | 615 |     |     |     | 620 |
| Leu | Val | Val | Ser | Arg | Asn | Leu | Ser | Pro | Pro | Asn | Cys | Thr | Glu | Leu | Gln |
| 625 |     |     |     | 630 |     |     |     | 635 |     |     |     | 640 |
| Ile | Asp | Ser | Cys | Ser | Ser | Ser | Glu | Glu | Ile | Lys | Lys | Lys | Lys | Tyr | Asn |
|     |     |     | 645 |     |     |     | 650 |     |     |     | 655 |
| Gln | Met | Pro | Val | Arg | His | Ser | Arg | Asn | Leu | Gln | Leu | Met | Glu | Gly | Lys |
|     |     |     | 660 |     |     |     | 665 |     |     |     | 670 |
| Glu | Pro | Ala | Thr | Gly | Ala | Lys | Lys | Ser | Asn | Lys | Pro | Asn | Glu | Gln | Thr |
|     |     | 675 |     |     |     | 680 |     |     |     | 685 |
| Ser | Lys | Arg | His | Asp | Ser | Asp | Thr | Phe | Pro | Glu | Leu | Lys | Leu | Thr | Asn |
|     | 690 |     |     |     | 695 |     |     |     | 700 |
| Ala | Pro | Gly | Ser | Phe | Thr | Lys | Cys | Ser | Asn | Thr | Ser | Glu | Leu | Lys | Glu |
| 705 |     |     |     | 710 |     |     |     | 715 |     |     |     | 720 |
| Phe | Val | Asn | Pro | Ser | Leu | Pro | Arg | Glu | Lys | Glu | Glu | Lys | Leu | Glu |
|     |     |     | 725 |     |     |     | 730 |     |     |     | 735 |
| Thr | Val | Lys | Val | Ser | Asn | Asn | Ala | Glu | Asp | Pro | Lys | Asp | Leu | Met | Leu |
|     |     |     | 740 |     |     |     | 745 |     |     |     | 750 |
| Ser | Gly | Glu | Arg | Val | Leu | Gln | Thr | Glu | Arg | Ser | Val | Glu | Ser | Ser | Ser |
|     |     | 755 |     |     |     | 760 |     |     |     | 765 |
| Ile | Ser | Leu | Val | Pro | Gly | Thr | Asp | Tyr | Gly | Thr | Gln | Glu | Ser | Ile | Ser |
|     | 770 |     |     |     | 775 |     |     |     | 780 |
| Leu | Leu | Glu | Val | Ser | Thr | Leu | Gly | Lys | Ala | Lys | Thr | Glu | Pro | Asn | Lys |
| 785 |     |     |     | 790 |     |     |     | 795 |     |     |     | 800 |
| Cys | Val | Ser | Gln | Cys | Ala | Ala | Phe | Glu | Asn | Pro | Lys | Gly | Leu | Ile | His |
|     |     |     | 805 |     |     |     | 810 |     |     |     | 815 |
| Gly | Cys | Ser | Lys | Asp | Asn | Arg | Asn | Asp | Thr | Glu | Gly | Phe | Lys | Tyr | Pro |
|     |     |     | 820 |     |     |     | 825 |     |     |     | 830 |
| Leu | Gly | His | Glu | Val | Asn | His | Ser | Arg | Glu | Thr | Ser | Ile | Glu | Met | Glu |
|     |     | 835 |     |     |     | 840 |     |     |     | 845 |

| | | | | | | | | | | | | | | |
|---|---|---|---|---|---|---|---|---|---|---|---|---|---|---|
| Glu | Ser | Glu | Leu | Asp | Ala | Gln | Tyr | Leu | Gln | Asn | Thr | Phe | Lys | Val | Ser |
| | 850 | | | | 855 | | | | 860 | | | | | | |
| Lys | Arg | Gln | Ser | Phe | Ala | Pro | Phe | Ser | Asn | Pro | Gly | Asn | Ala | Glu | Glu |
| 865 | | | | 870 | | | | 875 | | | | | 880 | | |
| Glu | Cys | Ala | Thr | Phe | Ser | Ala | His | Ser | Gly | Ser | Leu | Lys | Thr | Lys | Ser |
| | | | 885 | | | | | 890 | | | | 895 | | | |
| Lys | Ser | His | Phe | | | | | | | | | | | | |
| | | | 900 | | | | | | | | | | | | |

( 2 ) INFORMATION FOR SEQ ID NO:21:

( i ) SEQUENCE CHARACTERISTICS:
        ( A ) LENGTH: 914 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

| | | | | | | | | | | | | | | |
|---|---|---|---|---|---|---|---|---|---|---|---|---|---|---|
| Met | Asp | Leu | Ser | Ala | Leu | Arg | Val | Glu | Glu | Val | Gln | Asn | Val | Ile | Asn |
| 1 | | | | 5 | | | | | 10 | | | | | 15 | |
| Ala | Met | Gln | Lys | Ile | Leu | Glu | Cys | Pro | Ile | Cys | Leu | Glu | Leu | Ile | Lys |
| | | | 20 | | | | 25 | | | | | 30 | | | |
| Glu | Pro | Val | Ser | Thr | Lys | Cys | Asp | His | Ile | Phe | Cys | Lys | Phe | Cys | Met |
| | | | 35 | | | | | 40 | | | | 45 | | | |
| Leu | Lys | Leu | Leu | Asn | Gln | Lys | Lys | Gly | Pro | Ser | Gln | Cys | Pro | Leu | Cys |
| | 50 | | | | | 55 | | | | | 60 | | | | |
| Lys | Asn | Asp | Ile | Thr | Lys | Arg | Ser | Leu | Gln | Glu | Ser | Thr | Arg | Phe | Ser |
| 65 | | | | | 70 | | | | | 75 | | | | | 80 |
| Gln | Leu | Val | Glu | Glu | Leu | Leu | Lys | Ile | Ile | Cys | Ala | Phe | Gln | Leu | Asp |
| | | | | 85 | | | | | 90 | | | | | 95 | |
| Thr | Gly | Leu | Glu | Tyr | Ala | Asn | Ser | Tyr | Asn | Phe | Ala | Lys | Lys | Glu | Asn |
| | | | 100 | | | | | 105 | | | | | 110 | | |
| Asn | Ser | Pro | Glu | His | Leu | Lys | Asp | Glu | Val | Ser | Ile | Ile | Gln | Ser | Met |
| | | 115 | | | | | 120 | | | | | 125 | | | |
| Gly | Tyr | Arg | Asn | Arg | Ala | Lys | Arg | Leu | Leu | Gln | Ser | Glu | Pro | Glu | Asn |
| | 130 | | | | 135 | | | | | 140 | | | | | |
| Pro | Ser | Leu | Gln | Glu | Thr | Ser | Leu | Ser | Val | Gln | Leu | Ser | Asn | Leu | Gly |
| 145 | | | | | 150 | | | | | 155 | | | | | 160 |
| Thr | Val | Arg | Thr | Leu | Arg | Thr | Lys | Gln | Arg | Ile | Gln | Pro | Gln | Lys | Thr |
| | | | | 165 | | | | | 170 | | | | | 175 | |
| Ser | Val | Tyr | Ile | Glu | Leu | Gly | Ser | Asp | Ser | Ser | Glu | Asp | Thr | Val | Asn |
| | | | 180 | | | | | 185 | | | | | 190 | | |
| Lys | Ala | Thr | Tyr | Cys | Ser | Val | Gly | Asp | Gln | Glu | Leu | Leu | Gln | Ile | Thr |
| | | 195 | | | | | 200 | | | | | 205 | | | |
| Pro | Gln | Gly | Thr | Arg | Asp | Glu | Ile | Ser | Leu | Asp | Ser | Ala | Lys | Lys | Ala |
| | 210 | | | | | 215 | | | | | 220 | | | | |
| Ala | Cys | Glu | Phe | Ser | Glu | Thr | Asp | Val | Thr | Asn | Thr | Glu | His | His | Gln |
| 225 | | | | | 230 | | | | | 235 | | | | | 240 |
| Pro | Ser | Asn | Asn | Asp | Leu | Asn | Thr | Thr | Glu | Lys | Arg | Ala | Ala | Glu | Arg |
| | | | | 245 | | | | | 250 | | | | | 255 | |
| His | Pro | Glu | Lys | Tyr | Gln | Gly | Ser | Ser | Val | Ser | Asn | Leu | His | Val | Glu |
| | | | 260 | | | | | 265 | | | | | 270 | | |
| Pro | Cys | Gly | Thr | Asn | Thr | His | Ala | Ser | Ser | Leu | Gln | His | Glu | Asn | Ser |
| | | 275 | | | | | 280 | | | | | 285 | | | |
| Ser | Leu | Leu | Leu | Thr | Lys | Asp | Arg | Met | Asn | Val | Glu | Lys | Ala | Glu | Phe |

-continued

|     | 290 |     |     |     | 295 |     |     |     | 300 |     |     |     |     |
|-----|-----|-----|-----|-----|-----|-----|-----|-----|-----|-----|-----|-----|-----|
| Cys 305 | Asn | Lys | Ser | Lys 310 | Gln | Pro | Gly | Leu | Ala 315 | Arg | Ser | Gln | His | Asn | Arg 320 |
| Trp | Ala | Gly | Ser | Lys 325 | Glu | Thr | Cys | Asn | Asp 330 | Arg | Arg | Thr | Pro | Ser | Thr 335 |
| Glu | Lys | Lys | Val | Asp 340 | Leu | Asn | Ala | Asp | Pro 345 | Leu | Cys | Glu | Arg | Lys 350 | Glu |
| Trp | Asn | Lys | Gln | Lys 355 | Leu | Pro | Cys | Ser | Glu 360 | Asn | Pro | Arg | Asp 365 | Thr | Glu |
| Asp | Val | Pro | Trp | Ile 370 | Thr | Leu | Asn | Ser | Ser 375 | Ile | Gln | Lys | Val 380 | Asn | Glu |
| Trp 385 | Phe | Ser | Arg | Ser | Asp 390 | Glu | Leu | Leu | Gly | Ser 395 | Asp | Asp | Ser | His | Asp 400 |
| Gly | Glu | Ser | Glu | Ser 405 | Asn | Ala | Lys | Val | Ala 410 | Asp | Val | Leu | Asp 415 | Val | Leu |
| Asn | Glu | Val | Asp 420 | Glu | Tyr | Ser | Gly | Ser 425 | Ser | Glu | Lys | Ile | Asp 430 | Leu | Leu |
| Ala | Ser | Asp 435 | Pro | His | Glu | Ala | Leu 440 | Ile | Cys | Lys | Ser | Glu 445 | Arg | Val | His |
| Ser | Lys 450 | Ser | Val | Glu | Ser | Asn 455 | Ile | Glu | Asp | Lys | Ile 460 | Phe | Gly | Lys | Thr |
| Tyr 465 | Arg | Lys | Lys | Ala | Ser 470 | Leu | Pro | Asn | Leu | Ser 475 | His | Val | Thr | Glu | Asn 480 |
| Leu | Ile | Ile | Gly | Ala 485 | Phe | Val | Thr | Glu | Pro 490 | Gln | Ile | Ile | Gln | Glu 495 | Arg |
| Pro | Leu | Thr | Asn 500 | Lys | Leu | Lys | Arg | Lys 505 | Arg | Arg | Pro | Thr | Ser 510 | Gly | Leu |
| His | Pro | Glu | Asp 515 | Phe | Ile | Lys | Lys 520 | Ala | Asp | Leu | Ala | Val 525 | Gln | Lys | Thr |
| Pro | Glu 530 | Met | Ile | Asn | Gln | Gly 535 | Thr | Asn | Gln | Thr | Glu 540 | Gln | Asn | Gly | Gln |
| Val 545 | Met | Asn | Ile | Thr | Asn 550 | Ser | Gly | His | Glu | Asn 555 | Lys | Thr | Lys | Gly | Asp 560 |
| Ser | Ile | Gln | Asn | Glu 565 | Lys | Asn | Pro | Asn | Pro 570 | Ile | Glu | Ser | Leu | Glu 575 | Lys |
| Glu | Ser | Ala | Phe 580 | Lys | Thr | Lys | Ala | Glu 585 | Pro | Ile | Ser | Ser | Ser 590 | Ile | Ser |
| Asn | Met | Glu 595 | Leu | Glu | Leu | Asn | Ile 600 | His | Asn | Ser | Lys | Ala 605 | Pro | Lys | Lys |
| Asn | Arg 610 | Leu | Arg | Arg | Lys | Ser 615 | Ser | Thr | Arg | His | Ile 620 | His | Ala | Leu | Glu |
| Leu | Val 625 | Val | Ser | Arg | Asn 630 | Leu | Ser | Pro | Pro | Asn 635 | Cys | Thr | Glu | Leu | Gln 640 |
| Ile | Asp | Ser | Cys | Ser 645 | Ser | Ser | Glu | Glu | Ile 650 | Lys | Lys | Lys | Lys | Tyr 655 | Asn |
| Gln | Met | Pro | Val 660 | Arg | His | Ser | Arg | Asn 665 | Leu | Gln | Leu | Met | Glu 670 | Gly | Lys |
| Glu | Pro | Ala | Thr 675 | Gly | Ala | Lys | Lys | Ser 680 | Asn | Lys | Pro | Asn | Glu 685 | Gln | Thr |
| Ser | Lys 690 | Arg | His | Asp | Ser | Asp 695 | Thr | Phe | Pro | Glu | Leu 700 | Lys | Leu | Thr | Asn |
| Ala 705 | Pro | Gly | Ser | Phe | Thr 710 | Lys | Cys | Ser | Asn | Thr 715 | Ser | Glu | Leu | Lys | Glu 720 |

```
Phe Val Asn Pro Ser Leu Pro Arg Glu Glu Lys Glu Glu Lys Leu Glu
            725             730             735

Thr Val Lys Val Ser Asn Asn Ala Glu Asp Pro Lys Asp Leu Met Leu
            740             745             750

Ser Gly Glu Arg Val Leu Gln Thr Glu Arg Ser Val Glu Ser Ser Ser
            755             760             765

Ile Ser Leu Val Pro Gly Thr Asp Tyr Gly Thr Gln Glu Ser Ile Ser
            770             775             780

Leu Leu Glu Val Ser Thr Leu Gly Lys Ala Lys Thr Glu Pro Asn Lys
785             790             795             800

Cys Val Ser Gln Cys Ala Ala Phe Glu Asn Pro Lys Gly Leu Ile His
            805             810             815

Gly Cys Ser Lys Asp Asn Arg Asn Asp Thr Glu Gly Phe Lys Tyr Pro
            820             825             830

Leu Gly His Glu Val Asn His Ser Arg Glu Thr Ser Ile Glu Met Glu
            835             840             845

Glu Ser Glu Leu Asp Ala Gln Tyr Leu Gln Asn Thr Phe Lys Val Ser
            850             855             860

Lys Arg Gln Ser Phe Ala Pro Phe Ser Asn Pro Gly Asn Ala Glu Glu
865             870             875             880

Glu Cys Ala Thr Phe Ser Ala His Ser Gly Ser Leu Lys Lys Gln Ser
            885             890             895

Pro Lys Val Thr Phe Glu Cys Glu Gln Lys Glu Glu Asn Gln Gly Lys
            900             905             910

Asn Glu
```

( 2 ) INFORMATION FOR SEQ ID NO:22:

( i ) SEQUENCE CHARACTERISTICS:
        ( A ) LENGTH: 1202 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

```
Met Asp Leu Ser Ala Leu Arg Val Glu Glu Val Gln Asn Val Ile Asn
1               5               10              15

Ala Met Gln Lys Ile Leu Glu Cys Pro Ile Cys Leu Glu Leu Ile Lys
            20              25              30

Glu Pro Val Ser Thr Lys Cys Asp His Ile Phe Cys Lys Phe Cys Met
            35              40              45

Leu Lys Leu Leu Asn Gln Lys Lys Gly Pro Ser Gln Cys Pro Leu Cys
            50              55              60

Lys Asn Asp Ile Thr Lys Arg Ser Leu Gln Glu Ser Thr Arg Phe Ser
65              70              75              80

Gln Leu Val Glu Glu Leu Leu Lys Ile Ile Cys Ala Phe Gln Leu Asp
            85              90              95

Thr Gly Leu Glu Tyr Ala Asn Ser Tyr Asn Phe Ala Lys Lys Glu Asn
            100             105             110

Asn Ser Pro Glu His Leu Lys Asp Glu Val Ser Ile Ile Gln Ser Met
            115             120             125

Gly Tyr Arg Asn Arg Ala Lys Arg Leu Leu Gln Ser Glu Pro Glu Asn
            130             135             140

Pro Ser Leu Gln Glu Thr Ser Leu Ser Val Gln Leu Ser Asn Leu Gly
145             150             155             160
```

-continued

```
Thr  Val  Arg  Thr  Leu  Arg  Thr  Lys  Gln  Arg  Ile  Gln  Pro  Gln  Lys  Thr
               165                170                          175

Ser  Val  Tyr  Ile  Glu  Leu  Gly  Ser  Asp  Ser  Glu  Asp  Thr  Val  Asn
               180                185                     190

Lys  Ala  Thr  Tyr  Cys  Ser  Val  Gly  Asp  Gln  Glu  Leu  Leu  Gln  Ile  Thr
               195                200                     205

Pro  Gln  Gly  Thr  Arg  Asp  Glu  Ile  Ser  Leu  Asp  Ser  Ala  Lys  Lys  Ala
     210                     215                     220

Ala  Cys  Glu  Phe  Ser  Glu  Thr  Asp  Val  Thr  Asn  Thr  Glu  His  His  Gln
225                      230                235                          240

Pro  Ser  Asn  Asn  Asp  Leu  Asn  Thr  Thr  Glu  Lys  Arg  Ala  Ala  Glu  Arg
               245                     250                          255

His  Pro  Glu  Lys  Tyr  Gln  Gly  Ser  Ser  Val  Ser  Asn  Leu  His  Val  Glu
               260                265                          270

Pro  Cys  Gly  Thr  Asn  Thr  His  Ala  Ser  Ser  Leu  Gln  His  Glu  Asn  Ser
          275                     280                     285

Ser  Leu  Leu  Leu  Thr  Lys  Asp  Arg  Met  Asn  Val  Glu  Lys  Ala  Glu  Phe
     290                     295                300

Cys  Asn  Lys  Ser  Lys  Gln  Pro  Gly  Leu  Ala  Arg  Ser  Gln  His  Asn  Arg
305                      310                315                          320

Trp  Ala  Gly  Ser  Lys  Glu  Thr  Cys  Asn  Asp  Arg  Arg  Thr  Pro  Ser  Thr
                    325                     330                     335

Glu  Lys  Lys  Val  Asp  Leu  Asn  Ala  Asp  Pro  Leu  Cys  Glu  Arg  Lys  Glu
               340                     345                     350

Trp  Asn  Lys  Gln  Lys  Leu  Pro  Cys  Ser  Glu  Asn  Pro  Arg  Asp  Thr  Glu
          355                     360                365

Asp  Val  Pro  Trp  Ile  Thr  Leu  Asn  Ser  Ser  Ile  Gln  Lys  Val  Asn  Glu
     370                     375                380

Trp  Phe  Ser  Arg  Ser  Asp  Glu  Leu  Leu  Gly  Ser  Asp  Asp  Ser  His  Asp
385                      390                     395                     400

Gly  Glu  Ser  Glu  Ser  Asn  Ala  Lys  Val  Ala  Asp  Val  Leu  Asp  Val  Leu
                    405                     410                     415

Asn  Glu  Val  Asp  Glu  Tyr  Ser  Gly  Ser  Ser  Glu  Lys  Ile  Asp  Leu  Leu
               420                     425                     430

Ala  Ser  Asp  Pro  His  Glu  Ala  Leu  Ile  Cys  Lys  Ser  Glu  Arg  Val  His
          435                     440                     445

Ser  Lys  Ser  Val  Glu  Ser  Asn  Ile  Glu  Asp  Lys  Ile  Phe  Gly  Lys  Thr
     450                     455                     460

Tyr  Arg  Lys  Lys  Ala  Ser  Leu  Pro  Asn  Leu  Ser  His  Val  Thr  Glu  Asn
465                      470                     475                     480

Leu  Ile  Ile  Gly  Ala  Phe  Val  Thr  Glu  Pro  Gln  Ile  Ile  Gln  Glu  Arg
                    485                     490                     495

Pro  Leu  Thr  Asn  Lys  Leu  Lys  Arg  Lys  Arg  Arg  Pro  Thr  Ser  Gly  Leu
               500                     505                     510

His  Pro  Glu  Asp  Phe  Ile  Lys  Lys  Ala  Asp  Leu  Ala  Val  Gln  Lys  Thr
               515                     520                     525

Pro  Glu  Met  Ile  Asn  Gln  Gly  Thr  Asn  Gln  Thr  Glu  Gln  Asn  Gly  Gln
     530                     535                     540

Val  Met  Asn  Ile  Thr  Asn  Ser  Gly  His  Glu  Asn  Lys  Thr  Lys  Gly  Asp
545                      550                     555                     560

Ser  Ile  Gln  Asn  Glu  Lys  Asn  Pro  Asn  Pro  Ile  Glu  Ser  Leu  Glu  Lys
                    565                     570                     575

Glu  Ser  Ala  Phe  Lys  Thr  Lys  Ala  Glu  Pro  Ile  Ser  Ser  Ser  Ile  Ser
```

|   |   |   |   |   | 580 |   |   |   |   | 585 |   |   |   |   | 590 |   |
|---|---|---|---|---|---|---|---|---|---|---|---|---|---|---|---|---|
| Asn | Met | Glu | Leu | Glu | Leu | Asn | Ile | His | Asn | Ser | Lys | Ala | Pro | Lys | Lys |
|   |   | 595 |   |   |   | 600 |   |   |   | 605 |   |   |   |   |   |
| Asn | Arg | Leu | Arg | Arg | Lys | Ser | Ser | Thr | Arg | His | Ile | His | Ala | Leu | Glu |
|   | 610 |   |   |   | 615 |   |   |   |   | 620 |   |   |   |   |   |
| Leu | Val | Val | Ser | Arg | Asn | Leu | Ser | Pro | Pro | Asn | Cys | Thr | Glu | Leu | Gln |
| 625 |   |   |   | 630 |   |   |   |   | 635 |   |   |   |   |   | 640 |
| Ile | Asp | Ser | Cys | Ser | Ser | Ser | Glu | Glu | Ile | Lys | Lys | Lys | Lys | Tyr | Asn |
|   |   |   |   | 645 |   |   |   |   | 650 |   |   |   |   | 655 |   |
| Gln | Met | Pro | Val | Arg | His | Ser | Arg | Asn | Leu | Gln | Leu | Met | Glu | Gly | Lys |
|   |   |   | 660 |   |   |   |   | 665 |   |   |   | 670 |   |   |   |
| Glu | Pro | Ala | Thr | Gly | Ala | Lys | Lys | Ser | Asn | Lys | Pro | Asn | Glu | Gln | Thr |
|   |   | 675 |   |   |   |   | 680 |   |   |   | 685 |   |   |   |   |
| Ser | Lys | Arg | His | Asp | Ser | Asp | Thr | Phe | Pro | Glu | Leu | Lys | Leu | Thr | Asn |
|   | 690 |   |   |   | 695 |   |   |   |   | 700 |   |   |   |   |   |
| Ala | Pro | Gly | Ser | Phe | Thr | Lys | Cys | Ser | Asn | Thr | Ser | Glu | Leu | Lys | Glu |
| 705 |   |   |   |   | 710 |   |   |   |   | 715 |   |   |   |   | 720 |
| Phe | Val | Asn | Pro | Ser | Leu | Pro | Arg | Glu | Glu | Lys | Glu | Glu | Lys | Leu | Glu |
|   |   |   |   | 725 |   |   |   |   | 730 |   |   |   |   | 735 |   |
| Thr | Val | Lys | Val | Ser | Asn | Asn | Ala | Glu | Asp | Pro | Lys | Asp | Leu | Met | Leu |
|   |   |   | 740 |   |   |   |   | 745 |   |   |   | 750 |   |   |   |
| Ser | Gly | Glu | Arg | Val | Leu | Gln | Thr | Glu | Arg | Ser | Val | Glu | Ser | Ser | Ser |
|   |   | 755 |   |   |   |   | 760 |   |   |   | 765 |   |   |   |   |
| Ile | Ser | Leu | Val | Pro | Gly | Thr | Asp | Tyr | Gly | Thr | Gln | Glu | Ser | Ile | Ser |
|   | 770 |   |   |   |   | 775 |   |   |   |   | 780 |   |   |   |   |
| Leu | Leu | Glu | Val | Ser | Thr | Leu | Gly | Lys | Ala | Lys | Thr | Glu | Pro | Asn | Lys |
| 785 |   |   |   |   | 790 |   |   |   |   | 795 |   |   |   |   | 800 |
| Cys | Val | Ser | Gln | Cys | Ala | Ala | Phe | Glu | Asn | Pro | Lys | Gly | Leu | Ile | His |
|   |   |   |   | 805 |   |   |   |   | 810 |   |   |   |   | 815 |   |
| Gly | Cys | Ser | Lys | Asp | Asn | Arg | Asn | Asp | Thr | Glu | Gly | Phe | Lys | Tyr | Pro |
|   |   |   |   | 820 |   |   |   |   | 825 |   |   |   |   | 830 |   |
| Leu | Gly | His | Glu | Val | Asn | His | Ser | Arg | Glu | Thr | Ser | Ile | Glu | Met | Glu |
|   |   | 835 |   |   |   |   | 840 |   |   |   |   | 845 |   |   |   |
| Glu | Ser | Glu | Leu | Asp | Ala | Gln | Tyr | Leu | Gln | Asn | Thr | Phe | Lys | Val | Ser |
|   | 850 |   |   |   |   | 855 |   |   |   |   | 860 |   |   |   |   |
| Lys | Arg | Gln | Ser | Phe | Ala | Pro | Phe | Ser | Asn | Pro | Gly | Asn | Ala | Glu | Glu |
| 865 |   |   |   |   | 870 |   |   |   |   | 875 |   |   |   |   | 880 |
| Glu | Cys | Ala | Thr | Phe | Ser | Ala | His | Ser | Gly | Ser | Leu | Lys | Lys | Gln | Ser |
|   |   |   |   | 885 |   |   |   |   | 890 |   |   |   |   | 895 |   |
| Pro | Lys | Val | Thr | Phe | Glu | Cys | Glu | Gln | Lys | Glu | Glu | Asn | Gln | Gly | Lys |
|   |   |   | 900 |   |   |   |   | 905 |   |   |   |   | 910 |   |   |
| Asn | Glu | Ser | Asn | Ile | Lys | Pro | Val | Gln | Thr | Val | Asn | Ile | Thr | Ala | Gly |
|   |   | 915 |   |   |   |   | 920 |   |   |   |   | 925 |   |   |   |
| Phe | Pro | Val | Val | Gly | Gln | Lys | Asp | Lys | Pro | Val | Asp | Asn | Ala | Lys | Cys |
|   | 930 |   |   |   |   | 935 |   |   |   |   | 940 |   |   |   |   |
| Ser | Ile | Lys | Gly | Gly | Ser | Arg | Phe | Cys | Leu | Ser | Ser | Gln | Phe | Arg | Gly |
| 945 |   |   |   |   | 950 |   |   |   |   | 955 |   |   |   |   | 960 |
| Asn | Glu | Thr | Gly | Leu | Ile | Thr | Pro | Asn | Lys | His | Gly | Leu | Leu | Gln | Asn |
|   |   |   |   | 965 |   |   |   |   | 970 |   |   |   |   | 975 |   |
| Pro | Tyr | Arg | Ile | Pro | Pro | Leu | Phe | Pro | Ile | Lys | Ser | Phe | Val | Lys | Thr |
|   |   |   | 980 |   |   |   |   | 985 |   |   |   | 990 |   |   |   |
| Lys | Cys | Lys | Lys | Asn | Leu | Leu | Glu | Glu | Asn | Phe | Glu | Glu | His | Ser | Met |
|   |   | 995 |   |   |   |   | 1000 |   |   |   | 1005 |   |   |   |   |

-continued

```
Ser  Pro  Glu  Arg  Glu  Met  Gly  Asn  Glu  Asn  Ile  Pro  Ser  Thr  Val  Ser
     1010                1015                1020

Thr  Ile  Ser  Arg  Asn  Asn  Ile  Arg  Glu  Asn  Val  Phe  Lys  Glu  Ala  Ser
1025                1030                1035                          1040

Ser  Ser  Asn  Ile  Asn  Glu  Val  Gly  Ser  Ser  Thr  Asn  Glu  Val  Gly  Ser
               1045                1050                          1055

Ser  Ile  Asn  Glu  Ile  Gly  Ser  Ser  Asp  Glu  Asn  Ile  Gln  Ala  Glu  Leu
               1060                1065                1070

Gly  Arg  Asn  Arg  Gly  Pro  Lys  Leu  Asn  Ala  Met  Leu  Arg  Leu  Gly  Val
          1075                1080                     1085

Leu  Gln  Pro  Glu  Val  Tyr  Lys  Gln  Ser  Leu  Pro  Gly  Ser  Asn  Cys  Lys
          1090                1095                1100

His  Pro  Glu  Ile  Lys  Lys  Gln  Glu  Tyr  Glu  Glu  Val  Val  Gln  Thr  Val
1105                1110                1115                          1120

Asn  Thr  Asp  Phe  Ser  Pro  Tyr  Leu  Ile  Ser  Asp  Asn  Leu  Glu  Gln  Pro
                    1125                1130                     1135

Met  Gly  Ser  Ser  His  Ala  Ser  Gln  Val  Cys  Ser  Glu  Thr  Pro  Asp  Asp
               1140                1145                     1150

Leu  Leu  Asp  Asp  Gly  Glu  Ile  Lys  Glu  Asp  Thr  Ser  Phe  Ala  Glu  Asn
               1155                1160                1165

Asp  Ile  Lys  Glu  Ser  Ser  Ala  Val  Phe  Ser  Lys  Ser  Val  Gln  Lys  Gly
     1170                1175                     1180

Glu  Leu  Ser  Arg  Ser  Pro  Ser  Pro  Phe  Thr  His  Thr  His  Leu  Ala  Gln
1185                1190                1195                          1200

Gly  Tyr
```

(2) INFORMATION FOR SEQ ID NO:23:

(i) SEQUENCE CHARACTERISTICS:
        (A) LENGTH: 1363 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Met  Asp  Leu  Ser  Ala  Leu  Arg  Val  Glu  Glu  Val  Gln  Asn  Val  Ile  Asn
1              5                     10                          15

Ala  Met  Gln  Lys  Ile  Leu  Glu  Cys  Pro  Ile  Cys  Leu  Glu  Leu  Ile  Lys
               20                     25                     30

Glu  Pro  Val  Ser  Thr  Lys  Cys  Asp  His  Ile  Phe  Cys  Lys  Phe  Cys  Met
          35                     40                     45

Leu  Lys  Leu  Leu  Asn  Gln  Lys  Lys  Gly  Pro  Ser  Gln  Cys  Pro  Leu  Cys
     50                     55                     60

Lys  Asn  Asp  Ile  Thr  Lys  Arg  Ser  Leu  Gln  Glu  Ser  Thr  Arg  Phe  Ser
65                     70                     75                          80

Gln  Leu  Val  Glu  Glu  Leu  Leu  Lys  Ile  Ile  Cys  Ala  Phe  Gln  Leu  Asp
               85                     90                          95

Thr  Gly  Leu  Glu  Tyr  Ala  Asn  Ser  Tyr  Asn  Phe  Ala  Lys  Lys  Glu  Asn
               100                    105                    110

Asn  Ser  Pro  Glu  His  Leu  Lys  Asp  Glu  Val  Ser  Ile  Ile  Gln  Ser  Met
          115                    120                    125

Gly  Tyr  Arg  Asn  Arg  Ala  Lys  Arg  Leu  Leu  Gln  Ser  Glu  Pro  Glu  Asn
          130                    135                    140

Pro  Ser  Leu  Gln  Glu  Thr  Ser  Leu  Ser  Val  Gln  Leu  Ser  Asn  Leu  Gly
145                    150                    155                         160
```

-continued

| | | | | | | | | | | | | | | |
|---|---|---|---|---|---|---|---|---|---|---|---|---|---|---|
| Thr | Val | Arg | Thr | Leu 165 | Arg | Thr | Lys | Gln | Arg 170 | Ile | Gln | Pro | Gln | Lys 175 | Thr |
| Ser | Val | Tyr | Ile 180 | Glu | Leu | Gly | Ser | Asp 185 | Ser | Ser | Glu | Asp 190 | Thr | Val | Asn |
| Lys | Ala | Thr 195 | Tyr | Cys | Ser | Val | Gly 200 | Asp | Gln | Glu | Leu | Leu 205 | Gln | Ile | Thr |
| Pro | Gln 210 | Gly | Thr | Arg | Asp | Glu 215 | Ile | Ser | Leu | Asp | Ser 220 | Ala | Lys | Lys | Ala |
| Ala 225 | Cys | Glu | Phe | Ser | Glu 230 | Thr | Asp | Val | Thr | Asn 235 | Thr | Glu | His | His | Gln 240 |
| Pro | Ser | Asn | Asn | Asp 245 | Leu | Asn | Thr | Thr | Glu 250 | Lys | Arg | Ala | Ala | Glu 255 | Arg |
| His | Pro | Glu | Lys 260 | Tyr | Gln | Gly | Ser | Ser 265 | Val | Ser | Asn | Leu | His 270 | Val | Glu |
| Pro | Cys | Gly 275 | Thr | Asn | Thr | His | Ala 280 | Ser | Ser | Leu | Gln | His 285 | Glu | Asn | Ser |
| Ser | Leu 290 | Leu | Leu | Thr | Lys | Asp 295 | Arg | Met | Asn | Val | Glu 300 | Lys | Ala | Glu | Phe |
| Cys 305 | Asn | Lys | Ser | Lys | Gln 310 | Pro | Gly | Leu | Ala | Arg 315 | Ser | Gln | His | Asn | Arg 320 |
| Trp | Ala | Gly | Ser | Lys 325 | Glu | Thr | Cys | Asn | Asp 330 | Arg | Arg | Thr | Pro | Ser 335 | Thr |
| Glu | Lys | Lys | Val 340 | Asp | Leu | Asn | Ala | Asp 345 | Pro | Leu | Cys | Glu | Arg 350 | Lys | Glu |
| Trp | Asn | Lys 355 | Gln | Lys | Leu | Pro | Cys 360 | Ser | Glu | Asn | Pro | Arg 365 | Asp | Thr | Glu |
| Asp | Val 370 | Pro | Trp | Ile | Thr | Leu 375 | Asn | Ser | Ser | Ile | Gln 380 | Lys | Val | Asn | Glu |
| Trp 385 | Phe | Ser | Arg | Ser | Asp 390 | Glu | Leu | Leu | Gly | Ser 395 | Asp | Asp | Ser | His | Asp 400 |
| Gly | Glu | Ser | Glu | Ser 405 | Asn | Ala | Lys | Val | Ala 410 | Asp | Val | Leu | Asp | Val 415 | Leu |
| Asn | Glu | Val | Asp 420 | Glu | Tyr | Ser | Gly | Ser 425 | Ser | Glu | Lys | Ile | Asp 430 | Leu | Leu |
| Ala | Ser | Asp 435 | Pro | His | Glu | Ala | Leu 440 | Ile | Cys | Lys | Ser | Glu 445 | Arg | Val | His |
| Ser | Lys 450 | Ser | Val | Glu | Ser | Asn 455 | Ile | Glu | Asp | Lys | Ile 460 | Phe | Gly | Lys | Thr |
| Tyr 465 | Arg | Lys | Lys | Ala | Ser 470 | Leu | Pro | Asn | Leu | Ser 475 | His | Val | Thr | Glu | Asn 480 |
| Leu | Ile | Ile | Gly | Ala 485 | Phe | Val | Thr | Glu | Pro 490 | Gln | Ile | Ile | Gln | Glu 495 | Arg |
| Pro | Leu | Thr | Asn 500 | Lys | Leu | Lys | Arg | Lys 505 | Arg | Arg | Pro | Thr | Ser 510 | Gly | Leu |
| His | Pro | Glu 515 | Asp | Phe | Ile | Lys | Lys 520 | Ala | Asp | Leu | Ala | Val 525 | Gln | Lys | Thr |
| Pro | Glu 530 | Met | Ile | Asn | Gln | Gly 535 | Thr | Asn | Gln | Thr | Glu 540 | Gln | Asn | Gly | Gln |
| Val 545 | Met | Asn | Ile | Thr | Asn 550 | Ser | Gly | His | Glu | Asn 555 | Lys | Thr | Lys | Gly | Asp 560 |
| Ser | Ile | Gln | Asn | Glu 565 | Lys | Asn | Pro | Asn | Pro 570 | Ile | Glu | Ser | Leu | Glu 575 | Lys |
| Glu | Ser | Ala | Phe | Lys | Thr | Lys | Ala | Glu | Pro | Ile | Ser | Ser | Ser | Ile | Ser |

-continued

|     |     |     |     |     | 580 |     |     |     |     | 585 |     |     |     |     | 590 |     |     |
| --- | --- | --- | --- | --- | --- | --- | --- | --- | --- | --- | --- | --- | --- | --- | --- | --- | --- |
| Asn | Met | Glu<br>595 | Leu | Glu | Leu | Asn | Ile<br>600 | His | Asn | Ser | Lys<br>605 | Ala | Pro | Lys | Lys |
| Asn | Arg<br>610 | Leu | Arg | Arg | Lys<br>615 | Ser | Ser | Thr | Arg<br>620 | His | Ile | His | Ala | Leu | Glu |
| Leu<br>625 | Val | Val | Ser | Arg | Asn<br>630 | Leu | Ser | Pro | Pro<br>635 | Asn | Cys | Thr | Glu | Leu | Gln<br>640 |
| Ile | Asp | Ser | Cys | Ser<br>645 | Ser | Ser | Glu | Glu | Ile<br>650 | Lys | Lys | Lys | Lys | Tyr | Asn<br>655 |
| Gln | Met | Pro | Val<br>660 | Arg | His | Ser | Arg | Asn<br>665 | Leu | Gln | Leu | Met | Glu<br>670 | Gly | Lys |
| Glu | Pro | Ala<br>675 | Thr | Gly | Ala | Lys | Lys<br>680 | Ser | Asn | Lys | Pro | Asn<br>685 | Glu | Gln | Thr |
| Ser | Lys<br>690 | Arg | His | Asp | Ser | Asp<br>695 | Thr | Phe | Pro | Glu | Leu<br>700 | Lys | Leu | Thr | Asn |
| Ala<br>705 | Pro | Gly | Ser | Phe | Thr<br>710 | Lys | Cys | Ser | Asn | Thr<br>715 | Ser | Glu | Leu | Lys | Glu<br>720 |
| Phe | Val | Asn | Pro | Ser<br>725 | Leu | Pro | Arg | Glu | Glu<br>730 | Lys | Glu | Glu | Lys | Leu<br>735 | Glu |
| Thr | Val | Lys | Val<br>740 | Ser | Asn | Asn | Ala | Glu<br>745 | Asp | Pro | Lys | Asp | Leu<br>750 | Met | Leu |
| Ser | Gly | Glu | Arg<br>755 | Val | Leu | Gln | Thr | Glu<br>760 | Arg | Ser | Val | Glu<br>765 | Ser | Ser | Ser |
| Ile | Ser | Leu<br>770 | Val | Pro | Gly | Thr<br>775 | Asp | Tyr | Gly | Thr | Gln<br>780 | Glu | Ser | Ile | Ser |
| Leu<br>785 | Leu | Glu | Val | Ser | Thr<br>790 | Leu | Gly | Lys | Ala | Lys<br>795 | Thr | Glu | Pro | Asn | Lys<br>800 |
| Cys | Val | Ser | Gln | Cys<br>805 | Ala | Ala | Phe | Glu | Asn<br>810 | Pro | Lys | Gly | Leu | Ile | His<br>815 |
| Gly | Cys | Ser | Lys<br>820 | Asp | Asn | Arg | Asn | Asp<br>825 | Thr | Glu | Gly | Phe | Lys<br>830 | Tyr | Pro |
| Leu | Gly | His<br>835 | Glu | Val | Asn | His | Ser<br>840 | Arg | Glu | Thr | Ser | Ile<br>845 | Glu | Met | Glu |
| Glu | Ser<br>850 | Glu | Leu | Asp | Ala | Gln<br>855 | Tyr | Leu | Gln | Asn | Thr<br>860 | Phe | Lys | Val | Ser |
| Lys<br>865 | Arg | Gln | Ser | Phe | Ala<br>870 | Pro | Phe | Ser | Asn | Pro<br>875 | Gly | Asn | Ala | Glu | Glu<br>880 |
| Glu | Cys | Ala | Thr | Phe<br>885 | Ser | Ala | His | Ser | Gly<br>890 | Ser | Leu | Lys | Lys | Gln<br>895 | Ser |
| Pro | Lys | Val | Thr<br>900 | Phe | Glu | Cys | Glu | Gln<br>905 | Lys | Glu | Glu | Asn | Gln<br>910 | Gly | Lys |
| Asn | Glu | Ser<br>915 | Asn | Ile | Lys | Pro | Val<br>920 | Gln | Thr | Val | Asn | Ile<br>925 | Thr | Ala | Gly |
| Phe | Pro | Val<br>930 | Val | Gly | Gln | Lys<br>935 | Asp | Lys | Pro | Val | Asp<br>940 | Asn | Ala | Lys | Cys |
| Ser<br>945 | Ile | Lys | Gly | Gly | Ser<br>950 | Arg | Phe | Cys | Leu | Ser<br>955 | Ser | Gln | Phe | Arg | Gly<br>960 |
| Asn | Glu | Thr | Gly | Leu<br>965 | Ile | Thr | Pro | Asn | Lys<br>970 | His | Gly | Leu | Leu | Gln | Asn<br>975 |
| Pro | Tyr | Arg | Ile<br>980 | Pro | Pro | Leu | Phe | Pro<br>985 | Ile | Lys | Ser | Phe | Val<br>990 | Lys | Thr |
| Lys | Cys | Lys<br>995 | Lys | Asn | Leu | Leu | Glu<br>1000 | Glu | Asn | Phe | Glu | Glu<br>1005 | His | Ser | Met |

Ser Pro Glu Arg Glu Met Gly Asn Glu Asn Ile Pro Ser Thr Val Ser
1010                    1015                    1020

Thr Ile Ser Arg Asn Asn Ile Arg Glu Asn Val Phe Lys Glu Ala Ser
1025                    1030                    1035                    1040

Ser Ser Asn Ile Asn Glu Val Gly Ser Ser Thr Asn Glu Val Gly Ser
                    1045                    1050                    1055

Ser Ile Asn Glu Ile Gly Ser Ser Asp Glu Asn Ile Gln Ala Glu Leu
            1060                    1065                    1070

Gly Arg Asn Arg Gly Pro Lys Leu Asn Ala Met Leu Arg Leu Gly Val
        1075                    1080                    1085

Leu Gln Pro Glu Val Tyr Lys Gln Ser Leu Pro Gly Ser Asn Cys Lys
            1090                    1095                    1100

His Pro Glu Ile Lys Lys Gln Glu Tyr Glu Glu Val Val Gln Thr Val
1105                    1110                    1115                    1120

Asn Thr Asp Phe Ser Pro Tyr Leu Ile Ser Asp Asn Leu Glu Gln Pro
                    1125                    1130                    1135

Met Gly Ser Ser His Ala Ser Gln Val Cys Ser Glu Thr Pro Asp Asp
                1140                    1145                    1150

Leu Leu Asp Asp Gly Glu Ile Lys Glu Asp Thr Ser Phe Ala Glu Asn
            1155                    1160                    1165

Asp Ile Lys Glu Ser Ser Ala Val Phe Ser Lys Ser Val Gln Lys Gly
            1170                    1175                    1180

Glu Leu Ser Arg Ser Pro Ser Pro Phe Thr His Thr His Leu Ala Gln
1185                    1190                    1195                    1200

Gly Tyr Arg Arg Gly Ala Lys Lys Leu Glu Ser Ser Glu Glu Asn Leu
                1205                    1210                    1215

Ser Ser Glu Asp Glu Glu Leu Pro Cys Phe Gln His Leu Leu Phe Gly
            1220                    1225                    1230

Lys Val Asn Asn Ile Pro Ser Gln Ser Thr Arg His Ser Thr Val Ala
            1235                    1240                    1245

Thr Glu Cys Leu Ser Lys Asn Thr Glu Glu Asn Leu Leu Ser Leu Lys
        1250                    1255                    1260

Asn Ser Leu Asn Asp Cys Ser Asn Gln Val Ile Leu Ala Lys Ala Ser
1265                    1270                    1275                    1280

Gln Glu His His Leu Ser Glu Glu Thr Lys Cys Ser Ala Ser Leu Phe
                1285                    1290                    1295

Ser Ser Gln Cys Ser Glu Leu Glu Asp Leu Thr Ala Asn Thr Asn Thr
            1300                    1305                    1310

Gln Asp Pro Phe Leu Ile Gly Ser Ser Lys Gln Met Arg His Gln Ser
            1315                    1320                    1325

Glu Ser Gln Gly Val Gly Leu Ser Asp Lys Glu Leu Val Ser Asp Asp
        1330                    1335                    1340

Glu Glu Arg Gly Thr Gly Leu Glu Glu Asn Lys Lys Ser Lys Ala Trp
1345                    1350                    1355                    1360

Ile Gln Thr (2) INFORMATION FOR SEQ ID NO:24:

(i) SEQUENCE CHARACTERISTICS:
    (A) LENGTH: 1852 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:24:

```
Met  Asp  Leu  Ser  Ala  Leu  Arg  Val  Glu  Glu  Val  Gln  Asn  Val  Ile  Asn
1                   5                   10                      15

Ala  Met  Gln  Lys  Ile  Leu  Glu  Cys  Pro  Ile  Cys  Leu  Glu  Leu  Ile  Lys
               20                   25                      30

Glu  Pro  Val  Ser  Thr  Lys  Cys  Asp  His  Ile  Phe  Cys  Lys  Phe  Cys  Met
               35                   40                      45

Leu  Lys  Leu  Leu  Asn  Gln  Lys  Gly  Pro  Ser  Gln  Cys  Pro  Leu  Cys
          50                   55                      60

Lys  Asn  Asp  Ile  Thr  Lys  Arg  Ser  Leu  Gln  Glu  Ser  Thr  Arg  Phe  Ser
65                       70                   75                          80

Gln  Leu  Val  Glu  Glu  Leu  Leu  Lys  Ile  Ile  Cys  Ala  Phe  Gln  Leu  Asp
               85                        90                              95

Thr  Gly  Leu  Glu  Tyr  Ala  Asn  Ser  Tyr  Asn  Phe  Ala  Lys  Lys  Glu  Asn
               100                 105                           110

Asn  Ser  Pro  Glu  His  Leu  Lys  Asp  Glu  Val  Ser  Ile  Ile  Gln  Ser  Met
          115                      120                      125

Gly  Tyr  Arg  Asn  Arg  Ala  Lys  Arg  Leu  Leu  Gln  Ser  Glu  Pro  Glu  Asn
          130                 135                      140

Pro  Ser  Leu  Gln  Glu  Thr  Ser  Leu  Ser  Val  Gln  Leu  Ser  Asn  Leu  Gly
145                      150                      155                         160

Thr  Val  Arg  Thr  Leu  Arg  Thr  Lys  Gln  Arg  Ile  Gln  Pro  Gln  Lys  Thr
                    165                      170                         175

Ser  Val  Tyr  Ile  Glu  Leu  Gly  Ser  Asp  Ser  Ser  Glu  Asp  Thr  Val  Asn
               180                      185                           190

Lys  Ala  Thr  Tyr  Cys  Ser  Val  Gly  Asp  Gln  Glu  Leu  Leu  Gln  Ile  Thr
               195                 200                           205

Pro  Gln  Gly  Thr  Arg  Asp  Glu  Ile  Ser  Leu  Asp  Ser  Ala  Lys  Lys  Ala
     210                      215                      220

Ala  Cys  Glu  Phe  Ser  Glu  Thr  Asp  Val  Thr  Asn  Thr  Glu  His  His  Gln
225                      230                      235                         240

Pro  Ser  Asn  Asn  Asp  Leu  Asn  Thr  Thr  Glu  Lys  Arg  Ala  Ala  Glu  Arg
               245                      250                           255

His  Pro  Glu  Lys  Tyr  Gln  Gly  Ser  Ser  Val  Ser  Asn  Leu  His  Val  Glu
               260                      265                      270

Pro  Cys  Gly  Thr  Asn  Thr  His  Ala  Ser  Ser  Leu  Gln  His  Glu  Asn  Ser
               275                 280                      285

Ser  Leu  Leu  Leu  Thr  Lys  Asp  Arg  Met  Asn  Val  Glu  Lys  Ala  Glu  Phe
     290                      295                      300

Cys  Asn  Lys  Ser  Lys  Gln  Pro  Gly  Leu  Ala  Arg  Ser  Gln  His  Asn  Arg
305                      310                      315                         320

Trp  Ala  Gly  Ser  Lys  Glu  Thr  Cys  Asn  Asp  Arg  Arg  Thr  Pro  Ser  Thr
               325                      330                           335

Glu  Lys  Lys  Val  Asp  Leu  Asn  Ala  Asp  Pro  Leu  Cys  Glu  Arg  Lys  Glu
               340                      345                           350

Trp  Asn  Lys  Gln  Lys  Leu  Pro  Cys  Ser  Glu  Asn  Pro  Arg  Asp  Thr  Glu
          355                      360                      365

Asp  Val  Pro  Trp  Ile  Thr  Leu  Asn  Ser  Ser  Ile  Gln  Lys  Val  Asn  Glu
     370                      375                      380

Trp  Phe  Ser  Arg  Ser  Asp  Glu  Leu  Leu  Gly  Ser  Asp  Ser  His  Asp
385                      390                      395                         400

Gly  Glu  Ser  Glu  Ser  Asn  Ala  Lys  Val  Ala  Asp  Val  Leu  Asp  Val  Leu
                    405                      410                           415

Asn  Glu  Val  Asp  Glu  Tyr  Ser  Gly  Ser  Ser  Glu  Lys  Ile  Asp  Leu  Leu
```

-continued

```
                           420                         425                         430
    Ala Ser Asp Pro His Glu Ala Leu Ile Cys Lys Ser Arg Val His
            435                     440                     445
    Ser Lys Ser Val Glu Ser Asn Ile Glu Asp Lys Ile Phe Gly Lys Thr
    450                     455                     460
    Tyr Arg Lys Lys Ala Ser Leu Pro Asn Leu Ser His Val Thr Glu Asn
    465                     470                     475                     480
    Leu Ile Ile Gly Ala Phe Val Thr Glu Pro Gln Ile Ile Gln Glu Arg
                            485                     490                     495
    Pro Leu Thr Asn Lys Leu Lys Arg Lys Arg Pro Thr Ser Gly Leu
                    500                     505                     510
    His Pro Glu Asp Phe Ile Lys Lys Ala Asp Leu Ala Val Gln Lys Thr
                515                     520                     525
    Pro Glu Met Ile Asn Gln Gly Thr Asn Gln Thr Glu Gln Asn Gly Gln
            530                     535                     540
    Val Met Asn Ile Thr Asn Ser Gly His Glu Asn Lys Thr Lys Gly Asp
    545                     550                     555                     560
    Ser Ile Gln Asn Glu Lys Asn Pro Asn Pro Ile Glu Ser Leu Glu Lys
                            565                     570                     575
    Glu Ser Ala Phe Lys Thr Lys Ala Glu Pro Ile Ser Ser Ser Ile Ser
                    580                     585                     590
    Asn Met Glu Leu Glu Leu Asn Ile His Asn Ser Lys Ala Pro Lys Lys
                595                     600                     605
    Asn Arg Leu Arg Arg Lys Ser Ser Thr Arg His Ile His Ala Leu Glu
            610                     615                     620
    Leu Val Val Ser Arg Asn Leu Ser Pro Pro Asn Cys Thr Glu Leu Gln
    625                     630                     635                     640
    Ile Asp Ser Cys Ser Ser Ser Glu Glu Ile Lys Lys Lys Lys Tyr Asn
                            645                     650                     655
    Gln Met Pro Val Arg His Ser Arg Asn Leu Gln Leu Met Glu Gly Lys
                    660                     665                     670
    Glu Pro Ala Thr Gly Ala Lys Lys Ser Asn Lys Pro Asn Glu Gln Thr
                675                     680                     685
    Ser Lys Arg His Asp Ser Asp Thr Phe Pro Glu Leu Lys Leu Thr Asn
            690                     695                     700
    Ala Pro Gly Ser Phe Thr Lys Cys Ser Asn Thr Ser Glu Leu Lys Glu
    705                     710                     715                     720
    Phe Val Asn Pro Ser Leu Pro Arg Glu Glu Lys Glu Glu Lys Leu Glu
                            725                     730                     735
    Thr Val Lys Val Ser Asn Asn Ala Glu Asp Pro Lys Asp Leu Met Leu
                    740                     745                     750
    Ser Gly Glu Arg Val Leu Gln Thr Glu Arg Ser Val Glu Ser Ser Ser
                755                     760                     765
    Ile Ser Leu Val Pro Gly Thr Asp Tyr Gly Thr Gln Glu Ser Ile Ser
            770                     775                     780
    Leu Leu Glu Val Ser Thr Leu Gly Lys Ala Lys Thr Glu Pro Asn Lys
    785                     790                     795                     800
    Cys Val Ser Gln Cys Ala Ala Phe Glu Asn Pro Lys Gly Leu Ile His
                            805                     810                     815
    Gly Cys Ser Lys Asp Asn Arg Asn Asp Thr Glu Gly Phe Lys Tyr Pro
                    820                     825                     830
    Leu Gly His Glu Val Asn His Ser Arg Glu Thr Ser Ile Glu Met Glu
                835                     840                     845
```

```
Glu  Ser  Glu  Leu  Asp  Ala  Gln  Tyr  Leu  Gln  Asn  Thr  Phe  Lys  Val  Ser
         850                 855                 860

Lys  Arg  Gln  Ser  Phe  Ala  Pro  Phe  Ser  Asn  Pro  Gly  Asn  Ala  Glu  Glu
865                      870                 875                      880

Glu  Cys  Ala  Thr  Phe  Ser  Ala  His  Ser  Gly  Ser  Leu  Lys  Lys  Gln  Ser
                    885                 890                           895

Pro  Lys  Val  Thr  Phe  Glu  Cys  Glu  Gln  Lys  Glu  Glu  Asn  Gln  Gly  Lys
                    900                 905                      910

Asn  Glu  Ser  Asn  Ile  Lys  Pro  Val  Gln  Thr  Val  Asn  Ile  Thr  Ala  Gly
               915                 920                 925

Phe  Pro  Val  Val  Gly  Gln  Lys  Asp  Lys  Pro  Val  Asp  Asn  Ala  Lys  Cys
          930                 935                 940

Ser  Ile  Lys  Gly  Gly  Ser  Arg  Phe  Cys  Leu  Ser  Ser  Gln  Phe  Arg  Gly
945                      950                 955                           960

Asn  Glu  Thr  Gly  Leu  Ile  Thr  Pro  Asn  Lys  His  Gly  Leu  Leu  Gln  Asn
                    965                 970                           975

Pro  Tyr  Arg  Ile  Pro  Pro  Leu  Phe  Pro  Ile  Lys  Ser  Phe  Val  Lys  Thr
               980                 985                 990

Lys  Cys  Lys  Lys  Asn  Leu  Leu  Glu  Glu  Asn  Phe  Glu  Glu  His  Ser  Met
          995                 1000                1005

Ser  Pro  Glu  Arg  Glu  Met  Gly  Asn  Glu  Asn  Ile  Pro  Ser  Thr  Val  Ser
     1010                1015                1020

Thr  Ile  Ser  Arg  Asn  Asn  Ile  Arg  Glu  Asn  Val  Phe  Lys  Glu  Ala  Ser
1025                      1030                1035                      1040

Ser  Ser  Asn  Ile  Asn  Glu  Val  Gly  Ser  Ser  Thr  Asn  Glu  Val  Gly  Ser
                    1045                1050                      1055

Ser  Ile  Asn  Glu  Ile  Gly  Ser  Ser  Asp  Glu  Asn  Ile  Gln  Ala  Glu  Leu
                    1060                1065                      1070

Gly  Arg  Asn  Arg  Gly  Pro  Lys  Leu  Asn  Ala  Met  Leu  Arg  Leu  Gly  Val
                    1075                1080                      1085

Leu  Gln  Pro  Glu  Val  Tyr  Lys  Gln  Ser  Leu  Pro  Gly  Ser  Asn  Cys  Lys
                    1090                1095                1100

His  Pro  Glu  Ile  Lys  Lys  Gln  Glu  Tyr  Glu  Glu  Val  Val  Gln  Thr  Val
1105                      1110                1115                      1120

Asn  Thr  Asp  Phe  Ser  Pro  Tyr  Leu  Ile  Ser  Asp  Asn  Leu  Glu  Gln  Pro
                    1125                1130                      1135

Met  Gly  Ser  Ser  His  Ala  Ser  Gln  Val  Cys  Ser  Glu  Thr  Pro  Asp  Asp
                    1140                1145                      1150

Leu  Leu  Asp  Asp  Gly  Glu  Ile  Lys  Glu  Asp  Thr  Ser  Phe  Ala  Glu  Asn
                    1155                1160                      1165

Asp  Ile  Lys  Glu  Ser  Ser  Ala  Val  Phe  Ser  Lys  Ser  Val  Gln  Lys  Gly
          1170                1175                      1180

Glu  Leu  Ser  Arg  Ser  Pro  Ser  Pro  Phe  Thr  His  Thr  His  Leu  Ala  Gln
1185                      1190                1195                      1200

Gly  Tyr  Arg  Arg  Gly  Ala  Lys  Lys  Leu  Glu  Ser  Ser  Glu  Glu  Asn  Leu
                    1205                1210                      1215

Ser  Ser  Glu  Asp  Glu  Glu  Leu  Pro  Cys  Phe  Gln  His  Leu  Leu  Phe  Gly
               1220                1225                      1230

Lys  Val  Asn  Asn  Ile  Pro  Ser  Gln  Ser  Thr  Arg  His  Ser  Thr  Val  Ala
          1235                1240                      1245

Thr  Glu  Cys  Leu  Ser  Lys  Asn  Thr  Glu  Glu  Asn  Leu  Leu  Ser  Leu  Lys
          1250                1255                      1260

Asn  Ser  Leu  Asn  Asp  Cys  Ser  Asn  Gln  Val  Ile  Leu  Ala  Lys  Ala  Ser
1265                      1270                1275                      1280
```

```
Gln Glu His His Leu Ser Glu Glu Thr Lys Cys Ser Ala Ser Leu Phe
                1285                1290                1295
Ser Ser Gln Cys Ser Glu Leu Glu Asp Leu Thr Ala Asn Thr Asn Thr
            1300                1305                1310
Gln Asp Pro Phe Leu Ile Gly Ser Ser Lys Gln Met Arg His Gln Ser
            1315                1320                1325
Glu Ser Gln Gly Val Gly Leu Ser Asp Lys Glu Leu Val Ser Asp Asp
        1330                1335                1340
Glu Glu Arg Gly Thr Gly Leu Glu Glu Asn Asn Gln Glu Glu Gln Ser
1345                1350                1355                1360
Met Asp Ser Asn Leu Gly Glu Ala Ala Ser Gly Cys Glu Ser Glu Thr
                1365                1370                1375
Ser Val Ser Glu Asp Cys Ser Gly Leu Ser Ser Gln Ser Asp Ile Leu
            1380                1385                1390
Thr Thr Gln Gln Arg Asp Thr Met Gln His Asn Leu Ile Lys Leu Gln
            1395                1400                1405
Gln Glu Met Ala Glu Leu Glu Ala Val Leu Glu Gln His Gly Ser Gln
        1410                1415                1420
Pro Ser Asn Ser Tyr Pro Ser Ile Ile Ser Asp Ser Ser Ala Leu Glu
1425                1430                1435                1440
Asp Leu Arg Asn Pro Glu Gln Ser Thr Ser Glu Lys Ala Val Leu Thr
                1445                1450                1455
Ser Gln Lys Ser Ser Glu Tyr Pro Ile Ser Gln Asn Pro Glu Gly Leu
            1460                1465                1470
Ser Ala Asp Lys Phe Glu Val Ser Ala Asp Ser Ser Thr Ser Lys Asn
            1475                1480                1485
Lys Glu Pro Gly Val Glu Arg Ser Ser Pro Ser Lys Cys Pro Ser Leu
        1490                1495                1500
Asp Asp Arg Trp Tyr Met His Ser Cys Ser Gly Ser Leu Gln Asn Arg
1505                1510                1515                1520
Asn Tyr Pro Ser Gln Glu Glu Leu Ile Lys Val Val Asp Val Glu Glu
                1525                1530                1535
Gln Gln Leu Glu Glu Ser Gly Pro His Asp Leu Thr Glu Thr Ser Tyr
            1540                1545                1550
Leu Pro Arg Gln Asp Leu Glu Gly Thr Pro Tyr Leu Glu Ser Gly Ile
            1555                1560                1565
Ser Leu Phe Ser Asp Asp Pro Glu Ser Asp Pro Ser Glu Asp Arg Ala
        1570                1575                1580
Pro Glu Ser Ala Arg Val Gly Asn Ile Pro Ser Ser Thr Ser Ala Leu
1585                1590                1595                1600
Lys Val Pro Gln Leu Lys Val Ala Glu Ser Ala Gln Ser Pro Ala Ala
                1605                1610                1615
Ala His Thr Thr Asp Thr Ala Gly Tyr Asn Ala Met Glu Glu Ser Val
            1620                1625                1630
Ser Arg Glu Lys Pro Glu Leu Thr Ala Ser Thr Glu Arg Val Asn Lys
            1635                1640                1645
Arg Met Ser Met Val Val Ser Gly Leu Thr Pro Glu Glu Phe Met Leu
        1650                1655                1660
Val Tyr Lys Phe Ala Arg Lys His His Ile Thr Leu Thr Asn Leu Ile
1665                1670                1675                1680
Thr Glu Glu Thr Thr His Val Val Met Lys Thr Asp Ala Glu Phe Val
                1685                1690                1695
Cys Glu Arg Thr Leu Lys Tyr Phe Leu Gly Ile Ala Gly Gly Lys Trp
```

|      |      |      | 1700 |      |      |      |      | 1705 |      |      |      |      | 1710 |      |
|------|------|------|------|------|------|------|------|------|------|------|------|------|------|------|
| Val  | Val  | Ser  | Tyr  | Phe  | Trp  | Val  | Thr  | Gln  | Ser  | Ile  | Lys  | Glu  | Arg  | Lys  | Met  |
|      |      |      | 1715 |      |      |      | 1720 |      |      |      |      | 1725 |      |      |
| Leu  | Asn  | Glu  | His  | Asp  | Phe  | Glu  | Val  | Arg  | Gly  | Asp  | Val  | Val  | Asn  | Gly  | Arg  |
|      |      |      | 1730 |      |      |      | 1735 |      |      |      |      | 1740 |      |      |
| Asn  | His  | Gln  | Gly  | Pro  | Lys  | Arg  | Ala  | Arg  | Glu  | Ser  | Gln  | Asp  | Arg  | Lys  | Ile  |
| 1745 |      |      |      |      | 1750 |      |      |      |      | 1755 |      |      |      |      | 1760 |
| Phe  | Arg  | Gly  | Leu  | Glu  | Ile  | Cys  | Cys  | Tyr  | Gly  | Pro  | Phe  | Thr  | Asn  | Met  | Pro  |
|      |      |      |      | 1765 |      |      |      |      | 1770 |      |      |      |      | 1775 |      |
| Thr  | Asp  | Gln  | Leu  | Glu  | Trp  | Met  | Val  | Gln  | Leu  | Cys  | Gly  | Ala  | Ser  | Val  | Val  |
|      |      |      |      | 1780 |      |      |      | 1785 |      |      |      |      | 1790 |      |      |
| Lys  | Glu  | Leu  | Ser  | Ser  | Phe  | Thr  | Leu  | Gly  | Thr  | Gly  | Val  | His  | Pro  | Ile  | Val  |
|      |      |      | 1795 |      |      |      | 1800 |      |      |      |      | 1805 |      |      |
| Val  | Val  | Gln  | Pro  | Asp  | Ala  | Trp  | Thr  | Glu  | Asp  | Asn  | Gly  | Phe  | His  | Ala  | Ile  |
|      | 1810 |      |      |      |      | 1815 |      |      |      |      | 1820 |      |      |      |      |
| Gly  | Gln  | Met  | Cys  | Glu  | Ala  | Pro  | Val  | Val  | Thr  | Arg  | Glu  | Trp  | Val  | Leu  | Asp  |
| 1825 |      |      |      |      | 1830 |      |      |      |      | 1835 |      |      |      |      | 1840 |
| Ser  | Val  | Ala  | Leu  | Tyr  | Gln  | Cys  | Gln  | Glu  | Leu  | Asp  | Thr  |      |      |      |      |
|      |      |      |      | 1845 |      |      |      |      | 1850 |      |      |      |      |      |      |